US012559500B2

(12) United States Patent
Kim et al.

(10) Patent No.: US 12,559,500 B2
(45) Date of Patent: Feb. 24, 2026

(54) LIGHT-EMITTING DEVICE AND ELECTRONIC APPARATUS INCLUDING LIGHT-EMITTING DEVICE

(71) Applicant: Samsung Display Co., Ltd., Yongin-si (KR)

(72) Inventors: Hyerim Kim, Yongin-si (KR); Mikyung Kim, Yongin-si (KR); Yon Namkoong, Yongin-si (KR); Jihyun Seo, Yongin-si (KR); Hyunsu Shin, Yongin-si (KR); Hanbyul Jang, Yongin-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 923 days.

(21) Appl. No.: 17/719,583

(22) Filed: Apr. 13, 2022

(65) Prior Publication Data

US 2022/0352471 A1 Nov. 3, 2022

(30) Foreign Application Priority Data

Apr. 16, 2021 (KR) ........................ 10-2021-0050116

(51) Int. Cl.

| | |
|---|---|
| ***C07D 491/147*** | (2006.01) |
| ***C07C 211/54*** | (2006.01) |
| ***C07C 211/61*** | (2006.01) |
| ***C07D 333/76*** | (2006.01) |
| ***C07D 409/14*** | (2006.01) |
| ***C07F 7/18*** | (2006.01) |
| ***C09K 11/06*** | (2006.01) |
| ***H10K 85/40*** | (2023.01) |
| ***H10K 85/60*** | (2023.01) |
| *H10K 50/11* | (2023.01) |
| *H10K 50/15* | (2023.01) |
| *H10K 50/18* | (2023.01) |
| *H10K 59/123* | (2023.01) |
| *H10K 101/10* | (2023.01) |
| *H10K 101/30* | (2023.01) |
| *H10K 102/00* | (2023.01) |

(52) U.S. Cl.

CPC ........ *C07D 491/147* (2013.01); *C07C 211/54* (2013.01); *C07C 211/61* (2013.01); *C07D 333/76* (2013.01); *C07D 409/14* (2013.01); *C07F 7/18* (2013.01); *C09K 11/06* (2013.01); *H10K 85/40* (2023.02); *H10K 85/633* (2023.02); *H10K 85/636* (2023.02); *C07C 2603/97* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/15* (2023.02); *H10K 50/181* (2023.02); *H10K 59/123* (2023.02); *H10K 85/615* (2023.02); *H10K 85/624* (2023.02); *H10K 85/626* (2023.02); *H10K 85/654* (2023.02); *H10K 85/657* (2023.02); *H10K 85/6576* (2023.02); *H10K 2101/10* (2023.02); *H10K 2101/30* (2023.02); *H10K 2102/351* (2023.02)

(58) Field of Classification Search

None

See application file for complete search history.

(56) References Cited

U.S. PATENT DOCUMENTS

| | | | | |
|---|---|---|---|---|
| 9,666,819 | B2 | 5/2017 | Park et al. | |
| 10,777,748 | B2 | 9/2020 | Song et al. | |
| 10,991,888 | B2 | 4/2021 | Lee et al. | |
| 2014/0312287 | A1* | 10/2014 | Stoessel ................ | C07C 211/54 252/500 |
| 2020/0035926 | A1* | 1/2020 | Zhou ...................... | H10K 71/00 |
| 2020/0048171 | A1* | 2/2020 | Yamada ................ | C07C 13/465 |
| 2021/0036238 | A1 | 2/2021 | Kim et al. | |

FOREIGN PATENT DOCUMENTS

| | | |
|---|---|---|
| KR | 20100123172 A | 11/2010 |
| KR | 10-1070223 | 10/2011 |
| KR | 10-1493482 | 2/2015 |
| KR | 10-2016-0087991 | 7/2016 |
| KR | 20170084393 A | 7/2017 |
| KR | 10-2018-0047313 | 5/2018 |

(Continued)

OTHER PUBLICATIONS

Li, Xiang-Long, et al. "Highly efficient single-and multi-emission-layer fluorescent/phosphorescent hybrid white organic light-emitting diodes with~ 20% external quantum efficiency." Journal of Materials Chemistry C 3.35 (2015): 9233-9239. (Year: 2015).*

(Continued)

*Primary Examiner* — Robert S Loewe

(74) *Attorney, Agent, or Firm* — CANTOR COLBURN LLP

(57) ABSTRACT

Provided are a light-emitting device and an electronic apparatus. The light-emitting device includes a first electrode, a second electrode facing the first electrode, and an interlayer disposed between the first electrode and the second electrode. The interlayer includes an emission layer and an electron blocking layer, the electron blocking layer includes a first electron blocking layer and a second electron blocking layer. The first electron blocking layer includes a first compound, the second electron blocking layer comprises a second compound, and the first compound is different from the second compound.

20 Claims, 3 Drawing Sheets

(56) References Cited

FOREIGN PATENT DOCUMENTS

| | | |
|---|---|---|
| KR | 10-1857632 | 5/2018 |
| KR | 10-2018-0061825 | 6/2018 |
| KR | 20210015706 A | 2/2021 |

OTHER PUBLICATIONS

Jbbar, R., A. Bahari, and Duha S. Ahmed. "Enhanced Current Efficiency of OLEDs with NPB (5 nm)/TCTA (5 nm) Multilayers Sandwiched Between ITO (Anode) and Alq 3 (50 nm)/LiF (1 nm)/Al (Cathode)." Journal of Electronic Materials 49 (2020): 6276-6282. (Year: 2020).*

Technical data sheet for CBP [4,4'-Bis(N-carbazolyl)-1,1'-biphenyl, 8 pages. (Year: 2025).*

* cited by examiner

LIGHT-EMITTING DEVICE AND ELECTRONIC APPARATUS INCLUDING LIGHT-EMITTING DEVICE

CROSS-REFERENCE TO RELATED APPLICATION(S)

This application claims priority to and benefits of Korean Patent Application No. 10-2021-0050116 under 35 U.S.C. § 119, filed on Apr. 16, 2021 in the Korean Intellectual Property Office, the entire contents of which are incorporated herein by reference.

BACKGROUND

1. Technical Field

Embodiments relate to a light-emitting device and an electronic apparatus including the light-emitting device.

2. Description of the Related Art

Light-emitting devices are self-emissive devices that have wide viewing angles, high contrast ratios, short response times, and excellent characteristics in terms of brightness, driving voltage, and response speed.

Light-emitting devices may include a first electrode on a substrate, and a hole transport region, an emission layer, an electron transport region, and a second electrode sequentially stacked on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transition from an excited state to a ground state to thereby generate light.

It is to be understood that this background of the technology section is, in part, intended to provide useful background for understanding the technology. However, this background of the technology section may also include ideas, concepts, or recognitions that were not part of what was known or appreciated by those skilled in the pertinent art prior to a corresponding effective filing date of the subject matter disclosed herein.

SUMMARY

Embodiments relate to a light-emitting device and an electronic apparatus including the light-emitting device.

Additional aspects will be set forth in part in the description which follows and, in part, will be apparent from the description, or may be learned by practice of the embodiments of the disclosure.

According to embodiments, a light-emitting device may include a first electrode, a second electrode facing the first electrode, and an interlayer disposed between the first electrode and the second electrode, wherein the interlayer may include an emission layer and an electron blocking layer, the electron blocking layer may be between the first electrode and the emission layer, the emission layer may be between the second electrode and the electron blocking layer, the electron blocking layer may include a first electron blocking layer and a second electron blocking layer, the first electron blocking layer may be between the second electron blocking layer and the first electrode, the second electron blocking layer may be between the first electron blocking layer and the emission layer, the first electron blocking layer may include a first compound represented by Formula 1, the second electron blocking layer may include a second compound represented by Formula 2, and the first compound may be different from the second compound.

[Formula 1]

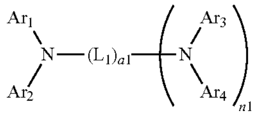

[Formula 2]

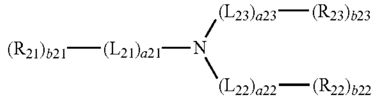

[Formula 3]

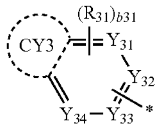

In Formulae 1 to 3, $L_1$ may be a benzene group, a naphthalene group, a pyridine group, a pyridazine group, a pyrimidine group, a pyrazine group, a triazine group, a tetrazine group, a quinoline group, or an isoquinoline group, a1 may be an integer from 0 to 3, $Ar_1$ to $Ar_4$ may each independently be a group represented by Formula 3, a benzene group, a naphthalene group, an anthracene group, a phenanthrene group, a pyridine group, a pyridazine group, a pyrimidine group, a pyrazine group, a triazine group, a tetrazine group, a pentazine group, a dibenzofuran group, a dibenzothiophene group, a dibenzoselenophene group, a carbazole group, a fluorene group, a dibenzosilole group, or a spirobifluorene group, n1 may be an integer of 1 or greater, $Y_{31}$ may be N or C, $Y_{32}$ may be N or C, $Y_{33}$ may be N or C, $Y_{34}$ may be N or C, and at least one of $Y_{31}$ to $Y_{34}$ may be C,

* indicates a binding site to a nitrogen (N) atom in Formula 1,

CY3 may be a $C_3$-$C_{60}$ carbocyclic group or a $C_1$-$C_{60}$ heterocyclic group, $L_{21}$ to $L_{23}$ may each independently be a single bond, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$, a21 to a23 may each independently be an integer from 0 to 3, $R_{21}$ to $R_{23}$ and $R_{31}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_7$-$C_{60}$ aryl alkyl group unsubstituted or substituted with at least one $R_{10a}$, a $C_2$-$C_{60}$ heteroaryl alkyl group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, b21 to b23 may each independently be an integer from 0 to 10, b31 may be an integer from 0 to 3, and $R_{10a}$ may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ may each independently be hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

In an embodiment, the first compound and the second compound may each satisfy Equation 1-1, which is explained below.

In an embodiment, the compound and the second compound may each satisfy Equation 2-1, which is explained below.

In an embodiment, the interlayer may further include a hole transport region between the first electrode and the emission layer and an electron transport region between the emission layer and the second electrode. The hole transport region may include a hole transport layer and the electron blocking layer, the first electron blocking layer may be between the second electron blocking layer and the hole transport layer, the second electron blocking layer may be between the first electron blocking layer and the emission layer, and the hole transport layer may include a third compound represented by Formula 201 or Formula 202, which are explained below.

In an embodiment, the first to third compounds may each satisfy Equations 1-1 and 1-2, which are explained below.

In an embodiment, the emission layer may include a host and a dopant, the dopant may include a phosphorescent dopant, and the host may include a fourth compound represented by Formula 301, which is explained below.

In an embodiment, the first compound, the second compound, and the fourth compound may each satisfy Equations 1-1 and 1-3, which are explained below.

In an embodiment, a thickness of the first electron blocking layer may be in a range of about 5 Angstroms (Å) to about 1,000 Å, and a thickness of the second electron blocking layer may be in a range of about 1 Å to about 100 Å.

In an embodiment, a ratio of a thickness of the second electron blocking layer to a thickness of the first electron blocking layer may be in a range of about 1 to about 10.

In an embodiment, in Formula 1, n1 may be 1 or 2.

In an embodiment, in Formula 1, $L_1$ may be a group represented by one of Formulae 1-1 to 1-3, which are explained below.

In an embodiment, in Formula 1, $Ar_1$ to $Ar_4$ may each independently be a group represented by Formula 3, a benzene group, a naphthalene group, an anthracene group, a phenanthrene group, a pyridine group, a pyrimidine group, a pyrazine group, a triazine group, a dibenzofuran group, a dibenzothiophene group, a dibenzoselenophene group, a carbazole group, a fluorene group, a dibenzosilole group, or a spirobifluorene group, and at least one of $Ar_1$ to $Ar_4$ may be a group represented by Formula 3.

In an embodiment, in Formula 1, $Ar_1$ may be a group represented by Formula 3, and any two of $Ar_2$ to $Ar_4$ may be identical to each other.

In an embodiment, the group represented by Formula 3 may be a group represented by one of Formulae 3-1 to 3-4, which are explained below.

In an embodiment, in Formula 3, CY3 may be a group represented by one of Formulae CY3-1 to CY3-4, which are explained below.

In an embodiment, in Formula 2, $L_{21}$ to $L_{23}$ may each independently be a single bond; a phenylene group or a naphthylene group; or a phenylene group or a naphthylene group, each unsubstituted or substituted with deuterium, —F, —Cl, —Br, —I, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, or any combination thereof.

In an embodiment, $R_{21}$ to $R_{23}$ and $R_{31}$ may each independently be hydrogen, deuterium, —F, or a cyano group; or a phenyl group, a biphenyl group, a naphthyl group, a pyridinyl group, a pyrimidinyl group, a pyridazinyl group, a pyrazinyl group, a triazinyl group, a quinolinyl group, an isoquinolinyl group, a naphthyl group, an anthracenyl group, a phenanthrenyl group, a dibenzothiophenyl group, or a spirobifluorenyl group, each unsubstituted or substituted with deuterium, —F, a cyano group, a $C_1$-$C_{20}$ alkyl group, a phenyl group, a biphenyl group, a naphthyl group, a pyridinyl group, a pyrimidinyl group, a pyridazinyl group, a pyrazinyl group, a triazinyl group, a quinolinyl group, an isoquinolinyl group, an anthracenyl group, a phenanthrenyl group, a $C_1$-$C_{20}$ alkylphenyl group, a dibenzothiophenyl group, a spirobifluorenyl group, or any combination thereof.

According to an aspect of another embodiment, an electronic apparatus may include the light-emitting device.

In an embodiment, the electronic apparatus may further include a thin-film transistor. The thin-film transistor may include a source electrode and a drain electrode, and the first electrode of the light-emitting device may be electrically connected to at least one of the source electrode and the drain electrode of the thin-film transistor.

In an embodiment, the electronic apparatus may further include a color filter, a color-conversion layer, a touchscreen layer, a polarization layer, or any combination thereof.

BRIEF DESCRIPTION OF THE DRAWINGS

The above and other aspects and features of the disclosure will become more apparent be describing in detail embodiments thereof with reference to the accompanying drawings, in which.

DETAILED DESCRIPTION OF THE EMBODIMENTS

Figure 1:
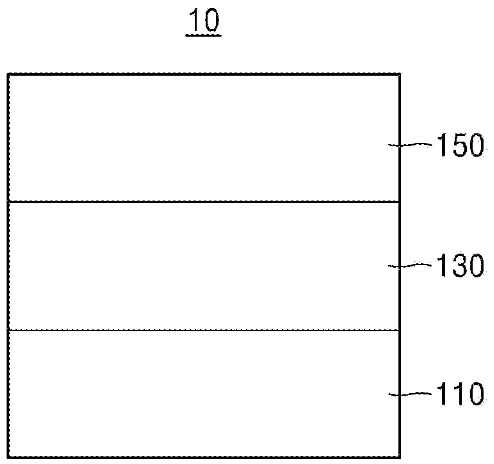
FIG. 1 is a schematic cross-sectional view of a light-emitting device according to an embodiment.

The disclosure will now be described more fully hereinafter with reference to the accompanying drawings, in which embodiments are shown. This disclosure may, however, be embodied in different forms and should not be construed as limited to the embodiments set forth herein. Rather, these embodiments are provided so that this disclosure will be thorough and complete, and will fully convey the scope of the disclosure to those skilled in the art.

In the drawings, the sizes, thicknesses, ratios, and dimensions of the elements may be exaggerated for ease of description and for clarity. Like numbers refer to like elements throughout.

In the description, it will be understood that when an element (or region, layer, part, etc.) is referred to as being “on”, “connected to”, or “coupled to” another element, it can be directly on, connected to, or coupled to the other element, or one or more intervening elements may be present therebetween. In a similar sense, when an element (or region, layer, part, etc.) is described as “covering” another element, it can directly cover the other element, or one or more intervening elements may be present therebetween.

In the description, when an element is “directly on,” “directly connected to,” or “directly coupled to” another element, there are no intervening elements present. For example, “directly on” may mean that two layers or two elements are disposed without an additional element such as an adhesion element therebetween.

As used herein, the expressions used in the singular such as “a,” “an,” and “the,” are intended to include the plural forms as well, unless the context clearly indicates otherwise.

As used herein, the term “and/or” includes any and all combinations of one or more of the associated listed items. For example, “A and/or B” may be understood to mean “A, B, or A and B.” The terms “and” and “or” may be used in the conjunctive or disjunctive sense and may be understood to be equivalent to “and/or”.

In the specification and the claims, the term “at least one of” is intended to include the meaning of “at least one selected from the group of” for the purpose of its meaning and interpretation. For example, “at least one of A and B” may be understood to mean “A, B, or A and B.” When preceding a list of elements, the term, “at least one of,” modifies the entire list of elements and does not modify the individual elements of the list.

It will be understood that, although the terms first, second, etc. may be used herein to describe various elements, these elements should not be limited by these terms. These terms are only used to distinguish one element from another element. Thus, a first element could be termed a second element without departing from the teachings of the disclosure. Similarly, a second element could be termed a first element, without departing from the scope of the disclosure.

The spatially relative terms “below”, “beneath”, “lower”, “above”, “upper”, or the like, may be used herein for ease of description to describe the relations between one element or component and another element or component as illustrated in the drawings. It will be understood that the spatially relative terms are intended to encompass different orientations of the device in use or operation, in addition to the orientation depicted in the drawings. For example, in the case where a device illustrated in the drawing is turned over, the device positioned “below” or “beneath” another device may be placed “above” another device. Accordingly, the illustrative term “below” may include both the lower and upper positions. The device may also be oriented in other directions and thus the spatially relative terms may be interpreted differently depending on the orientations.

The terms “about” or “approximately” as used herein is inclusive of the stated value and means within an acceptable range of deviation for the recited value as determined by one of ordinary skill in the art, considering the measurement in question and the error associated with measurement of the recited quantity (i.e., the limitations of the measurement system). For example, “about” may mean within one or more standard deviations, or within ±20%, ±10%, or ±5% of the stated value.

It should be understood that the terms “comprises,” “comprising,” “includes,” “including,” “have,” “having,” “contains,” “containing,” and the like are intended to specify the presence of stated features, integers, steps, operations, elements, components, or combinations thereof in the disclosure, but do not preclude the presence or addition of one or more other features, integers, steps, operations, elements, components, or combinations thereof.

Unless otherwise defined or implied herein, all terms (including technical and scientific terms) used have the same meaning as commonly understood by those skilled in the art to which this disclosure pertains. It will be further understood that terms, such as those defined in commonly used dictionaries, should be interpreted as having a meaning that is consistent with their meaning in the context of the relevant art and should not be interpreted in an ideal or excessively formal sense unless clearly defined in the specification.

According to an embodiment, a light-emitting device may include a first electrode; a second electrode facing the first electrode; and an interlayer disposed between the first electrode and the second electrode, wherein the interlayer may include an emission layer and an electron blocking layer, the electron blocking layer may be between the first electrode and the emission layer, the emission layer may be between the second electrode and the electron blocking layer, the electron blocking layer may include a first electron blocking layer and a second electron blocking layer, the first electron blocking layer may be between the second electron blocking layer and the first electrode, the second electron blocking layer may be between the first electron blocking layer and the emission layer, the first electron blocking layer may include a first compound represented by Formula 1, the second electron blocking layer may include a second compound represented by Formula 2, and the first compound may be different from the second compound:

[Formula 1]

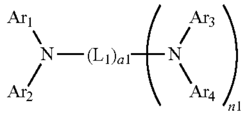

[Formula 2]

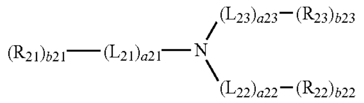

[Formula 3]

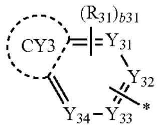

In Formulae 1 to 3, $L_1$ may be a benzene group, a naphthalene group, a pyridine group, a pyridazine group, a pyrimidine group, a pyrazine group, a triazine group, a tetrazine group, a quinoline group, or an isoquinoline group.

In an embodiment, in Formula 1, $L_1$ may be a group represented by one of Formulae 1-1 to 1-3.

1-1

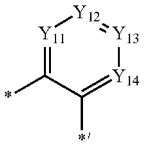

1-2

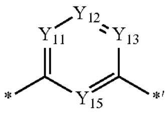

1-3

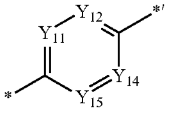

In Formulae 1-1 to 1-3, $Y_{11}$ may be N or $C(R_{11})$, $Y_{12}$ may be N or $C(R_{12})$, $Y_{13}$ may be N or $C(R_{13})$, $Y_{14}$ may be N or $C(R_{14})$, and $Y_{15}$ may be N or $C(R_{15})$.

In an embodiment, at least one of $Y_{11}$ to $Y_{15}$ may be N.

In embodiments, at least one of $Y_{11}$ to $Y_{15}$ may be N.

In embodiments, $Y_{11}$ may be $C(R_{11})$, $Y_{12}$ may be $C(R_{12})$, $Y_{13}$ may be $C(R_{13})$, $Y_{14}$ may be $C(R_{14})$ and $Y_{15}$ may be $C(R_{15})$.

In an embodiment, in Formula 1, $L_1$ may be a group represented by Formula 1-3.

In an embodiment, in Formula 1, $L_1$ may be a group represented by Formula 1-3, and at least one of Conditions 1-1 to 1-5 may be satisfied.

[Condition 1-1]

$Y_{11}$ may be N, $Y_{12}$ may be $C(R_{12})$, $Y_{14}$ may be $C(R_{14})$, and $Y_{15}$ may be $C(R_{15})$.

[Condition 1-2]

$Y_{12}$ may be N, $Y_{11}$ may be $C(R_{11})$, $Y_{14}$ may be $C(R_{14})$, and $Y_{15}$ may be $C(R_{15})$.

[Condition 1-3]

$Y_{14}$ may be N, $Y_{11}$ may be $C(R_{11})$, $Y_{12}$ may be $C(R_{12})$, and $Y_{15}$ may be $C(R_{15})$.

[Condition 1-4]

$Y_{15}$ may be N, $Y_{11}$ may be $C(R_{11})$, $Y_{12}$ may be $C(R_{12})$, and $Y_{14}$ may be $C(R_{14})$.

[Condition 1-5]

$Y_{11}$ may be $C(R_{11})$, $Y_{12}$ may be $C(R_{12})$, $Y_{14}$ may be $C(R_{14})$, and $Y_{15}$ may be $C(R_{15})$.

In Formulae 1-1 to 1-3, $R_{11}$ to $R_{15}$ may each independently be the same as described in connection with $R_{21}$ in Formula 2.

In Formulae 1-1 to 1-3, * indicates a binding site to a nitrogen (N) atom bound to $Ar_1$ and $Ar_2$ in Formula 1, and *' indicates a binding site to a nitrogen (N) atom bound to $Ar_3$ and $Ar_4$ in Formula 1.

In Formulae 1 to 3, a1 may each independently be an integer from 0 to 3.

In Formulae 1 to 3, a1 may indicate the number of $L_1$(s). When a1 is 2 or greater, at least two $L_1$(s) may be identical to or different from each other.

In Formulae 1 to 3, $Ar_1$ to $Ar_4$ may each independently be a group represented by Formula 3, a benzene group, a naphthalene group, an anthracene group, a phenanthrene group, a pyridine group, a pyridazine group, a pyrimidine group, a pyrazine group, a triazine group, a tetrazine group, a pentazine group, a dibenzofuran group, a dibenzothiophene group, a dibenzoselenophene group, a carbazole group, a fluorene group, a dibenzosilole group, or a spiro-bifluorene group.

In an embodiment, $Ar_1$ to $Ar_4$ may each independently be a group represented by Formula 3, a benzene group, a naphthalene group, an anthracene group, a phenanthrene group, a pyridine group, a pyrimidine group, a pyrazine group, a triazine group, a dibenzofuran group, a dibenzothiophene group, a dibenzoselenophene group, a carbazole group, a fluorene group, a dibenzosilole group, or a spiro-bifluorene group, and at least one of $Ar_1$ to $Ar_4$ may be a group represented by Formula 3.

In an embodiment, $Ar_1$ to $Ar_4$ may each independently be a group represented by Formula 3 or a group represented by one of Formulae 4-1 to 4-34, and at least one of $Ar_1$ to $Ar_4$ may be a group represented by Formula 3.

4-1

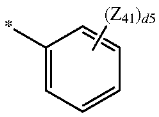

4-2

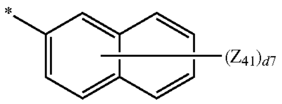

4-3

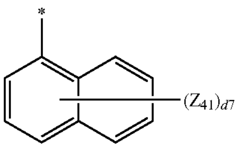

4-4

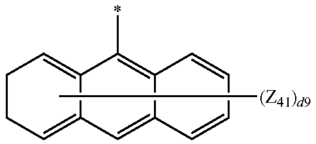

-continued
4-5
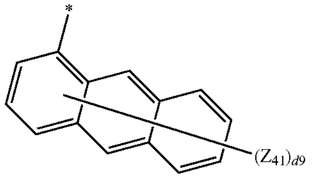
4-6
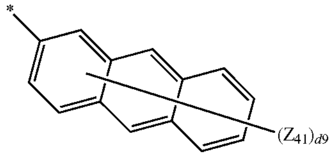
4-7
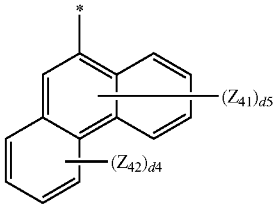
4-8
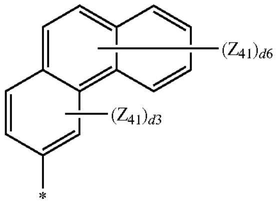
4-9
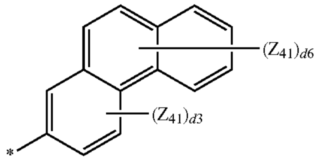
4-10
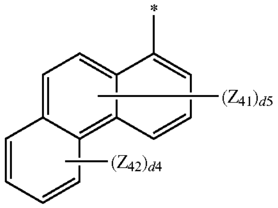
4-11
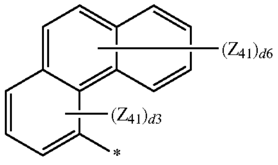
4-12
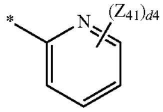
4-13
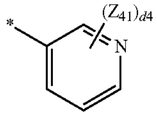
-continued
4-14
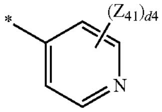
4-15
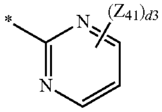
4-16
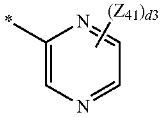
4-17
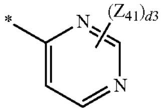
4-18
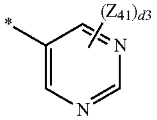
4-19
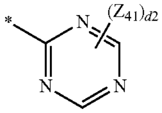
4-20
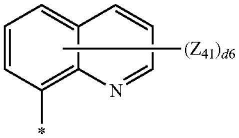
4-21
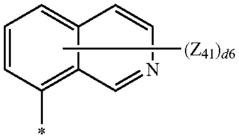
4-22
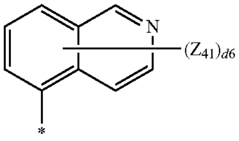
4-23
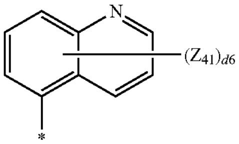
4-24
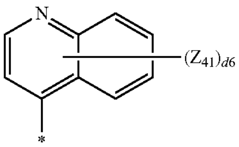

-continued 4-25

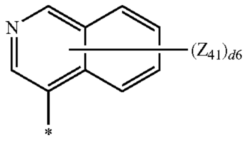

4-26

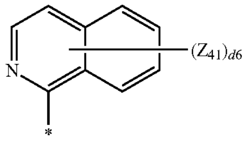

4-27

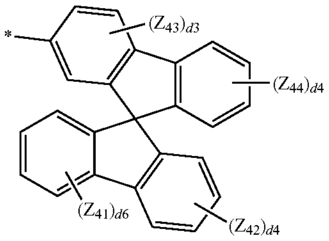

4-28

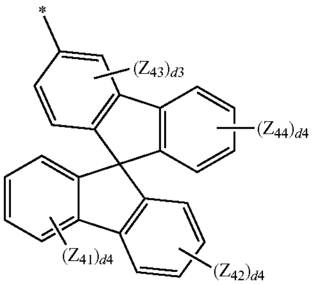

4-29

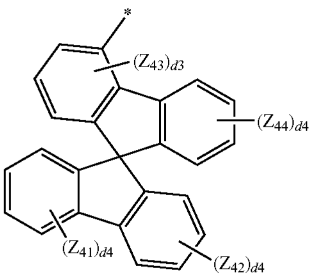

4-30

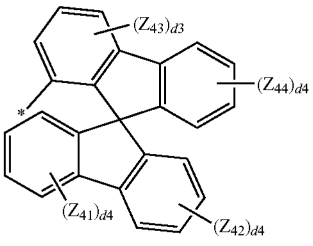

4-31

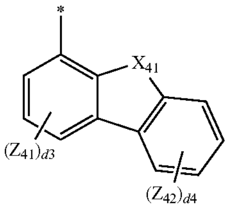

-continued 4-32

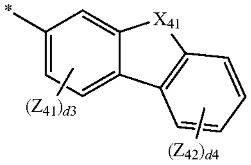

4-33

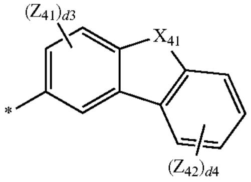

4-34

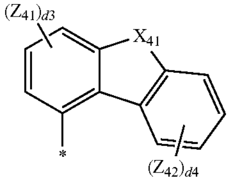

In Formulae 4-1 to 4-34, $X_{41}$ may be $C(R_{41a})(R_{41b})$, $Si(R_{41a})(R_{41b})$, $N(R_{41a})$, O, S, or Se, and $R_{41a}$, $R_{41b}$, and $Z_{41}$ to $Z_{44}$ may each independently be the same as described in connection with $R_{21}$ in Formula 2.

In Formulae 4-1 to 4-34, d2 may be an integer from 0 to 2, d3 may be an integer from 0 to 3, d4 may be an integer from 0 to 4, d5 may be an integer from 0 to 5, d6 may be an integer from 0 to 6, d7 may be an integer from 0 to 7, and d9 may be an integer from 0 to 9.

In Formulae 4-1 to 4-34, * indicates a binding site to an adjacent group.

In Formulae 1 to 3, * indicates a binding site to a nitrogen (N) atom in Formula 1.

In an embodiment, in Formula 1, at least one of $Ar_1$ to $Ar_4$ may be a group represented by Formula 3.

In an embodiment, in Formula 1, any one of $Ar_1$ to $Ar_4$ may be a group represented by Formula 3.

In an embodiment, in Formula 1, $Ar_1$ may be a group represented by Formula 3, and any two of $Ar_2$ to $Ar_4$ may be identical to each other.

In embodiments, in Formula 1, $Ar_1$ may be a group represented by Formula 3, and any two of $Ar_2$ to $Ar_4$ may each independently be a benzene group, a naphthalene group, or a pyridine group.

In Formulae 1 to 3, n1 may be an integer of 1 or greater. For example, n1 may indicate the number of —$N(Ar_3)(Ar_4)$(s) included in the parenthesis in Formula 1. When n1 is 2 or greater, at least two —$N(Ar_3)(Ar_4)$(s) may be identical to or different from each other.

In an embodiment, in Formula 1, n1 may be an integer of 1 or 2.

In embodiments, n1 may be 1.

In Formula 3, $Y_{31}$ may be N or C, $Y_{32}$ may be N or C, $Y_{33}$ may be N or C, $Y_{34}$ may be N or C, and at least one of $Y_{31}$ to $Y_{34}$ may be C.

In an embodiment, at least one of $Y_{31}$ to $Y_{34}$ may be N.

In embodiments, at least one of $Y_{31}$ to $Y_{34}$ may be N.

In embodiments, $Y_{31}$ to $Y_{34}$ may each be C.

In embodiments, the group represented by Formula 3 may be a group represented by one of Formulae 3-1 to 3-4:

3-1

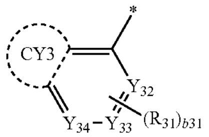

3-2

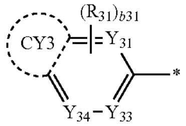

3-3

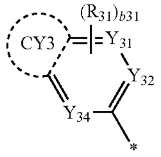

3-4

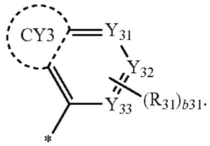

In an embodiment, Formula 3 may be represented by Formula 3-3.

In an embodiment, Formula 3-3 may satisfy any one of Conditions 3-1 to 3-4:

[Condition 3-1]

$Y_{31}$ may be N, $Y_{32}$ may be C, and $Y_{34}$ may be C.

[Condition 3-2]

$Y_{32}$ may be N, $Y_{31}$ may be C, and $Y_{34}$ may be C.

[Condition 3-3]

$Y_{34}$ may be N, $Y_{31}$ may be C, and $Y_{32}$ may be C.

[Condition 3-4]

$Y_{31}$ may be C, $Y_{32}$ may be C, and $Y_{34}$ may be C.

In Formula 3 and in Formulae 3-1 to 3-4, b31 may be an integer from 0 to 3.

In Formula 3 and in Formulae 3-1 to 3-4, b31 may indicate the number of $R_{31}$(s). When a31 is 2 or greater, at least two $L_{31}$(s) may be identical to or different from each other.

In Formula 3 and in Formulae 3-1 to 3-4, * indicates a binding site to a nitrogen (N) atom in Formula 1.

In Formula 3 and in Formulae 3-1 to 3-4, CY3 may be a $C_3$-$C_{60}$ carbocyclic group or a $C_1$-$C_{60}$ heterocyclic group.

In an embodiment, in Formula 3, CY3 may be a benzene group, a naphthalene group, an anthracene group, a dibenzothiophene group, a carbazole group, a fluorene group, or a dibenzosilole group, a dibenzofuran group, a cyclopentene group, a dihydrosilole group, a dihydropyrrole group, a dihydrofuran group, a dihydrothiophene group, a dihydroselenophene group, a dihydroindene group, a dihydrobenzosilole group, an indoline group, dihydrobenzofuran group, a dihydrobenzothiophene group, a dihydrobenzoselenophene group, a dihydrocyclopentapyridine group, a dihydrosilolepyridine group, a dihydropyrrolopyridine group, a dihydrofuranpyridine group, a dihydrothienopyridine group, a a dihydrocyclopentapyrimidine group, a dihydroselenophenopyridine group, dihydrosilolepyrimidine group, a dihydropyrrolopyrimidine group, a dihydrofuranpyrimidine group, a dihydrothienopyrimidine group, a dihydrosilolopyrimidine group, a dihydrocyclopentapyridazine group, a dihydrosilolepyridazine group, a dihydropyrrolopyridazine group, a dihydrofuranpyridazine group, a dihydrothienopyridazine group, a dihydroselenophenopyridazine group, a dihydrocyclopentapyrazine group, a dihydrosilolepyrazine group, a dihydropyrrolopyrazine group, a dihydrofuranpyrazine group, a dihydrothienopyrazine group, a dihydroselenophenopyrazine group, a dihydrocyclopentatriazine group, a dihydrosiloletriazine group, a dihydropyrrolotriazine group, a dihydrofurantriazine group, a dihydrothienotriazine group, or a dihydroselenophenotriazine group.

In an embodiment, CY3 may be a group represented by one of Formulae CY3-1 to CY3-4:

CY3-1

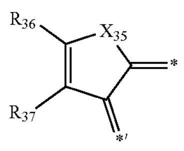

CY3-2

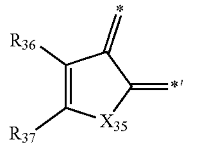

CY3-3

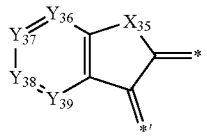

CY3-4

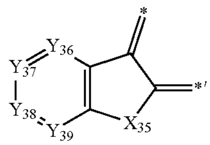

In Formulae CY3-1 to CY3-4, $X_{35}$ may be $C(R_{35a})(R_{35b})$, $Si(R_{35a})(R_{35b})$, $N(R_{35a})$, O, S, or Se.

In an embodiment, $X_{35}$ may be $Si(R_{35a})(R_{35b})$, $N(R_{35a})$, O, or S.

In embodiments, $X_{35}$ may be $Si(R_{35a})(R_{35b})$, O, or S.

In Formulae CY3-1 to CY3-4, $Y_{36}$ may be N or $C(R_{36})$, $Y_{37}$ may be N or $C(R_{37})$, $Y_{38}$ may be N or $C(R_{38})$, and $Y_{39}$ may be N or $C(R_{39})$.

In an embodiment, CY3 may be a group represented by one of Formulae CY3-1 to CY3-4, and when CY3 is a group represented by Formula CY3-3 or Formula CY3-4, at least one of Conditions 3-5 to 3-9 may be satisfied:

[Condition 3-5]

$Y_{36}$ may be N, $Y_{37}$ may be $C(R_{37})$, $Y_{38}$ may be $C(R_{38})$, and $Y_{39}$ may be $C(R_{39})$.

[Condition 3-6]

$Y_{37}$ may be N, $Y_{36}$ may be $C(R_{36})$, $Y_{38}$ may be $C(R_{38})$, and $Y_{39}$ may be $C(R_{39})$.

[Condition 3-7]

$Y_{38}$ may be N, $Y_{36}$ may be $C(R_{36})$, $Y_{37}$ may be $C(R_{37})$, and $Y_{39}$ may be $C(R_{39})$.

[Condition 2-8]

$Y_{39}$ may be N, $Y_{36}$ may be $C(R_{36})$, $Y_{37}$ may be $C(R_{37})$, and $Y_{38}$ may be $C(R_{38})$.

[Condition 2-9]

$Y_{36}$ may be $C(R_{36})$, $Y_{37}$ may be $C(R_{37})$, $Y_{38}$ may be $C(R_{38})$, and $Y_{39}$ may be $C(R_{39})$.

In Formulae CY3-1 to CY3-4, $R_{35a}$, $R_{35b}$, and $R_{36}$ to $R_{39}$ may each independently be the same as described in connection with $R_{31}$ in Formula 3.

In Formulae CY3-1 to CY3-4, * indicates a binding site to $Y_{31}$ in Formula 3, and *' indicates a binding site to $Y_{34}$ in Formula 3.

In embodiments, CY3 may be a group represented by Formula CY3-1 or Formula CY3-3.

In an embodiment, the first compound may include at least one of Compounds 1 to 3:

1

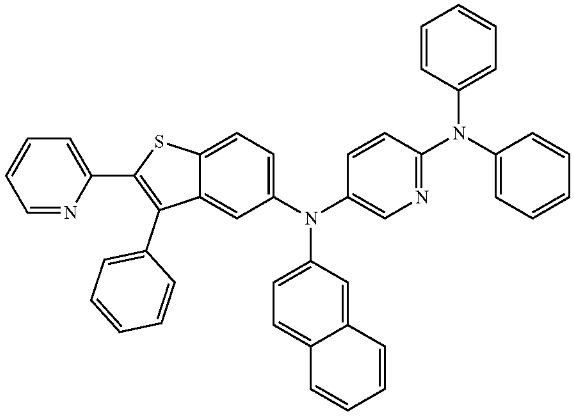

2

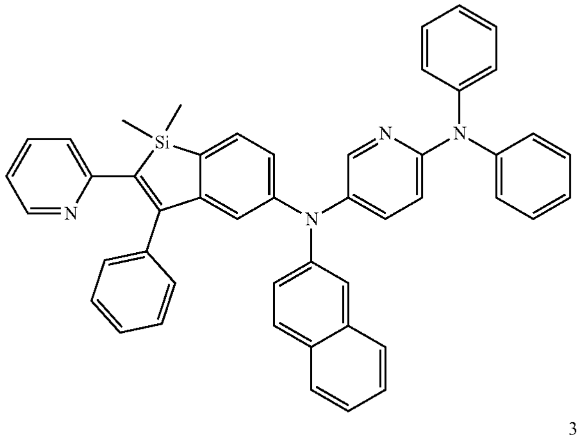

3

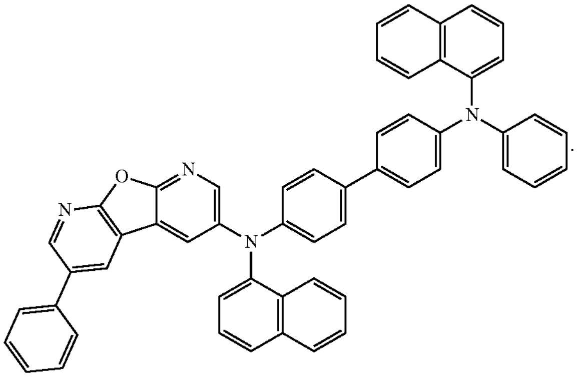

In Formula 2, $L_{21}$ to $L_{23}$ may each independently be a single bond, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$.

In embodiments, $L_{21}$ to $L_{23}$ may each independently be: a single bond; or a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a quinolinylene group, an isoquinolinylene group, a benzoquinolinylene group, a benzoisoquinolinylene group, a dibenzoquinolinylene group, a dibenzoisoquinolinylene group, a biphenylene group, a phenylpyridinylene group, a phenanthrolinylene group, a dibenzoquinolene group, a bipyridinylene group, or a pyridinylene group; or a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a quinolinylene group, an isoquinolinylene group, a benzoquinolinylene group, a benzoisoquinolinylene group, a dibenzoquinolinylene group, a dibenzoisoquinolinylene group, a biphenylene group, a phenylpyridinylene group, a phenanthrolene group, a bipyridinylene group, a dibenzoquinolene group, or a pyridinylene group, each unsubstituted or substituted with deuterium, —F, —Cl, —Br, —I, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a quinolinyl group, an isoquinolinyl group, a benzoquinolinyl group, a benzoisoquinolinyl group, a dibenzoquinolinyl group, a dibenzoisoquinolinyl group, a biphenyl group, a phenylpyridinyl group, a phenanthronyl group, a dibenzoquinol group, bipyridinyl group, a pyridinyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), —P(=O)($Q_{31}$)($Q_{32}$), or any combination thereof.

In embodiments, $L_{21}$ to $L_{23}$ may each independently be: a single bond; or a phenylene group, a naphthylene group, a spiro-anthracenefluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a thiophenylene group, a furanylene group, a carbazolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a quinolinylene group, an isoquinolinylene group, a benzoquinolinylene group, a benzoisoquinolinylene group, a dibenzoquinolinylene group, a dibenzoisoquinolinylene group, a biphenylene group, a phenylpyridinylene group, a phenanthrolinylene group, a dibenzoquinolene group, a bipyridinylene group, or a pyridinylene group; and a phenylene group, a naphthylene group, a spiro-anthracenefluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a thiophenylene group, a furanylene group, a carbazolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a quinolinylene group, an isoquinolinylene group, a benzoquinolinylene group, a benzoisoquinolinylene group, a dibenzoquinolinylene group, a dibenzoisoquinolinylene group, a biphenylene group, a phenylpyridinylene group, a phenanthrolinylene group, a dibenzoquinolene group, a bipyridinylene group, or a pyridinylene group, each unsubstituted or substituted with deuterium, —F, —Cl, —Br, —I, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, a spiro-anthracenefluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a thiophenyl group, a furanyl group, a carbazolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a quinolinyl group, an isoquinolinyl group, a benzoquinolinyl group, a benzoisoquinolinyl group, a dibenzoquinolinyl group, a dibenzoisoquinolinyl group, a biphenyl group, a phenylpyridinyl group, a phenanthrolinyl group, a dibenzoquinol group, bipyridinyl group, a pyridinyl group, or any combination thereof.

In embodiments, $L_{21}$ to $L_{23}$ may each independently be: a single bond; a phenylene group or a naphthylene group; or a phenylene group or a naphthylene group, each unsubstituted or substituted with deuterium, —F, —Cl, —Br, —I, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, or any combination thereof.

In embodiments, $L_1$ to $L_{23}$ may each independently be a single bond or a group represented by one of Formulae 5-1 to 5-9:

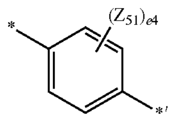
5-1

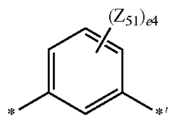
5-2

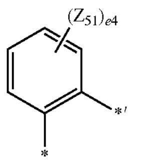
5-3

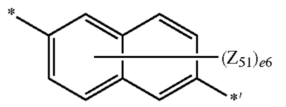
5-4

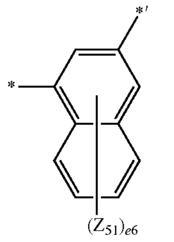
5-5

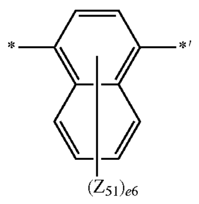
5-6

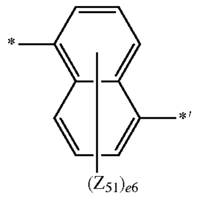
5-7

-continued 5-8

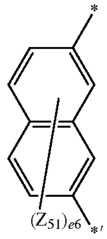

5-9

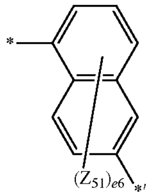

In Formulae 5-1 to 5-9, $Z_{51}$ may be the same as described in connection with $R_{21}$ in Formula 2, e4 may be an integer from 0 to 4, and e6 may be an integer from 0 to 6.

In Formulae 5-1 to 5-9, * and *' may each indicate a binding site to an adjacent atom.

In Formula 2, a21 to a23 may each independently be an integer from 0 to 3.

When a21 is 2 or greater, at least two $L_{21}$(s) may be identical to or different from each other. When a22 is 2 or greater, at least two $L_{22}$(s) may be identical to or different from each other. When a23 is 2 or greater, at least two $L_{23}$(s) may be identical to or different from each other.

In Formulae 1 to 3, $R_{21}$ to $R_{23}$ and $R_{31}$ may each independently be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_7$-$C_{60}$ aryl alkyl group unsubstituted or substituted with at least one $R_{10a}$, a $C_2$-$C_{60}$ heteroaryl alkyl group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$.

In embodiments, $R_{21}$ to $R_{23}$ and $R_{31}$ may each independently be: hydrogen, deuterium, —F, —Cl, —Br, —I, a hydroxyl group, a cyano group, a nitro group, a $C_1$-$C_{20}$ alkyl group, or a $C_1$-$C_{20}$ alkoxy group; a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a cyclopentyl group, a cyclohexyl group, a cycloheptyl group, a cyclooctyl group, an adamantanyl group, a ca norbornanyl group, a norbornenyl group, a cyclopentenyl group, a cyclohexenyl group, a cycloheptenyl group, a phenyl group, a biphenyl group, a terphenyl group, a naphthyl group, an anthracenyl group, a pyridinyl group, a pyrimidinyl group, a pyridazinyl group, a pyrazinyl group, a triazinyl group, a phenanthrenyl group, a quinolinyl group, an isoquinolinyl group, a spirobifluorenyl group, a dibenzothiophenyl group or any combination thereof; a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a spirobifluorenyl group, a phenanthrolinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, an azafluorenyl group, an azacarbazolyl group, an azadibenzofuranyl group, an azadibenzothiophenyl group, or an azadibenzosilolyl group, each unsubstituted or substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclooctyl group, an adamantanyl group, a norbornanyl group, a norbornenyl group, a cyclopentenyl group, a cyclohexenyl group, a cycloheptenyl group, a phenyl group, a biphenyl group, a terphenyl group, a $C_1$-$C_{20}$ alkylphenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a spirobifluorenyl group, a phenanthrolinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzofluorenyl group, a benzocarbazolyl group, a naphthobenzofuranyl group, a naphthobenzothiophenyl group, a naphthobenzosilolyl group, a dibenzofluorenyl group, a dibenzocarbazolyl group, a dinaphthofuranyl group, a dinaphthothiophenyl group, a dinaphthosilolyl group, an indenocarbazolyl group, an indolocarbazolyl group, a benzofuranocarbazolyl group, a benzothienocarbazolyl group, a benzosilolocarbazolyl group, an imidazopyridinyl group, an imidazopyrimidinyl group, $-Si(Q_{31})(Q_{32})(Q_{33})$, $-N(Q_{31})(Q_{32})$, $-B(Q_{31})(Q_{32})$, $-P(Q_{31})(Q_{32})$, $-C(=O)(Q_{31})$, $-S(=O)_2(Q_{31})$, $-P(=O)(Q_{31})(Q_{32})$, or any combination thereof; or $-Si(Q_1)(Q_2)(Q_3)$, $-N(Q_1)(Q_2)$, $-B(Q_1)(Q_2)$, $-C(=O)(Q_1)$, $-S(=O)_2(Q_1)$, or $-P(=O)(Q_1)(Q_2)$, wherein $Q_1$ to $Q_3$ and $Q_{31}$ to $Q_{33}$ may each independently be $-CH_3$, $-CD_3$, $-CD_2H$, $-CDH_2$, $-CH_2CH_3$, $-CH_2CD_3$, $-CH_2CD_2H$, $-CH_2CDH_2$, $-CHDCH_3$, $-CHDCD_2H$, $-CHDCDH_2$, $-CHDCD_3$, $-CD_2CD_3$, $-CD_2CD_2H$, or $-CD_2CDH_2$; or an n-propyl group, an iso-propyl group, an n-butyl group, an isobutyl group, a sec-butyl group, a tert-butyl group, an n-pentyl group, an isopentyl group, a sec-pentyl group, a tert-pentyl group, a phenyl group, a naphthyl group, an anthracenyl group, a pyridinyl group, a pyrimidinyl group, a pyridazinyl group, a pyrazinyl group, a triazinyl group, a phenanthrenyl group, a quinolinyl group, an isoquinolinyl group, a dibenzothiophenyl group, or a spirobifluorenyl group, each unsubstituted or substituted with deuterium, a $C_1$-$C_{20}$ alkyl group, a phenyl group, a biphenyl group, a pyridinyl group, a pyrimidinyl group, a pyridazinyl group, a pyrazinyl group, a triazinyl group, a naphthyl group, an anthracenyl group, a phenanthrenyl group, a quinolinyl group, an isoquinolinyl group, a spirobifluorenyl group a dibenzothiophenyl group, or any combination thereof.

In embodiments, $R_{21}$ to $R_{23}$ and $R_{31}$ may each independently be: hydrogen, deuterium, —F, or a cyano group; or a phenyl group, a biphenyl group, a naphthyl group, a pyridinyl group, a pyrimidinyl group, a pyridazinyl group, a pyrazinyl group, a triazinyl group, a quinolinyl group, an isoquinolinyl group, a naphthyl group, an anthracenyl group, a phenanthrenyl group, a dibenzothiophenyl group, or a spirobifluorenyl group, each unsubstituted or substituted with deuterium, —F, a cyano group, a $C_1$-$C_{20}$ alkyl group, a phenyl group, a biphenyl group, a naphthyl group, a pyridinyl group, a pyrimidinyl group, a pyridazinyl group, a pyrazinyl group, a triazinyl group, a quinolinyl group, an isoquinolinyl group, an anthracenyl group, a phenanthrenyl group, a $C_1$-$C_{20}$ alkylphenyl group, a dibenzothiophenyl group, a spirobifluorenyl group, or any combination thereof.

In embodiments, $R_{21}$ to $R_{23}$ and $R_{31}$ may each independently be hydrogen, deuterium, —F, or a cyano group; or a group represented by one of Formulae 4-1 to 4-34:

4-1

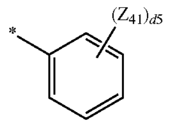

4-2

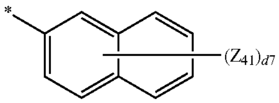

4-3

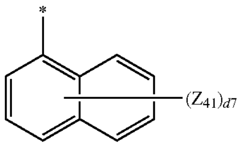

-continued 4-4

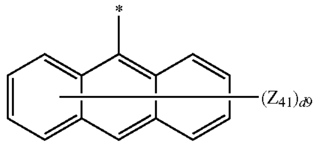

4-5

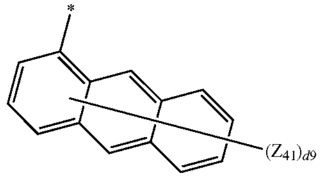

4-6

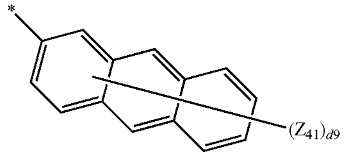

4-7

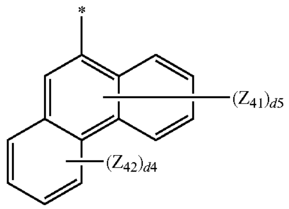

4-8

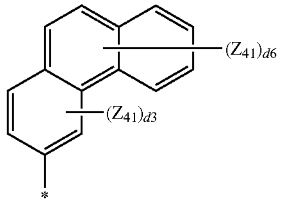

4-9

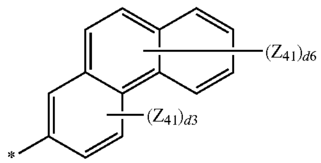

4-10

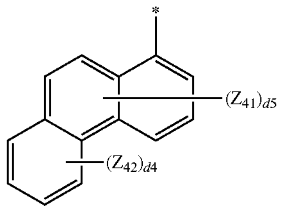

4-11

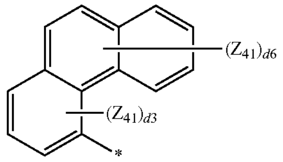

4-12

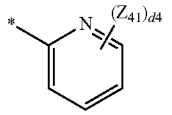

-continued
4-13
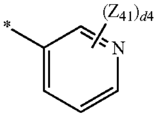
4-14
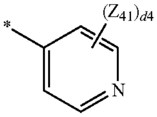
4-15
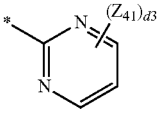
4-16
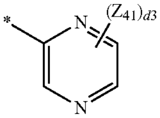
4-17
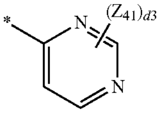
4-18
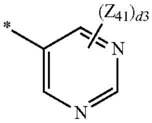
4-19
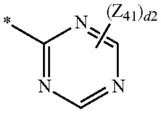
4-20
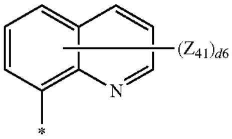
4-21
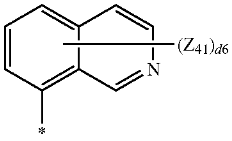
4-22
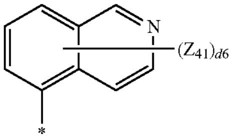
4-23
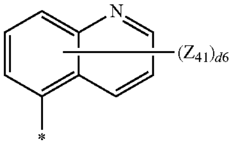
-continued
4-24
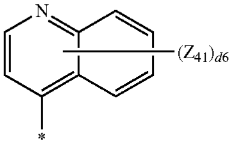
4-25
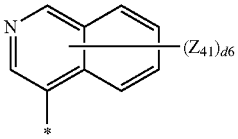
4-26
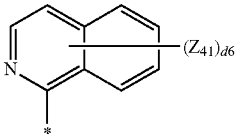
4-27
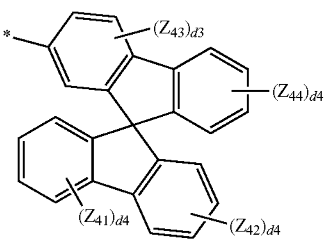
4-28
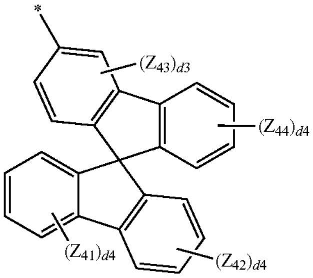
4-29
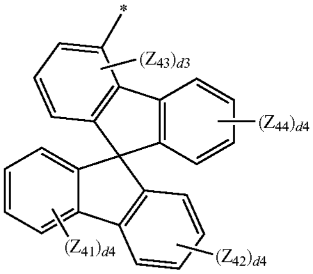
4-30
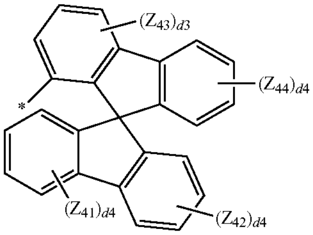

-continued 4-31

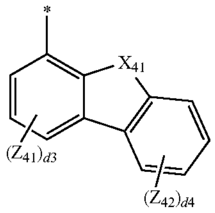

4-32

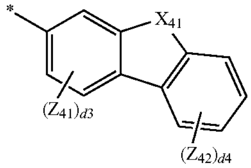

4-33

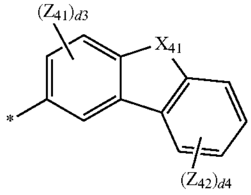

4-34

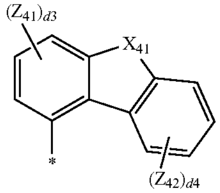

In Formulae 4-1 to 4-34, $X_{41}$ may be $C(R_{41a})(R_{41b})$, $Si(R_{41a})(R_{41b})$, $N(R_{41b})$, O, S, or Se.

In an embodiment, $X_{41}$ may be $Si(R_{41a})(R_{41b})$, O, or S.

In Formulae 4-1 to 4-34, $R_{41a}$, $R_{41b}$, and $Z_{41}$ to $Z_{44}$ may each independently be the same as described in connection with $R_{21}$ in Formula 2.

In Formulae 4-1 to 4-34, d2 may be an integer from 0 to 2, d3 may be an integer from 0 to 3, d4 may be an integer from 0 to 4, d5 may be an integer from 0 to 5, d6 may be an integer from 0 to 6, d7 may be an integer from 0 to 7, and d9 may be an integer from 0 to 9.

In Formulae 4-1 to 4-34, * indicates a binding site to an adjacent group.

In Formula 2, b21 to b23 may each independently be an integer from 0 to 10.

In an embodiment, the second compound may include at least one of Compounds 4 to 6:

4

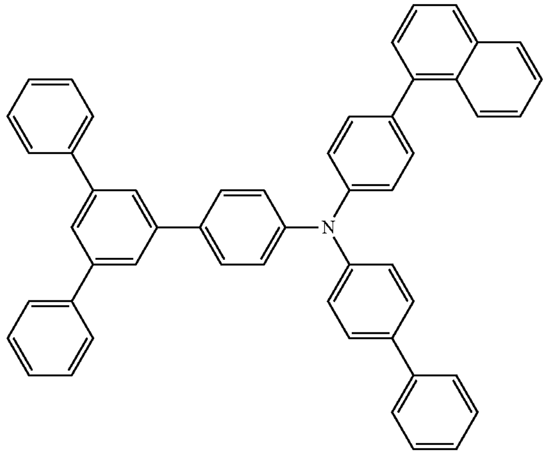

5

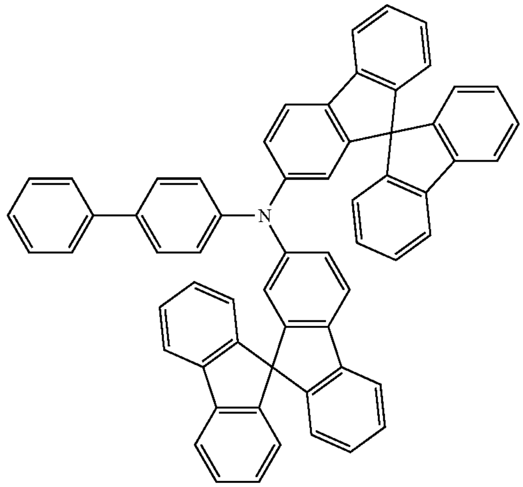

6

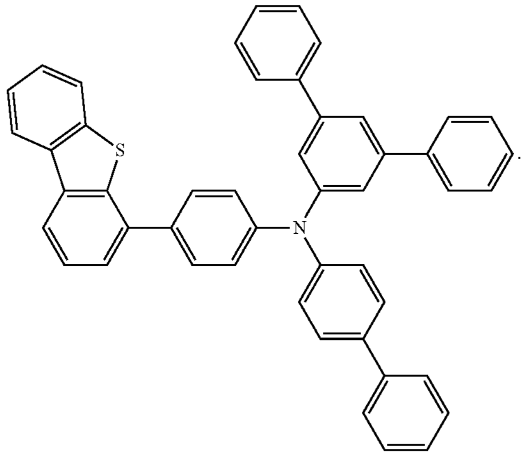

.

The first compound may be different from the second compound.

In an embodiment, the first compound and the second compound may each satisfy Equation 1-1:

$$E_{HOMO,EBL1} < E_{HOMO,EBL2} \quad \text{[Equation 1-1]}$$

In Equation 1-1, $E_{HOMO,\ EBL1}$ is an absolute value (eV) of a highest occupied molecular orbital (HOMO) energy level of the first compound, and $E_{HOMO,\ EBL2}$ is an absolute value (eV) of a HOMO energy level of the second compound.

In an embodiment, the first compound and the second compound may satisfy Equation 2-1:

$$0.01\ eV \le |E_{HOMO,EBL1} - E_{HOMO,EBL2}| \le 0.5\ eV \quad \text{[Equation 2-1]}$$

In Equation 2-1, $E_{HOMO,\ EBL1}$ and $E_{HOMO,\ EBL2}$ may respectively be understood by referring to the descriptions of $E_{HOMO,\ EBL1}$ and $E_{HOMO,\ EBL2}$ in Equation 1-1.

In an embodiment, $E_{HOMO,\ EBL1}$ and $E_{HOMO,\ EBL2}$ may each be evaluated using a density functional theory (DFT).

For example, $E_{HOMO,\ EBL1}$ and $E_{HOMO,\ EBL2}$ may be evaluated using a DFT according to Gaussian B3LYP. For example, a basis set of Gaussian B3LYP may be 6-31G*.

While not wishing to be bound by a theory, in a light-emitting device, wherein the first electron blocking layer may be between the second electron blocking layer and the first electrode, and the second electron blocking layer may be between the first electron blocking layer and the emission layer, and wherein the first electron blocking layer may include the first compound represented by Formula 1, the second electron blocking layer may include the second compound represented by Formula 2, as an absolute value (eV) of a HOMO energy level of the first compound may be smaller than an absolute value (eV) of a HOMO energy level of the second compound, as holes transmitted from the first electrode to the emission layer pass through the first compound and the second compound sequentially, in which the absolute values of the HOMO energy levels increase sequentially, migration efficiency of holes may be further improved, as compared with a light-emitting device having a same structure except that electron blocking layer may not be a double layer structure of a first electron blocking layer and a second electron blocking layer, the first electron blocking layer may not include the first compound, or the second electron blocking layer may not include the second compound. Accordingly, the driving voltage of a light-emitting device may be reduced, and luminescence efficiency of the light-emitting device may be improved, thus improving lifespan of the light-emitting device.

Therefore, luminescence efficiency and/or lifespan of an electronic device, e.g., a light-emitting device, including the first electron blocking layer and second electron blocking layer may be further improved.

Methods of synthesizing the compounds represented by Formulae 1 and 2 may be easily understood to those of ordinary skill in the art by referring to Synthesis Examples and Examples described herein.

In embodiments, the first electrode of the light-emitting device may be an anode, the second electrode of the light-emitting device may be a cathode, and the interlayer may further include a hole transport region between the first electrode and the emission layer and an electron transport region between the emission layer and the second electrode, wherein the hole transport region may include a hole injection layer, a hole transport layer, an emission auxiliary layer, or any combination thereof; and an electron blocking layer, and the electron transport region may include a buffer layer, a hole blocking layer, an electron control layer, an electron transport layer, or an electron injection layer.

In embodiments, the hole transport region may include a hole transport layer and the electron blocking layer.

The electron blocking layer may include the first electron blocking layer and the second electron blocking layer. The first electron blocking layer may include the first compound, and the second electron blocking layer may include the second compound.

The hole transport layer may be between the first electrode and the first electron blocking layer. The first electron blocking layer may be between the hole transport layer and the second electron blocking layer. The second electron blocking layer may be between the first electron blocking layer and the emission layer.

In an embodiment, the hole transport layer may include a third compound represented by Formula 201 or Formula 202, which are explained below.

In an embodiment, the first to third compounds may each satisfy Equations 1-1 and 1-2:

$$E_{HOMO,EBL1} < E_{HOMO,EBL2} \quad \text{[Equation 1-1]}$$

$$E_{HOMO,HTL} < E_{HOMO,EBL1} \quad \text{[Equation 1-2]}$$

In Equations 1-1 and 1-2, $E_{HOMO,\ EBL1}$ is an absolute value (eV) of a HOMO energy level of the first compound, $E_{HOMO,\ EBL2}$ is an absolute value (eV) of a HOMO energy level of the second compound, and $E_{HOMO,\ HTL}$ is an absolute value (eV) of a HOMO energy level of the third compound.

In an embodiment, $E_{HOMO,\ EBL1}$, $E_{HOMO,\ EBL2}$, and $E_{HOMO,\ HTL}$ may each be evaluated using a density functional theory (DFT).

In an embodiment, the first to third compounds may each satisfy Equations 2-1 and 2-2:

$$0.05\ eV \ge |E_{HOMO,EBL1} - E_{HOMO,EBL2}| \le 0.5\ eV \quad \text{[Equation 2-1]}$$

$$0.05\ eV \le |E_{HOMO,HTL} - E_{HOMO,EBL1}| \le 0.5\ eV \quad \text{[Equation 2-2]}$$

In Equations 2-1 and 2-2, $E_{HOMO,\ EBL1}$, $E_{HOMO,\ EBL2}$, and $E_{HOMO,\ HTL}$ may respectively be understood by referring to the descriptions of $E_{HOMO,\ EBL1}$, $E_{HOMO,\ EBL2}$, and $E_{HOMO,\ HTL}$ in Equations 1-1 and 1-2.

For example, $E_{HOMO,\ EBL1}$, $E_{HOMO,\ EBL2}$, and $E_{HOMO,\ HTL}$ may each be evaluated using a DFT according to Gaussian B3LYP. For example, a basis set of Gaussian B3LYP may be 6-31G*.

In embodiments, the emission layer may include a host and a dopant. For example, the dopant may include a phosphorescent dopant. For example, the phosphorescent dopant may include an organometallic compound. For example, the phosphorescent dopant may include platinum (Pt).

For example, a host included in the emission layer may include at least two different hosts.

In an embodiment, the host may include a fourth compound represented by Formula 301, which is explained below.

In an embodiment, the first compound, the second compound, and the fourth compound may each satisfy Equations 1-1 and 1-3:

$$E_{HOMO,EBL1} < E_{HOMO,EBL2} \quad \text{[Equation 1-1]}$$

$$E_{HOMO,EBL2} < E_{HOMO,HOST} \quad \text{[Equation 1-3]}$$

In Equations 1-1 and 1-3, $E_{HOMO,\ EBL1}$ is an absolute value (eV) of a HOMO energy level of the first compound, $E_{HOMO,\ EBL2}$ is an absolute value (eV) of a HOMO energy level of the second compound, and $E_{HOMO,\ HOST}$ is an absolute value (eV) of a HOMO energy level of the fourth compound.

In an embodiment, $E_{HOMO,\ EBL1}$, $E_{HOMO,\ EBL2}$, and $E_{HOMO,\ HOST}$ may each be evaluated using a density functional theory (DFT).

In an embodiment, the first compound, the second compound, and the fourth compound may each satisfy Equations 2-1 and 2-3:

$$0.05\ eV \le |E_{HOMO,EBL1} - E_{HOMO,EBL2}| \le 0.5\ eV \quad \text{[Equation 2-1]}$$

$$0.05\ eV \le |E_{HOMO,HOST} - E_{HOMO,EBL2}| \le 0.5\ eV \quad \text{[Equation 2-3]}$$

In Equations 2-1 and 2-3, $E_{HOMO,\ EBL1}$, $E_{HOMO,\ EBL2}$, and $E_{HOMO,\ HOST}$ may respectively be understood by referring to the descriptions of $E_{HOMO,\ EBL1}$, $E_{HOMO,\ EBL2}$, and $E_{HOMO,\ HOST}$ in Equations 1-1 and 1-3.

For example, $E_{HOMO,\ EBL1}$, $E_{HOMO,\ EBL2}$, and $E_{HOMO,\ HOST}$ may each be evaluated using a DFT according to Gaussian B3LYP. For example, a basis set of Gaussian B3LYP may be 6-31G*.

In embodiments, the light-emitting device may include a capping layer outside the first electrode and/or the second electrode.

As used herein, the expression that "(an electron blocking layer) includes a first compound represented by Formula 1 or a second compound represented by Formula 2" may be construed as meaning that "(the electron blocking layer) may include one compound represented by Formula 1 or one compound represented by Formula 2 or at least two different compounds represented by Formula 1 or Formula 2".

The term "interlayer" as used herein refers to a single layer and/or all layers located between a first electrode and a second electrode in a light-emitting device.

According to embodiments, an electronic apparatus may include the light-emitting device. The electronic apparatus may further include a thin-film transistor. In embodiments, the electronic apparatus may further include a thin-film transistor including a source electrode and drain electrode, and a first electrode of the light-emitting device may be electrically connected to at least one of the source electrode or the drain electrode. The electronic apparatus may further include a color filter, a color-conversion layer, a touchscreen layer, a polarization layer, or any combination thereof. The electronic apparatus may be understood by referring to the description of the electronic apparatus provided herein.

Description of FIG. 1

FIG. 1 is a schematic cross-sectional view of a light-emitting device 10 according to an embodiment. The light-emitting device 10 may include a first electrode 110, an interlayer 130, and a second electrode 150.

Hereinafter, the structure of the light-emitting device 10 according to an embodiment and a method of manufacturing the light-emitting device 10 according to an embodiment will be described in connection with FIG. 1.

[First Electrode 110]

In FIG. 1, a substrate may be further included under the first electrode 110 or above the second electrode 150. The substrate may be a glass substrate or a plastic substrate. The substrate may be a flexible substrate and may include plastics having excellent heat resistance and durability, for example, polyimide, polyethylene terephthalate (PET), polycarbonate, polyethylene naphthalate, polyarylate (PAR), polyetherimide, or any combination thereof.

The first electrode 110 may be formed by depositing or sputtering, on the substrate, a material for forming the first electrode 110. When the first electrode 110 is an anode, a high work function material that may easily inject holes may be used as a material for a first electrode.

The first electrode 110 may be a reflective electrode, a semi-transmissive electrode, or a transmissive electrode. When the first electrode 110 is a transmissive electrode, a material for forming the first electrode 110 may be indium tin oxide (ITO), indium zinc oxide (IZO), tin oxide ($SnO_2$), zinc oxide (ZnO), or any combinations thereof. In embodiments, when the first electrode 110 is a semi-transmissive electrode or a reflective electrode, magnesium (Mg), silver (Ag), aluminum (Al), aluminum-lithium (Al—Li), calcium (Ca), magnesium-indium (Mg—In), magnesium-silver (Mg—Ag), or any combination thereof may be used as a material for forming the first electrode 110.

The first electrode 110 may have a structure consisting of a single layer or a structure including two or more layers. In embodiments, the first electrode 110 may have a triple-layered structure of ITO/Ag/ITO.

[Interlayer 130]

The interlayer 130 may be on the first electrode 110. The interlayer 130 may include an emission layer.

The interlayer 130 may further include a hole transport region between the first electrode 110 and the emission layer and an electron transport region between the emission layer and the second electrode 150.

The interlayer 130 may further include metal-containing compounds such as organometallic compounds, inorganic materials such as quantum dots, and the like, in addition to various organic materials.

The interlayer 130 may include at least two emitting units sequentially stacked between the first electrode 110 and the second electrode 150; and at least one charge generation layer between the at least two emitting units. When the interlayer 130 includes the at least two emitting units and the at least one charge generation layer, the light-emitting device 10 may be a tandem light-emitting device.

[Hole Transport Region in Interlayer 130]

The hole transport region may have a structure consisting of a layer consisting of a single material, a structure consisting of a layer including different materials, or a multi-layered structure having layers including different materials.

The hole transport region may include a hole injection layer, a hole transport layer, an emission auxiliary layer, or any combination thereof, and the electron blocking layer.

For example, the hole transport region may have a multi-layered structure, e.g., a hole injection layer/hole transport layer/first electron blocking layer/second electron blocking layer structure, a hole injection layer/hole transport layer/first electron blocking layer/second electron blocking layer/emission auxiliary layer structure, a hole injection layer/first electron blocking layer/second electron blocking layer/emission auxiliary layer structure, a hole transport layer/first electron blocking layer/second electron blocking layer/emission auxiliary layer structure, or a hole injection layer/hole transport layer/first electron blocking layer/second electron blocking layer structure, wherein layers of each structure may be stacked on the first electrode 110 in its respective stated order, but embodiments are not limited thereto.

The hole transport region may include the compound represented by Formula 201, the compound represented by Formula 202, or any combination thereof:

[Formula 201]

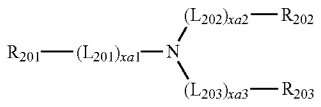

-continued

[Formula 202]

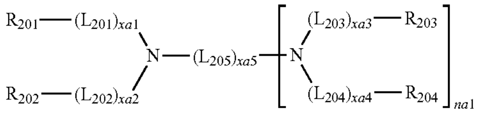

In Formulae 201 and 202, $L_{201}$ to $L_{204}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ may be *—O—**, *—S—**, *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, wherein * and *' each represent a binding site to a neighboring atom, xa1 to xa4 may each independently be an integer from 0 to 5, xa5 may be an integer from 1 to 10, $R_{201}$ to $R_{204}$ and $Q_{201}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ may optionally be bound to each other via a single bond, a $C_1$-$C_5$ alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group (e.g., a carbazole group or the like) unsubstituted or substituted with at least one $R_{10a}$ (e.g., Compound HT16 described herein), $R_{203}$ and $R_{204}$ may optionally be bound to each other via a single bond, a $C_1$-$C_5$alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group unsubstituted or substituted with at least one $R_{10a}$, and na1 may be an integer from 1 to 4.

In embodiments, Formulae 201 and 202 may each include at least one of groups represented by Formulae CY201 to CY217:

CY201

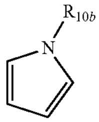

CY202

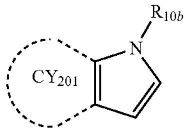

CY203

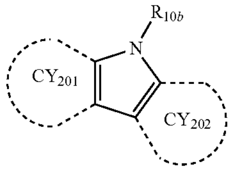

-continued

CY204

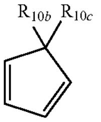

CY205

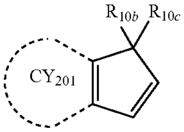

CY206

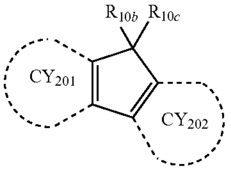

CY207

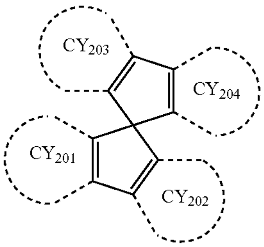

CY208

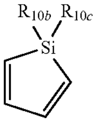

CY209

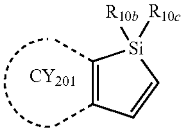

CY210

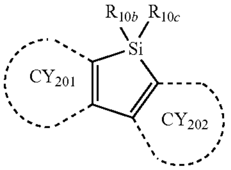

CY211

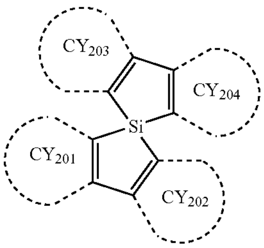

CY212

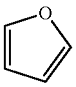

CY213

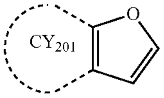

-continued

CY214

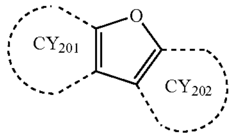

CY215

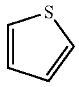

CY216

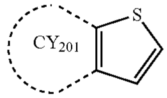

CY217

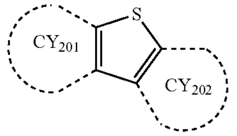

In Formulae CY201 to CY217, $R_{10b}$ and $R_{10c}$ may each independently be the same as described in connection with $R_{10a}$, ring CY201 to ring CY204 may each independently be a $C_3$-$C_{20}$ carbocyclic group or a $C_1$-$C_{20}$ heterocyclic group, and at least one hydrogen in Formulae CY201 to CY217 may be unsubstituted or substituted with $R_{10a}$.

In embodiments, in Formulae CY201 to CY217, ring CY201 to ring CY204 may each independently be a benzene group, a naphthalene group, a phenanthrene group, or an anthracene group.

In embodiments, Formulae 201 and 202 may each include at least one of groups represented by Formulae CY201 to CY203.

In embodiments, Formula 201 may include at least one of groups represented by Formulae CY201 to CY203 and at least one of groups represented by Formulae CY204 to CY217.

In embodiments, in Formula 201, xa1 may be 1, $R_{201}$ may be a group represented by any one of Formulae CY201 to CY203, xa2 may be 0, and $R_{202}$ may be a group represented by one of Formulae CY204 to CY207.

In embodiments, Formulae 201 and 202 may each not include groups represented by Formulae CY201 to CY203.

In embodiments, Formulae 201 and 202 may each not include groups represented by Formulae CY201 to CY203, and may include at least one of groups represented by Formulae CY204 to CY217.

In embodiments, Formulae 201 and 202 may each not include groups represented by Formulae CY201 to CY217.

In embodiments, the hole transport region may include one of Compounds HT1 to HT46, m-MTDATA, TDATA, 2-TNATA, NPB (NPD), β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphorsulfonic acid (PANI/CSA), polyaniline/poly(4-styrenesulfonate (PANI/PSS), or any combination thereof:

HT1

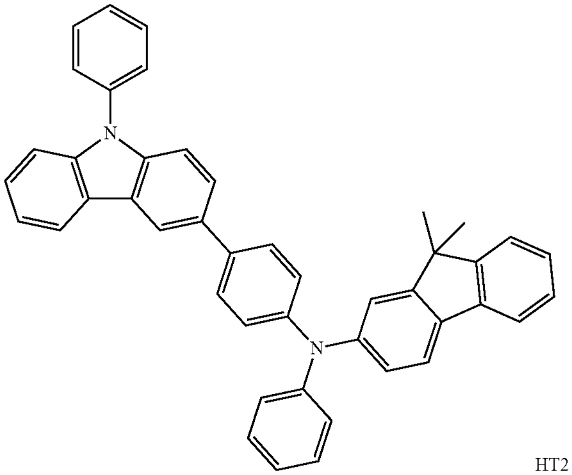

HT2

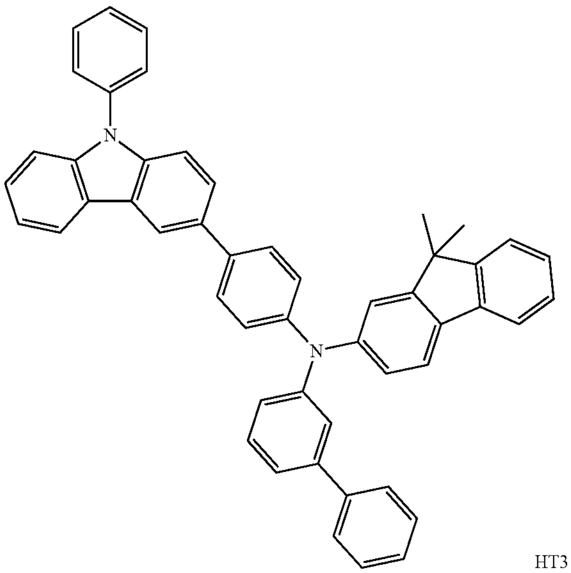

HT3

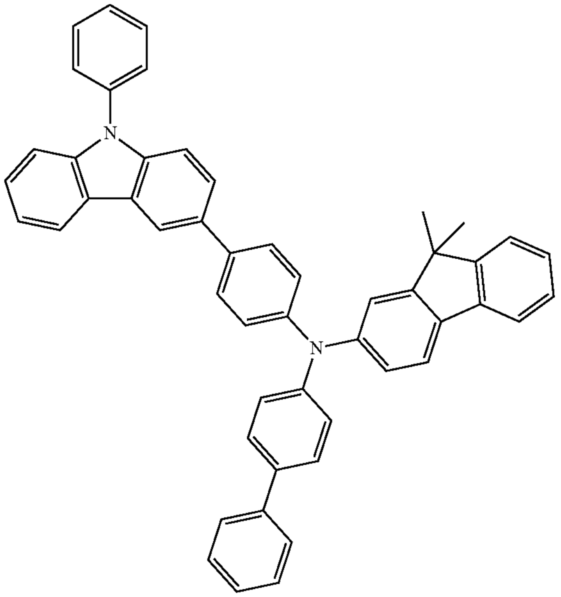

-continued
HT4
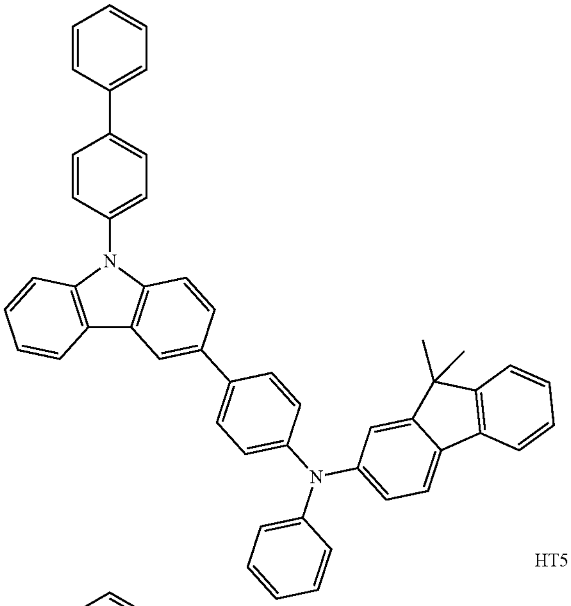
HT5
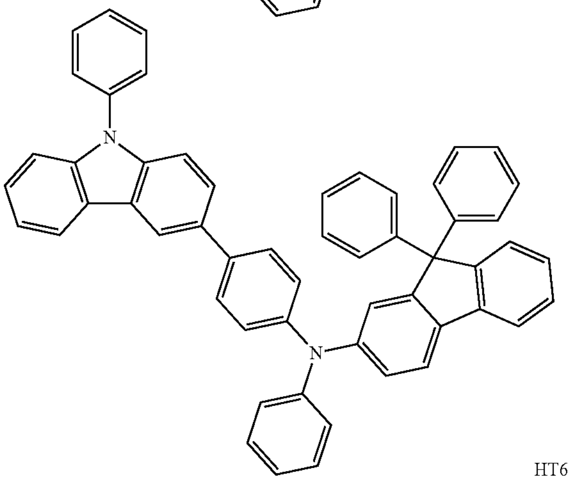
HT6
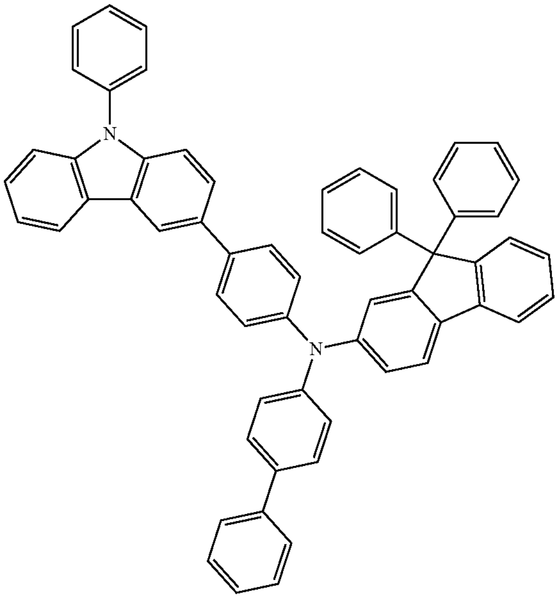
-continued
HT7
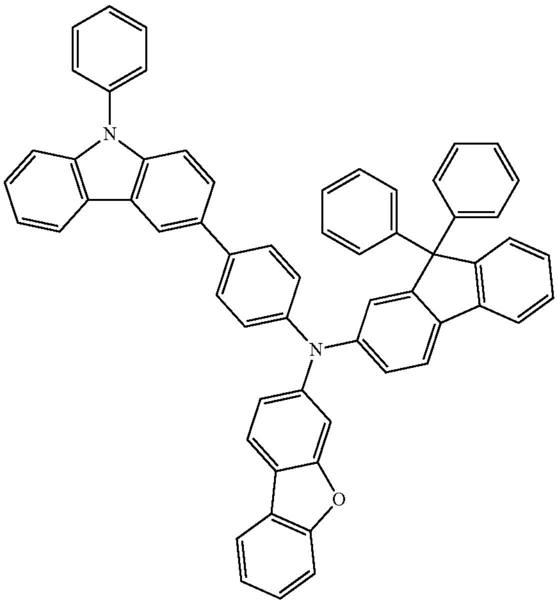
HT8
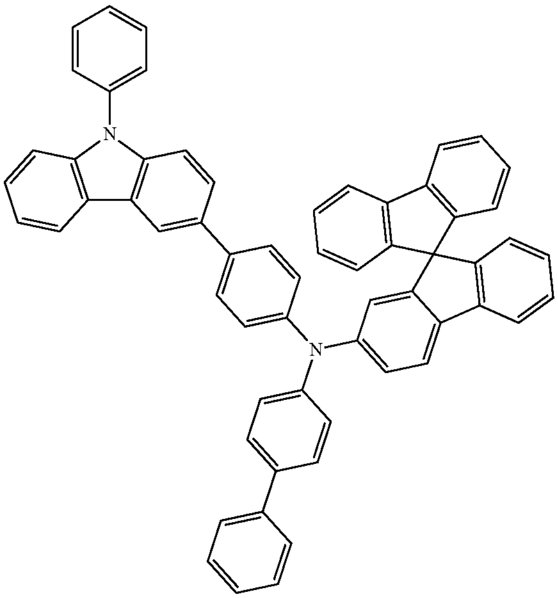

-continued
HT9
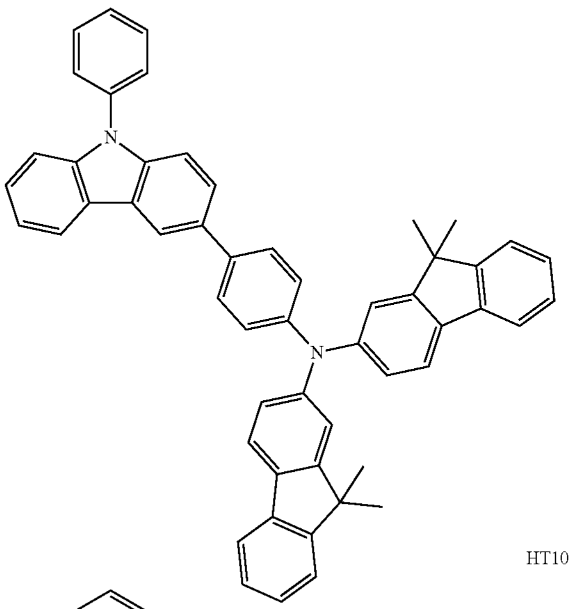
HT10
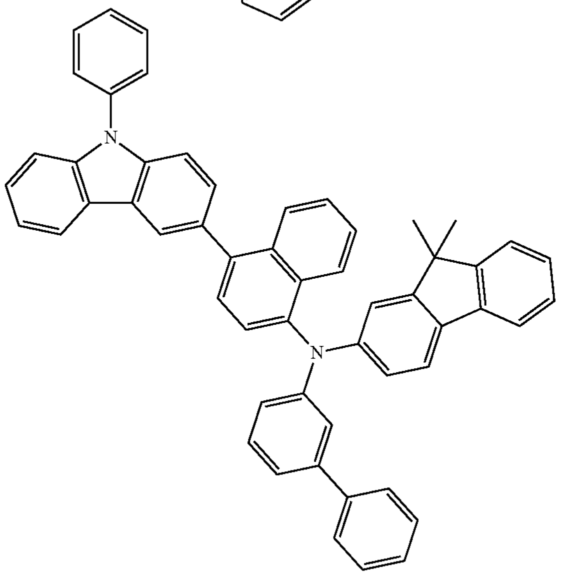
HT11
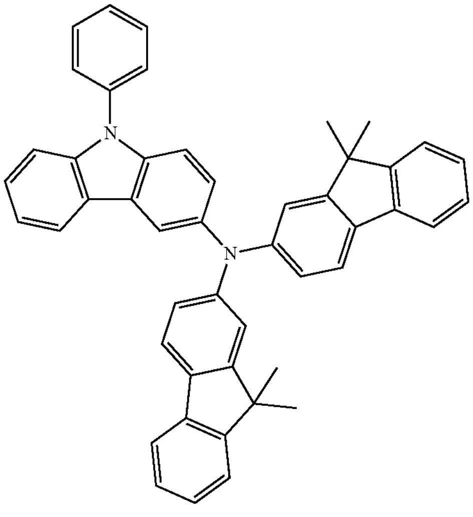
-continued
HT12
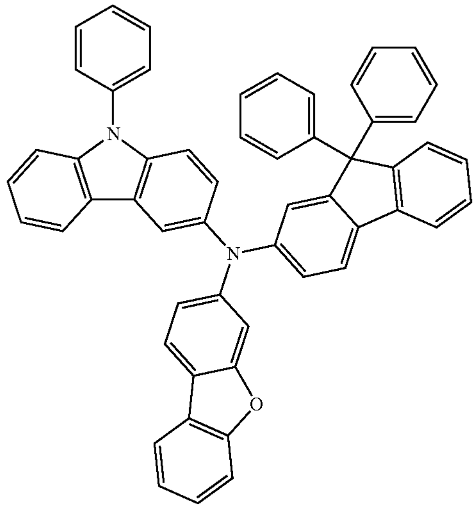
HT13
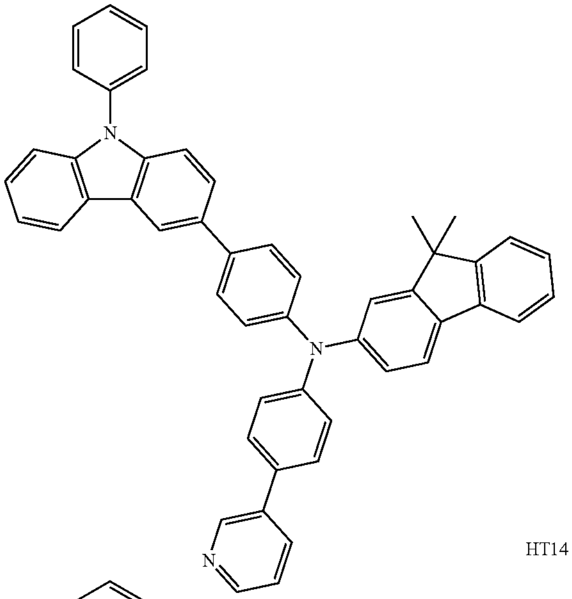
HT14
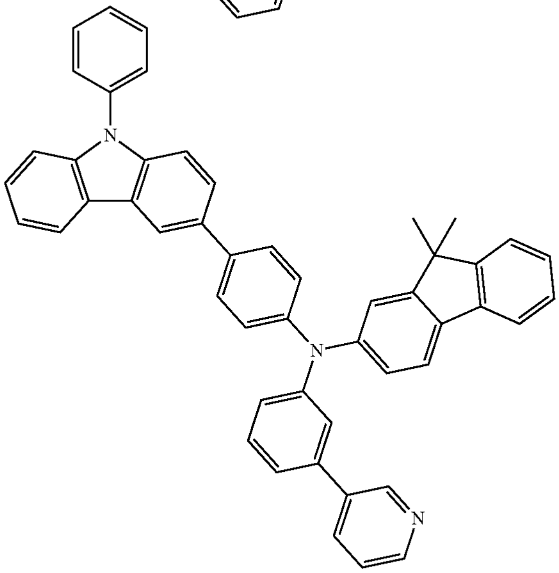

-continued
HT15
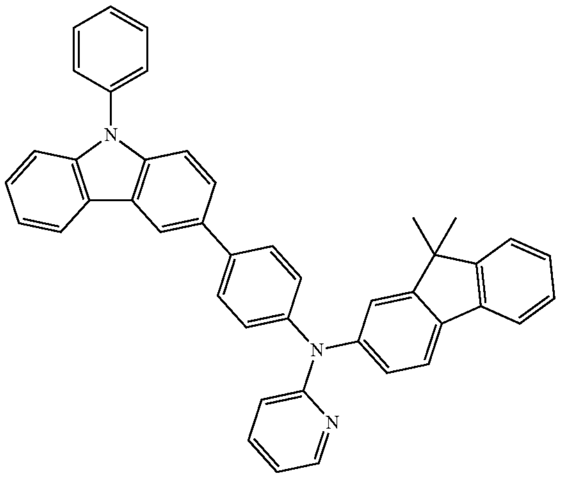
HT16
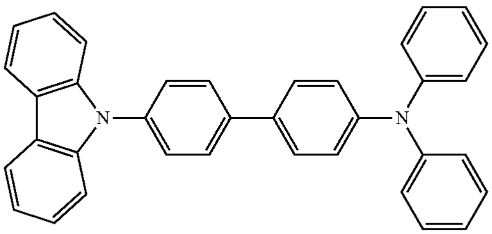
HT17
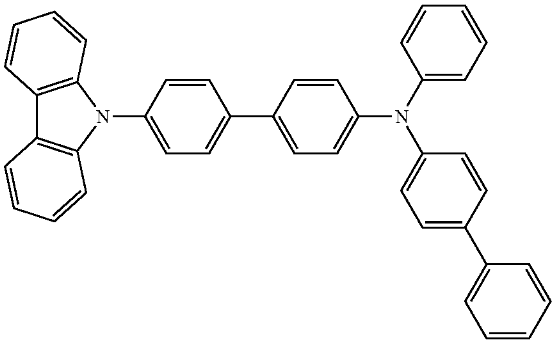
HT18
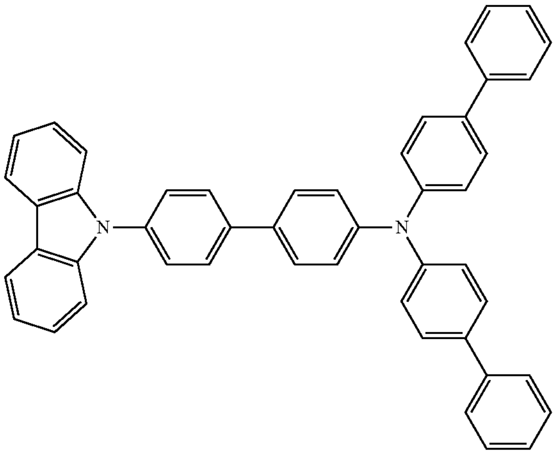
-continued
HT19
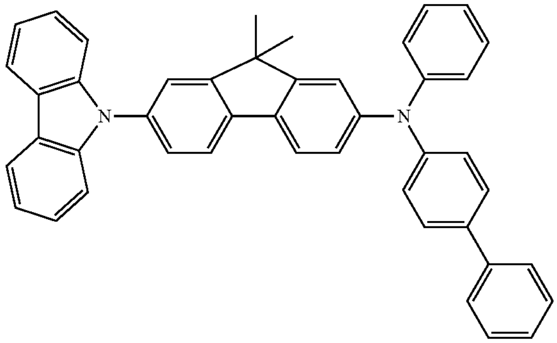
HT20
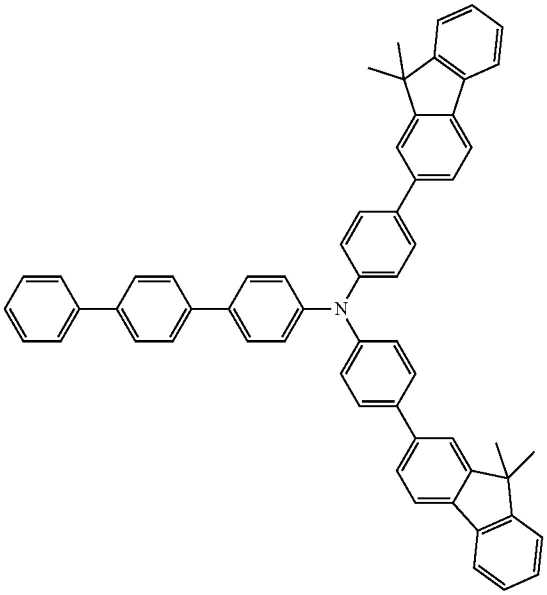
HT21
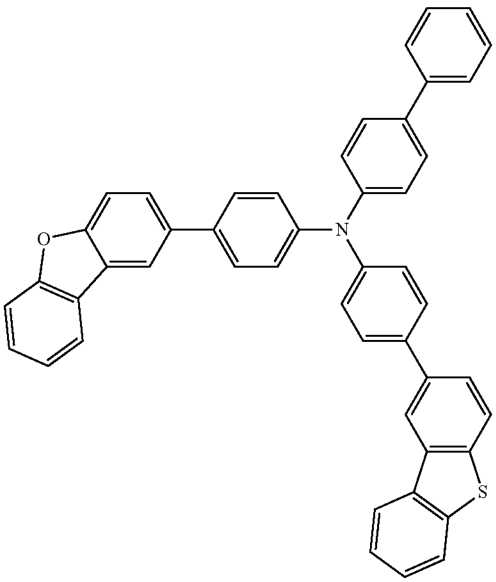

HT22
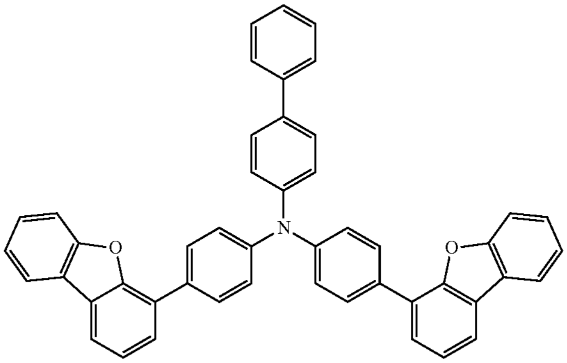
HT23
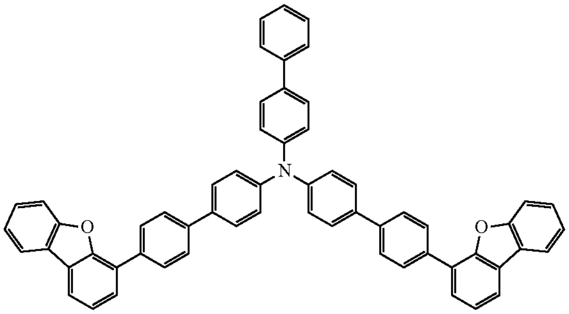
HT24
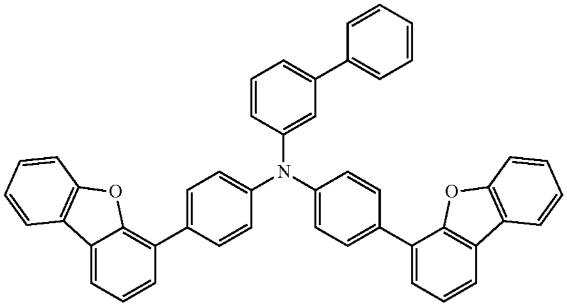
HT25
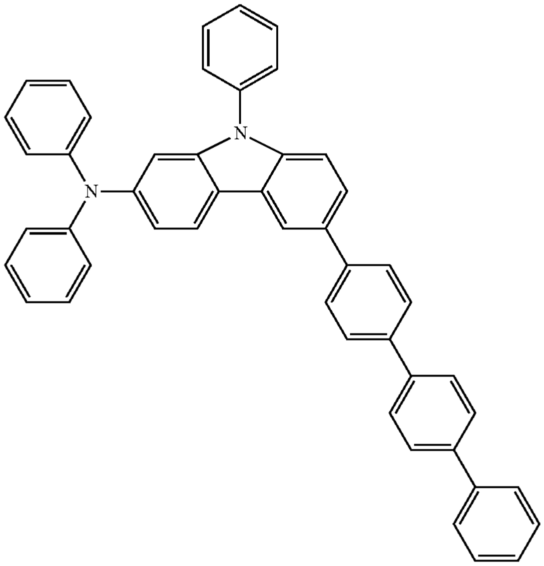
HT26
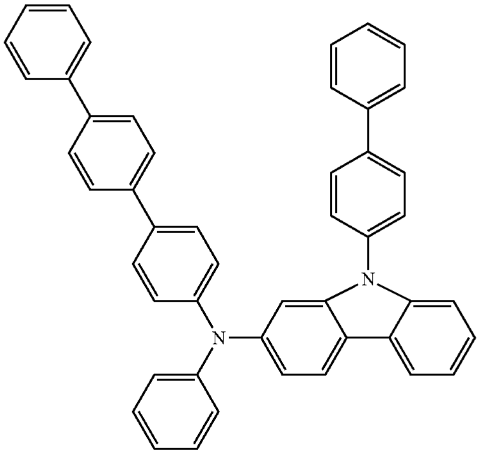
HT27
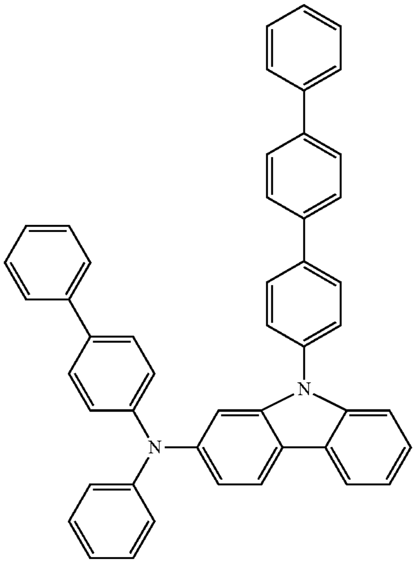
HT28
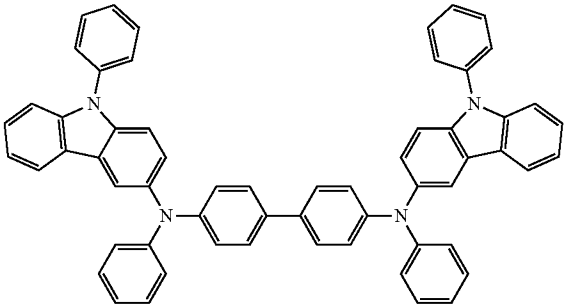

-continued
HT29
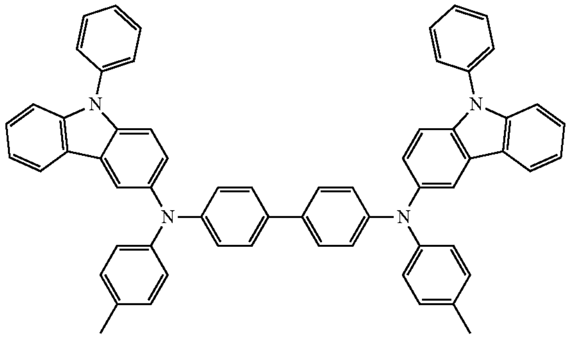
HT30
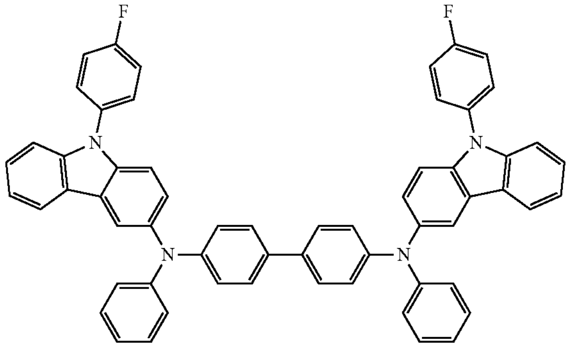
HT31
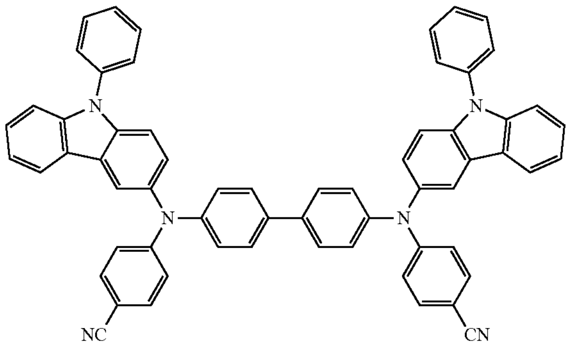
HT32
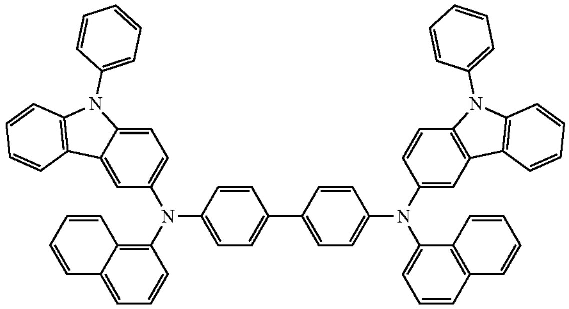
-continued
HT33
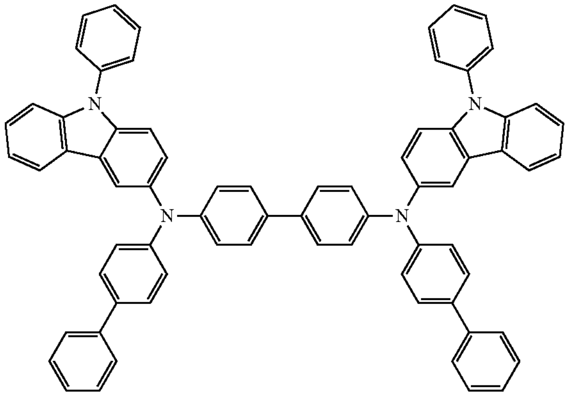
HT34
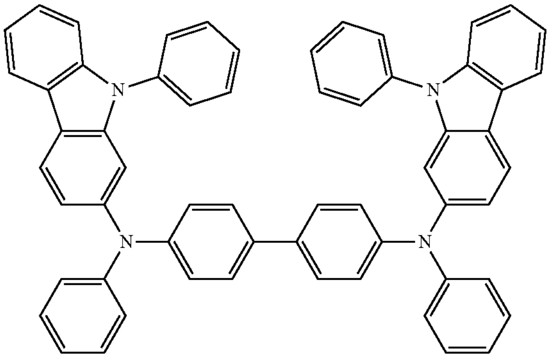
HT35
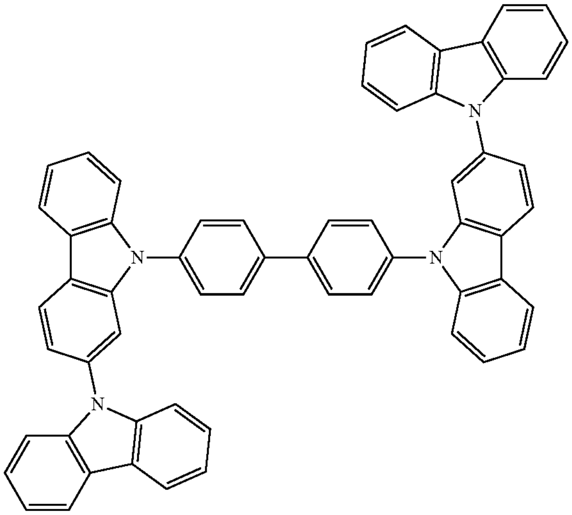

-continued
HT36
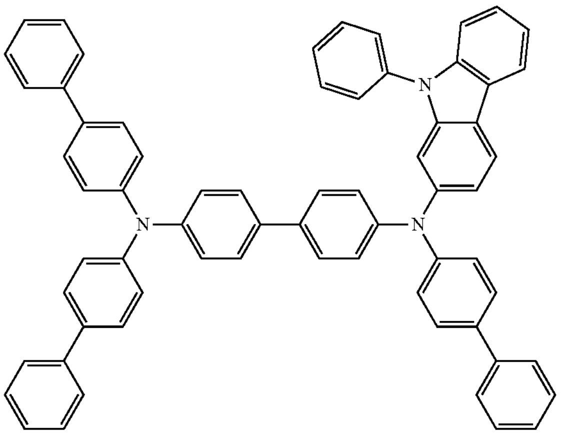
HT37
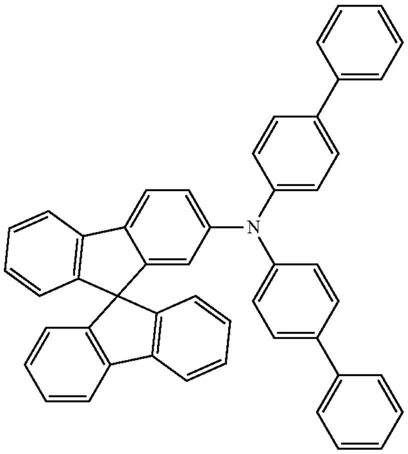
HT38
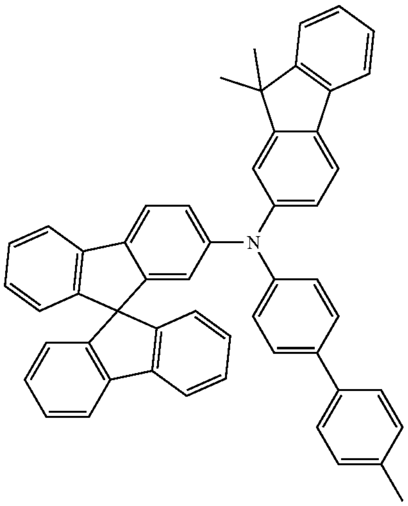
-continued
HT39
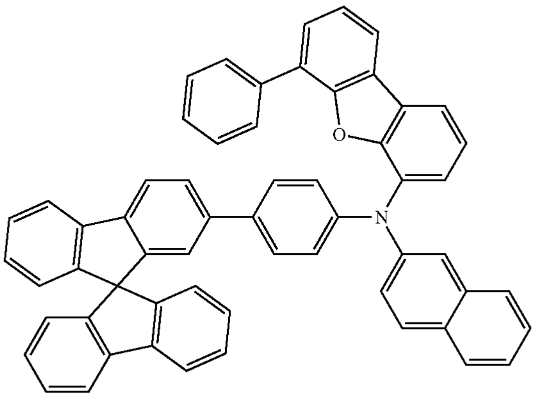
HT40
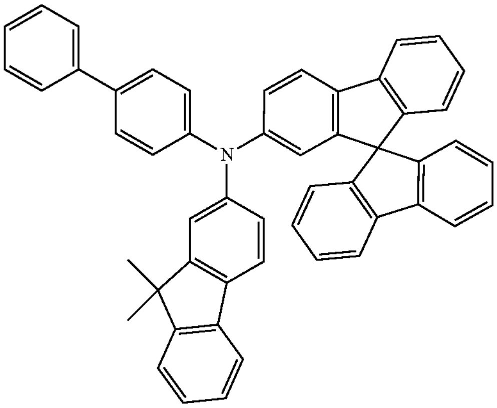
HT41
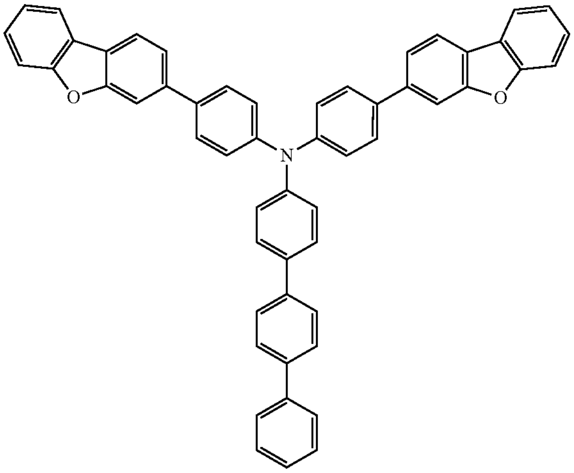
HT42
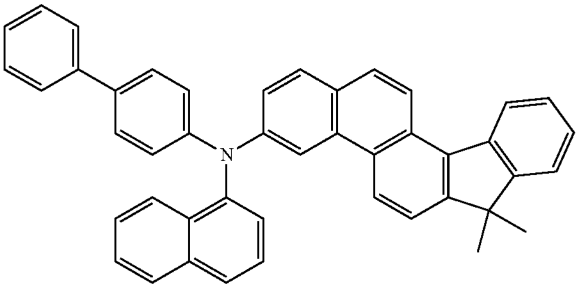

HT43
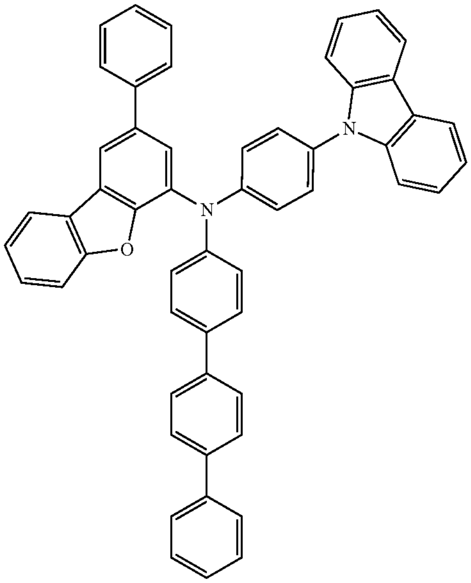
HT44
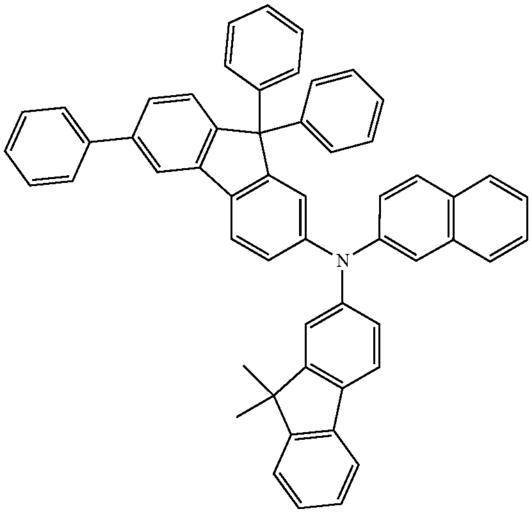
HT45
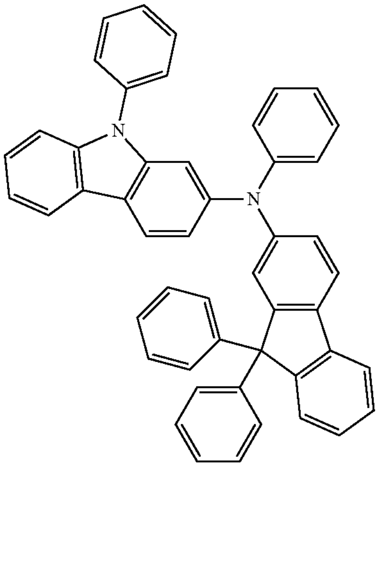
HT46
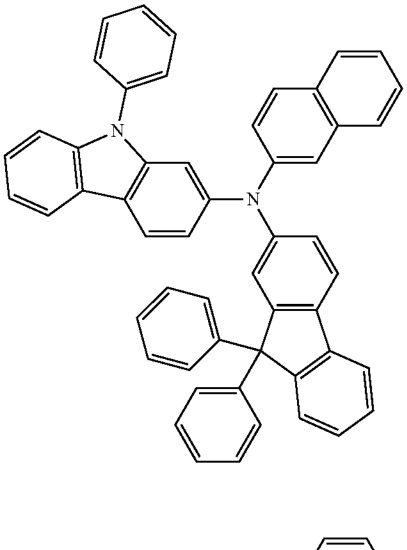
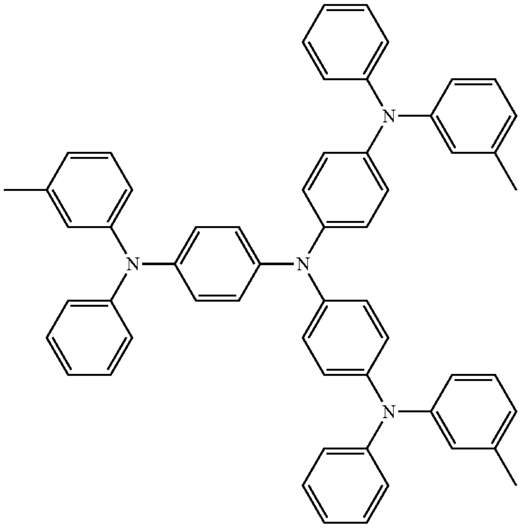
m-MTDATA
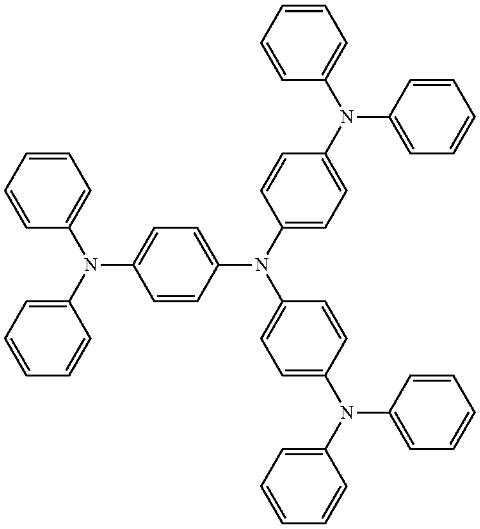
TDATA -continued
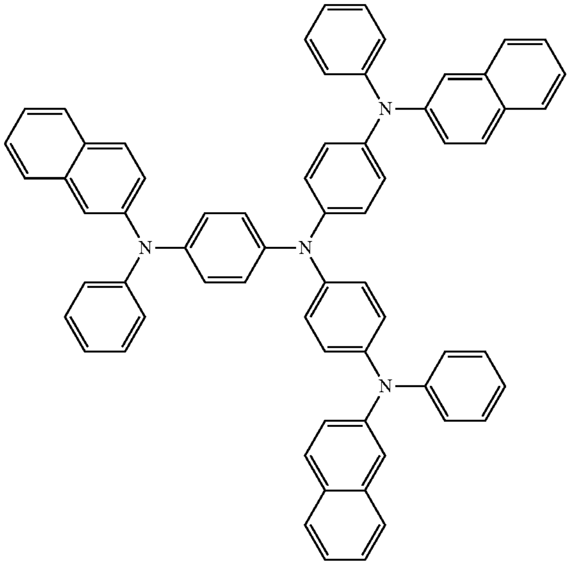
2-TNATA
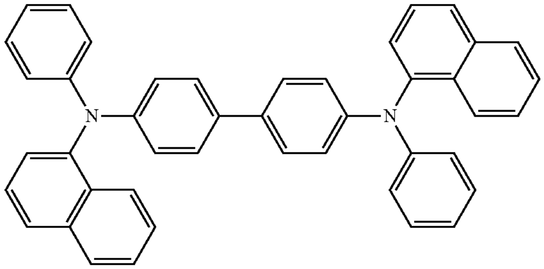
NPB
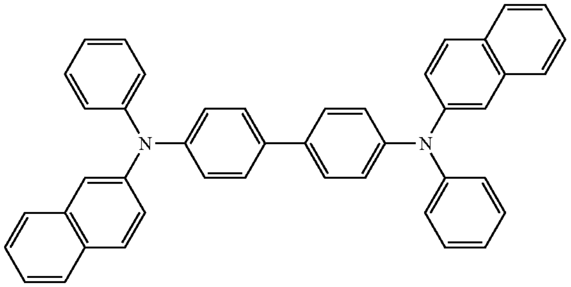
β-NPB
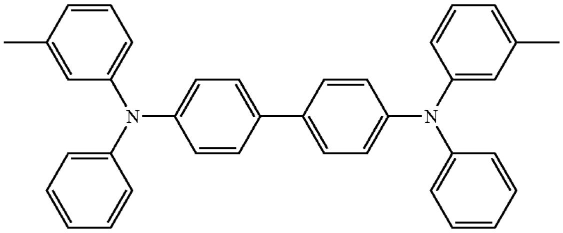
TPD
-continued
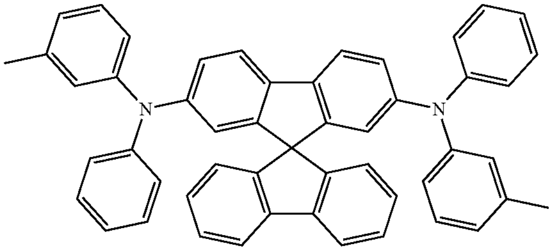
Spiro-TPD
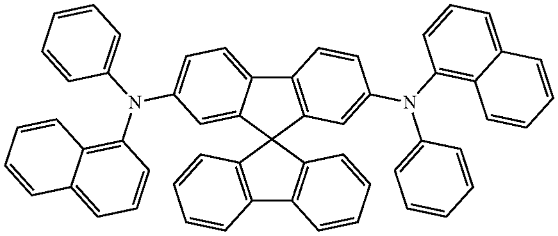
Spiro-NPB
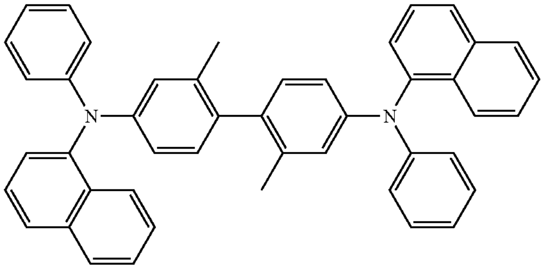
methylated-NPB
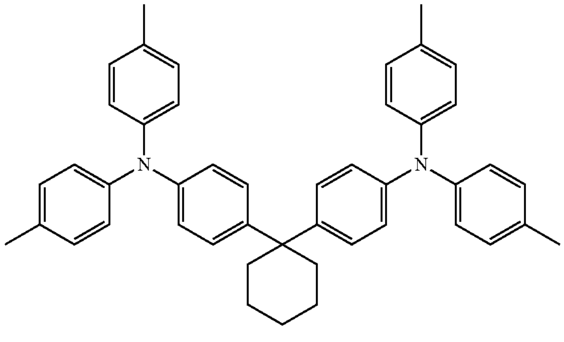
TAPC
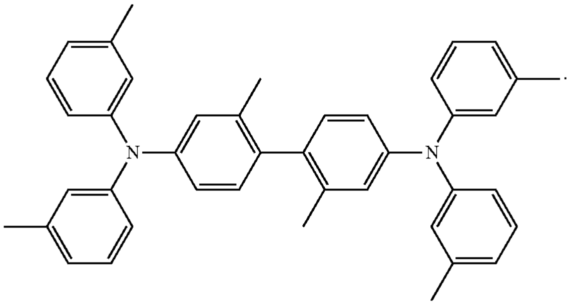
HMTPD
A thickness of the hole transport region may be in a range of about 50 Angstroms (Å) to about 10,000 Å. For example, the thickness of the hole transport region may be in a range of about 100 Å to about 4,000 Å.

When the hole transport region includes a hole injection layer, a hole transport layer, or any combination thereof, a thickness of the hole injection layer may be in a range of about 100 Å to about 9,000 Å, and a thickness of the hole transport layer may be in a range of about 50 Å to about 2,000 Å. For example, the thickness of the hole injection layer may be in a range of about 100 Å to about 1,000 Å. For example, the thickness of the hole transport layer may be in a range of about 100 Å to about 1,500 Å. When the thicknesses of the hole transport region, the hole injection layer, and the hole transport layer are within any of these ranges, excellent hole transport characteristics may be obtained without a substantial increase in driving voltage.

In an embodiment, a thickness of the first electron blocking layer may be in a range of about 5 Å to about 1,000 Å. For example, the thickness of the first electron blocking layer may be in a range of about 10 Å to about 600 Å. In an embodiment, a thickness of the second electron blocking layer may be in a range of about 1 Å to about 100 Å. For example, the thickness of the second electron blocking layer may be in a range of about 1 Å to about 50 Å. When the thickness of each of the first electron blocking layer and the second electron blocking layer is within any of these ranges, excellent hole transport characteristics may be obtained without a substantial increase in driving voltage.

In an embodiment, a ratio of a thickness of the second electron blocking layer to a thickness of the first electron blocking layer may be in a range of about 1 to about 10. For example, the ratio of a thickness of the second electron blocking layer to a thickness of the first electron blocking layer may be in a range of about 1 to about 8. For example, the ratio of a thickness of the second electron blocking layer to a thickness of the first electron blocking layer may be in a range of about 1 to about 6. When the ratio of a thickness of the second electron blocking layer to a thickness of the first electron blocking layer is within any of these ranges, excellent hole transport characteristics may be obtained without a substantial increase in driving voltage.

The emission auxiliary layer may increase light emission efficiency by compensating for an optical resonance distance according to a wavelength of light emitted by an emission layer. The electron blocking layer may prevent leakage of electrons to a hole transport region from the emission layer. Materials that may be included in the hole transport region may also be included in an emission auxiliary layer and an electron blocking layer.

[p-dopant]

The hole transport region may include a charge generating material as well as the aforementioned materials to improve conductive properties of the hole transport region. The charge generating material may be substantially homogeneously or non-homogeneously dispersed (for example, as a single layer consisting of charge generating material) in the hole transport region.

The charge generating material may include, for example, a p-dopant.

In embodiments, a lowest unoccupied molecular orbital (LUMO) energy level of the p-dopant may be equal to or less than about-3.5 eV.

In embodiments, the p-dopant may include a quinone derivative, a compound containing a cyano group, a compound containing element EL1 and element EL2, or any combination thereof.

Examples of the quinone derivative may include TCNQ, F4-TCNQ, and the like.

Examples of the compound containing a cyano group may include HAT-CN, a compound represented by Formula 221, and the like:

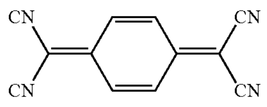

TCNQ

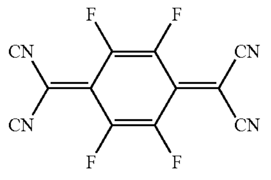

F4-TCNQ

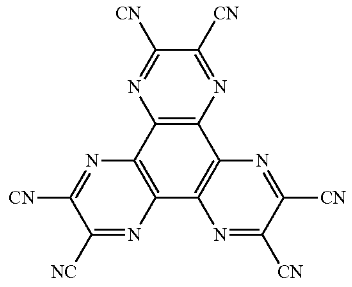

HAT-CN

[Formula 221]

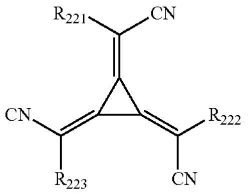

In Formula 221, $R_{221}$ to $R_{223}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, and at least one of $R_{221}$ to $R_{223}$ may each independently be: a $C_3$-$C_{60}$ carbocyclic group or a $C_1$-$C_{60}$ heterocyclic group, each substituted with a cyano group; —F; —Cl; —Br; —I; a $C_1$-$C_{20}$ alkyl group substituted with a cyano group, —F, —Cl, —Br, —I, or any combination thereof; or any combination thereof.

In the compound containing element EL1 and element EL2, element EL1 may be a metal, a metalloid, or a combination thereof, and element EL2 may be a non-metal, a metalloid, or a combination thereof.

Examples of the metal may include an alkali metal (e.g., lithium (Li), sodium (Na), potassium (K), rubidium (Rb), cesium (Cs), or the like); an alkaline earth metal (e.g., beryllium (Be), magnesium (Mg), calcium (Ca), strontium (Sr), barium (Ba), or the like); a transition metal (e.g., titanium (Ti), zirconium (Zr), hafnium (Hf), vanadium (V), niobium (Nb), tantalum (Ta), chromium (Cr), molybdenum (Mo), tungsten (W), manganese (Mn), technetium (Tc), rhenium (Re), iron (Fe), ruthenium (Ru), osmium (Os), cobalt (Co), rhodium (Rh), iridium (Ir), nickel (Ni), palladium (Pd), platinum (Pt), copper (Cu), silver (Ag), gold (Au), or the like); a post-transition metal (e.g., zinc (Zn), indium (In), tin (Sn), or the like); a lanthanide metal (e.g., lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), or the like); and the like.

Examples of the metalloid may include silicon (Si), antimony (Sb), tellurium (Te), and the like.

Examples of the non-metal may include oxygen (O), a halogen (e.g., F, Cl, Br, I, and the like), and the like.

For example, the compound containing element EL1 and element EL2 may include a metal oxide, a metal halide (e.g., metal fluoride, metal chloride, metal bromide, metal iodide, and the like), a metalloid halide (e.g., a metalloid fluoride, a metalloid chloride, a metalloid bromide, a metalloid iodide, and the like), a metal telluride, or any combination thereof.

Examples of the metal oxide may include tungsten oxide (e.g., WO, $W_2O_3$, $WO_2$, $WO_3$, $W_2O_5$, and the like), vanadium oxide (e.g., VO, $V_2O_3$, $VO_2$, $V_2O_5$, and the like), molybdenum oxide (MoO, $Mo_2O_3$, $MoO_2$, $MoO_3$, $Mo_2O_5$, and the like), rhenium oxide (e.g., $ReO_3$ and the like), and the like.

Examples of the metal halide may include an alkali metal halide, an alkaline earth metal halide, a transition metal halide, a post-transition metal halide, a lanthanide metal halide, and the like.

Examples of the alkali metal halide may include LiF, NaF, KF, RbF, CsF, LiCl, NaCl, KCl, RbCl, CsCl, LiBr, NaBr, KBr, RbBr, CsBr, LiI, NaI, KI, RbI, CsI, and the like.

Examples of the alkaline earth metal halide may include $BeF_2$, $MgF_2$, $CaF_2$, $SrF_2$, $BaF_2$, $BeCl_2$, $MgCl_2$, $CaCl_2$), $SrCl_2$, $BaCl_2$, $BeBr_2$, $MgBr_2$, $CaBr_2$, $SrBr_2$, $BaBr_2$, $BeI_2$, $MgI_2$, $CaI_2$, $SrI_2$, $BaI_2$, and the like.

Examples of the transition metal halide may include titanium halide (e.g., $TiF_4$, $TiCl_4$, $TiBr_4$, $TiI_4$, and the like), zirconium halide (e.g., $ZrF_4$, $ZrCl_4$, $ZrBr_4$, $ZrI_4$, and the like), hafnium halide (e.g., $HfF_4$, $HfCl_4$, $HfBr_4$, $HfI_4$, and the like), vanadium halide (e.g., $VF_3$, $VCl_3$, $VBr_3$, $VI_3$, and the like), niobium halide (e.g., $NbF_3$, $NbCl_3$, $NbBr_3$, $NbI_3$, and the like), tantalum halide (e.g., $TaF_3$, $TaCl_3$, $TaBr_3$, $TaI_3$, and the like), chromium halide (e.g., $CrF_3$, $CrCl_3$, $CrBr_3$, $CrI_3$, and the like), molybdenum halide (e.g., $MoF_3$, $MoCl_3$, $MoBr_3$, $MoI_3$, and the like), tungsten halide (e.g., $WF_3$, $WCl_3$, $WBr_3$, $WI_3$, and the like), manganese halide (e.g., $MnF_2$, $MnCl_2$, $MnBr_2$, $MnI_2$, and the like), technetium halide (e.g., $TcF_2$, $TcCl_2$, $TcBr_2$, $TcI_2$, and the like), rhenium halide (e.g., $ReF_2$, $ReCl_2$, $ReBr_2$, $ReI_2$, and the like), iron halide (e.g., $FeF_2$, $FeCl_2$, $FeBr_2$, $FeI_2$, and the like), ruthenium halide (e.g., $RuF_2$, $RuCl_2$, $RuBr_2$, $RuI_2$, and the like), osmium halide (e.g., $OsF_2$, $OsCl_2$, $OsBr_2$, $OsI_2$, and the like), cobalt halide (e.g., $CoF_2$, $CoCl_2$, $CoBr_2$, $CoI_2$, and the like), rhodium halide (e.g., $RhF_2$, $RhCl_2$, $RhBr_2$, $RhI_2$, and the like), iridium halide (e.g., $IrF_2$, $IrCl_2$, $IrBr_2$, $IrI_2$, and the like), nickel halide (e.g., $NiF_2$, $NiCl_2$, $NiBr_2$, $NiI_2$, and the like), palladium halide (e.g., $PdF_2$, $PdCl_2$, $PdBr_2$, $PdI_2$, and the like), platinum halide (e.g., $PtF_2$, $PtCl_2$, $PtBr_2$, $PtI_2$, and the like), copper halide (e.g., CuF, CuCl, CuBr, CuI, and the like), silver halide (e.g., AgF, AgCl, AgBr, AgI, and the like), gold halide (e.g., AuF, AuCl, AuBr, AuI, and the like), and the like.

Examples of the post-transition metal halide may include zinc halide (e.g., $ZnF_2$, $ZnCl_2$, $ZnBr_2$, $ZnI_2$, and the like), indium halide (e.g., $InI_3$ and the like), tin halide (e.g., $SnI_2$ and the like), and the like.

Examples of the lanthanide metal halide may include YbF, $YbF_2$, $YbF_3$, $SmF_3$, YbCl, $YbCl_2$, $YbCl_3$, $SmCl_3$, YbBr, $YbBr_2$, $YbBr_3$, $SmBr_3$, YbI, $YbI_2$, $YbI_3$, $SmI_3$, and the like.

Examples of the metalloid halide may include antimony halide (e.g., $SbCl_5$ and the like) and the like.

Examples of the metal telluride may include an alkali metal telluride (e.g., $Li_2Te$, $Na_2Te$, $K_2Te$, $Rb_2Te$, $Cs_2Te$, and the like), an alkaline earth metal telluride (e.g., BeTe, MgTe, CaTe, SrTe, BaTe, and the like), a transition metal telluride (e.g., $TiTe_2$, $ZrTe_2$, $HfTe_2$, $V_2Te_3$, $Nb_2Te_3$, $Ta_2Te_3$, $Cr_2Te_3$, $Mo_2Te_3$, $W_2Te_3$, MnTe, TcTe, ReTe, FeTe, RuTe, OsTe, CoTe, RhTe, IrTe, NiTe, PdTe, PtTe, $Cu_2Te$, CuTe, $Ag_2Te$, AgTe, $Au_2Te$, and the like), a post-transition metal telluride (e.g., ZnTe and the like), a lanthanide metal telluride (e.g., LaTe, CeTe, PrTe, NdTe, PmTe, EuTe, GdTe, TbTe, DyTe, HoTe, ErTe, TmTe, YbTe, LuTe, and the like), and the like.

[Emission Layer in Interlayer 130]

When the light-emitting device 10 is a full color light-emitting device, the emission layer may be patterned into a red emission layer, a green emission layer, and/or a blue emission layer, according to a subpixel. In embodiments, the emission layer may have a stacked structure. The stacked structure may include two or more layers selected from a red emission layer, a green emission layer, and a blue emission layer. The two or more layers may directly contact each other. In embodiments, the two or more layers may be separated from each other. In embodiments, the emission layer may include two or more materials. The two or more materials may include a red light-emitting material, a green light-emitting material, or a blue light-emitting material. The two or more materials may be mixed with each other in a single layer. The two or more materials mixed with each other in the single layer may emit white light. In embodiments, the emission layer may emit blue light.

In embodiments, the emission layer may include the compound represented by Formula 1 described herein.

The emission layer may include a host and a dopant.

In embodiments, the dopant may include the compound represented by Formula 1 described herein. The dopant may include, in addition to the compound represented by Formula 1, a phosphorescent dopant, a fluorescent dopant, or any combination thereof. The phosphorescent dopant or the fluorescent dopant that may be included in the emission layer may be understood by referring to the descriptions of the phosphorescent dopant or the fluorescent dopant.

An amount of the dopant in the emission layer may be in a range of about 0.01 parts by weight to about 15 parts by weight, based on 100 parts by weight of the host.

In embodiments, the emission layer may include a quantum dot.

The emission layer may include a delayed fluorescence material. The delayed fluorescence material may serve as a host or a dopant in the emission layer.

A thickness of the emission layer may be in a range of about 100 Å to about 1,000 Å. For example, the thickness of the emission layer may be in a range of about 200 Å to about 600 Å. When the thickness of the emission layer is within any of these ranges, improved luminescence characteristics may be obtained without a substantial increase in driving voltage.

[Host]

The host may include, for example, a carbazole-containing compound, an anthracene-containing compound, a triazine-containing compound, or any combination thereof. The host may include, for example, a carbazole-containing compound and a triazine-containing compound.

In embodiments, the host may include the compound represented by Formula 301:

$$[Ar_{301}]_{xb11}\text{-}[(L_{301})_{xb1}\text{-}R_{301}]_{xb21} \quad \text{[Formula 301]}$$

In Formula 301, $Ar_{301}$ and $L_{301}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 may be 1, 2, or 3, xb1 may be an integer from 0 to 5, $R_{301}$ may be hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), xb21 may be an integer from 1 to 5, and $Q_{301}$ to $Q_{303}$ may each independently be the same as defined in connection with $Q_1$ provided herein.

In embodiments, when xb11 in Formula 301 is 2 or greater, at least two $Ar_{301}$(s) may be bound via a single bond.

In embodiments, the host may include a compound represented by Formula 301-1, a compound represented by Formula 301-2, or any combination thereof:

$L_{302}$ to $L_{304}$ may each independently be the same as described in connection with $L_{301}$ provided herein, xb2 to xb4 may each independently be the same as described in connection with xb1 provided herein, and $R_{302}$ to $R_{305}$ and $R_{311}$ to $R_{314}$ may each independently be the same as described in connection with $R_{301}$ provided herein.

In embodiments, the host may include an alkaline earth-metal complex, a post-transitional metal complex, or any combination thereof. For example, the host may include a Be complex (e.g., Compound H55), a Mg complex, a Zn complex, or any combination thereof.

In embodiments, the host may include at least one of Compounds H1 to H139, 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri (carbazol-9-yl)benzene (TCP), or any combination thereof:

[Formula 301-1]

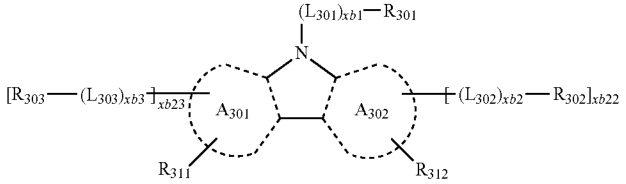

[Formula 301-2]

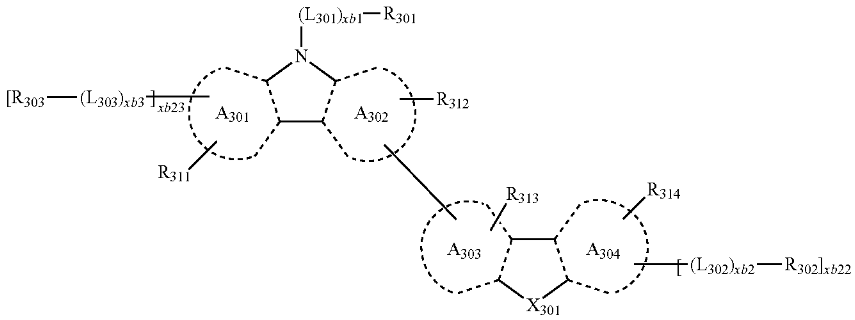

In Formulae 301-1 to 301-2, ring $A_{301}$ to ring $A_{304}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $X_{301}$ may be O, S, N—[($L_{304}$)$_{xb4}$-$R_{304}$], C($R_{304}$)($R_{305}$), or Si($R_{304}$)($R_{305}$), xb22 and xb23 may each independently be 0, 1, or 2, $L_{301}$, xb1, and $R_{301}$ may respectively be the same as described in connection with $L_{301}$, xb1, and $R_{301}$ provided herein,

H1

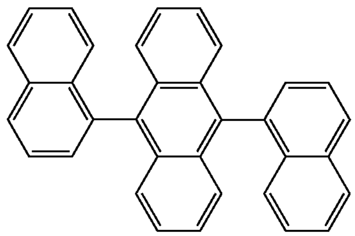

-continued
H2
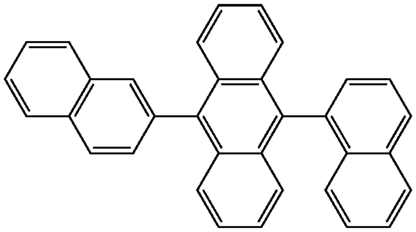
H3
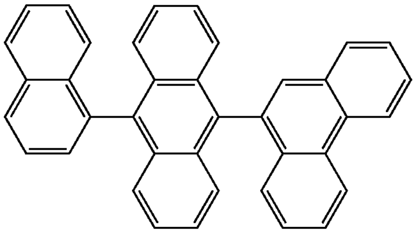
H4
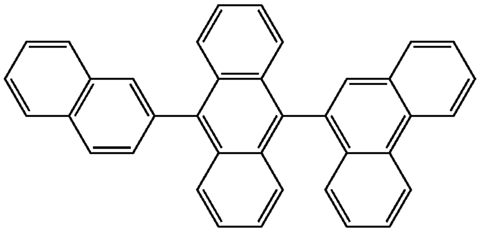
H5
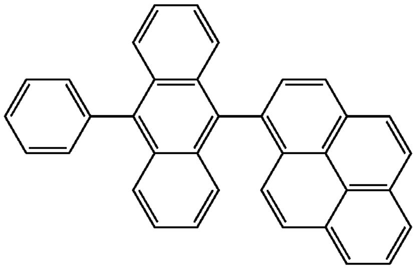
H6
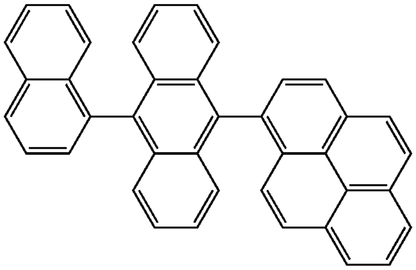
H7
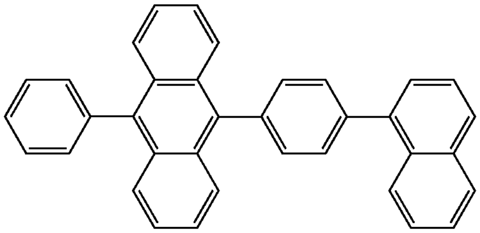
-continued
H8
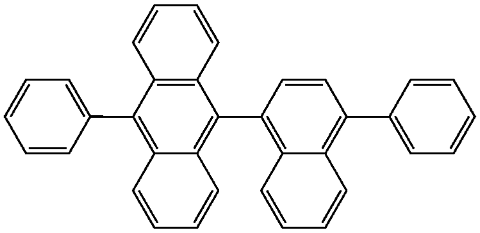
H9
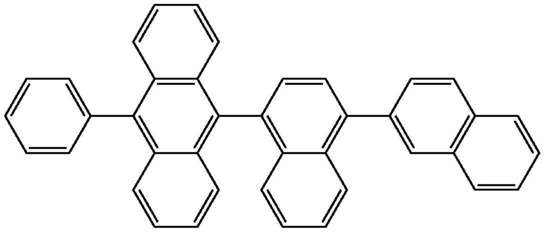
H10
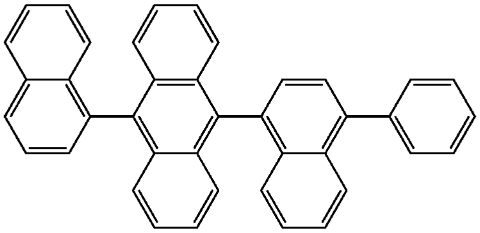
H11
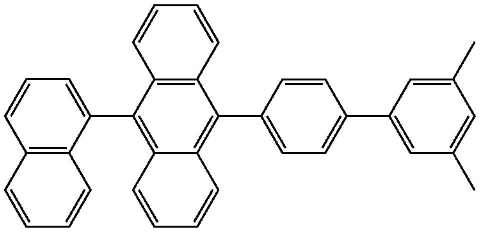
H12
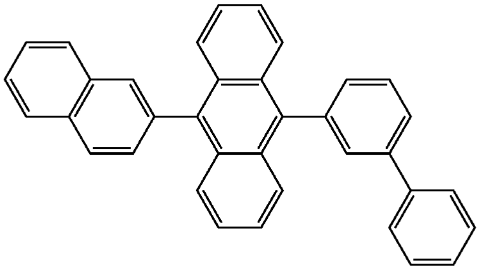
H13
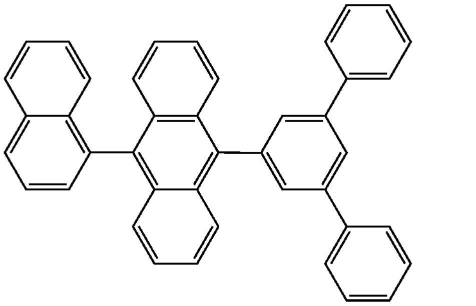

-continued
H14
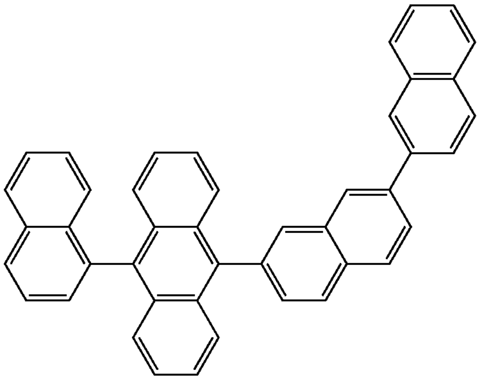
H15
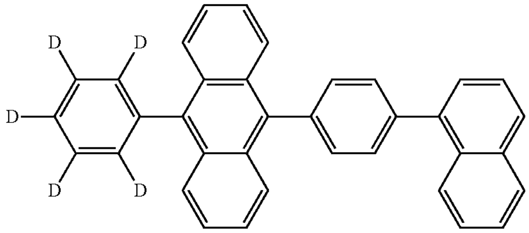
H16
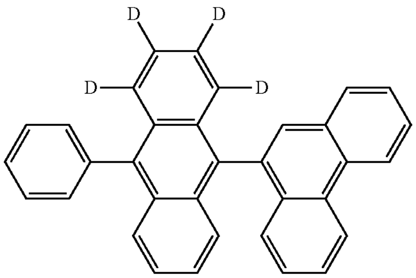
H17
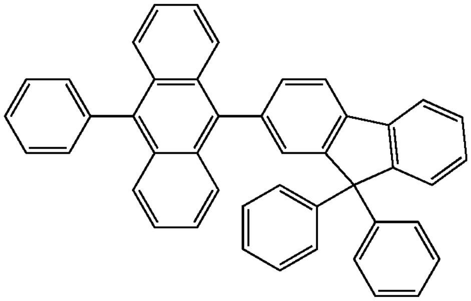
H18
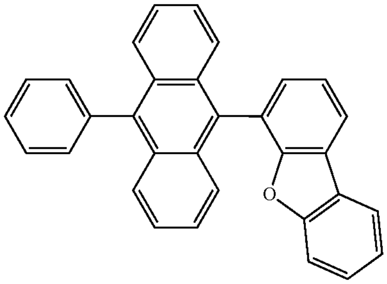
-continued
H19
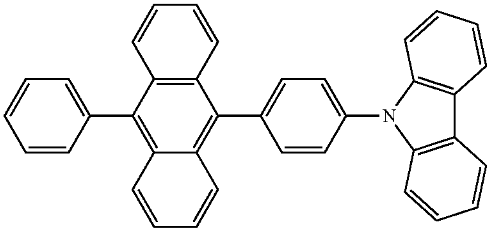
H20
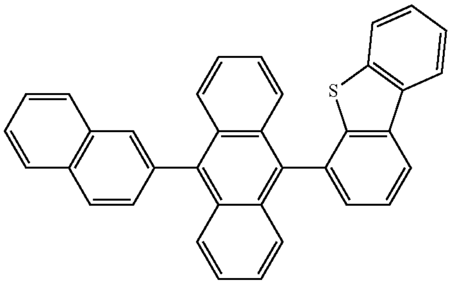
H21
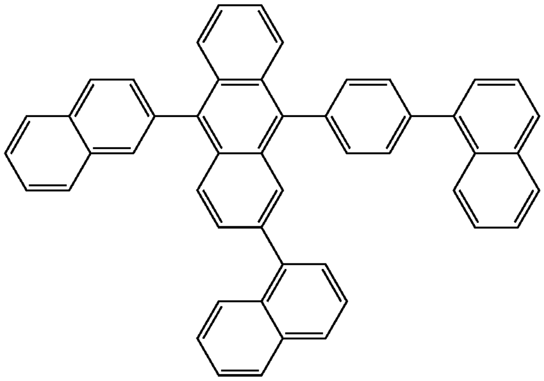
H22
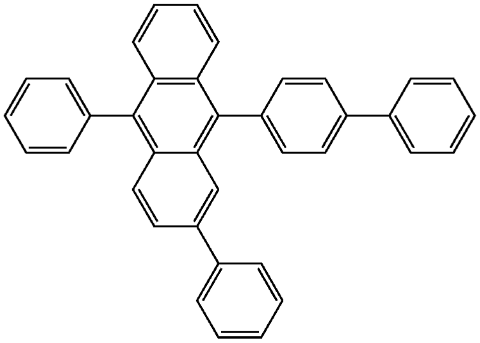

-continued
H23
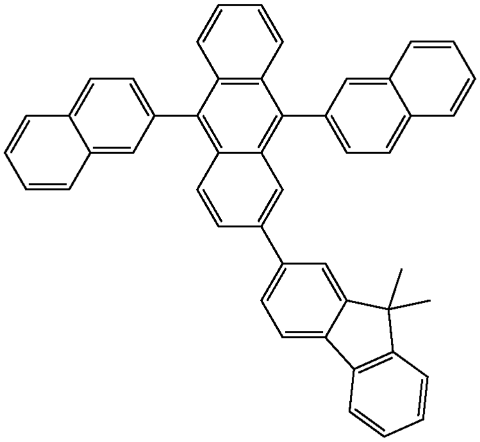
H24
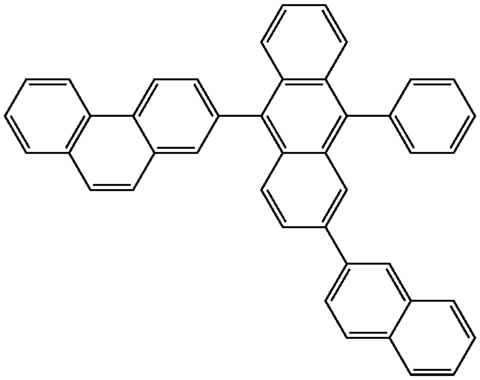
H25
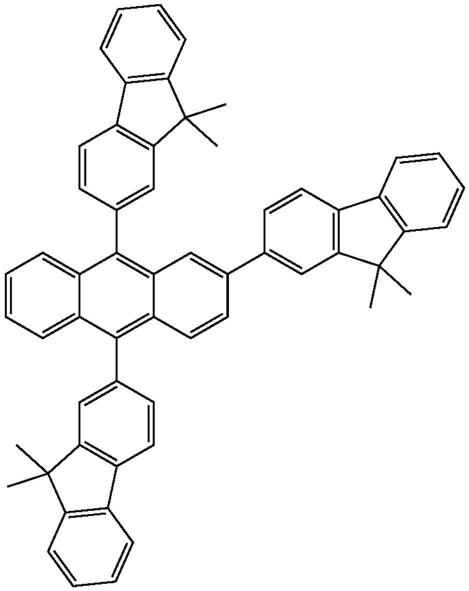
-continued
H26
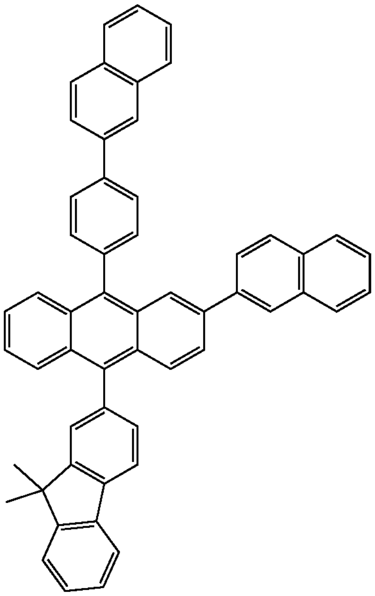
H27
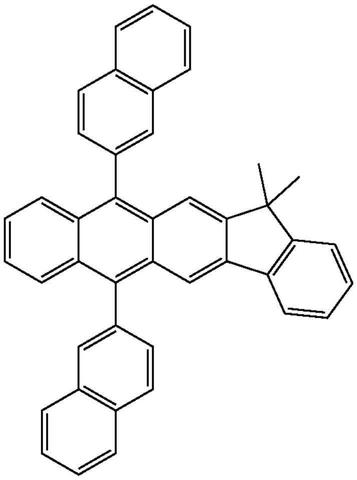
H28
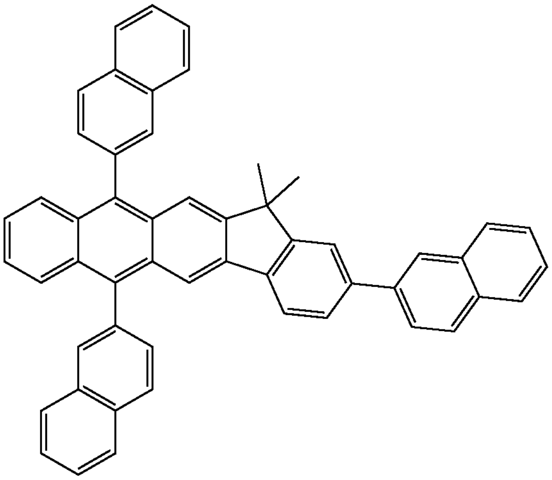

-continued
H29
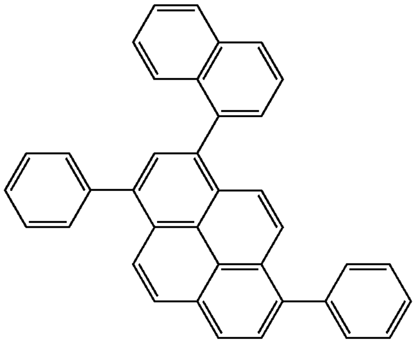
H30
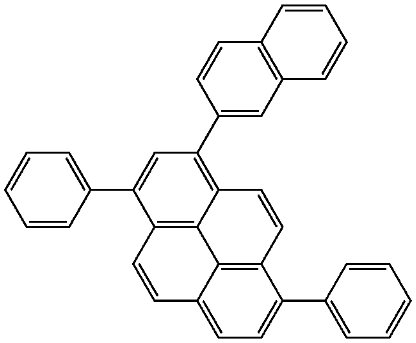
H31
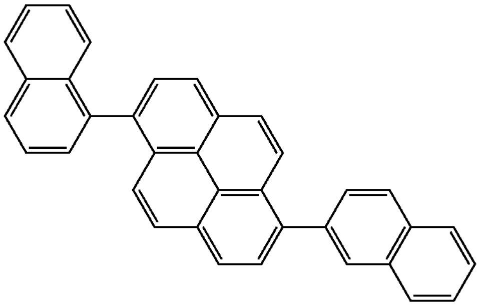
H32
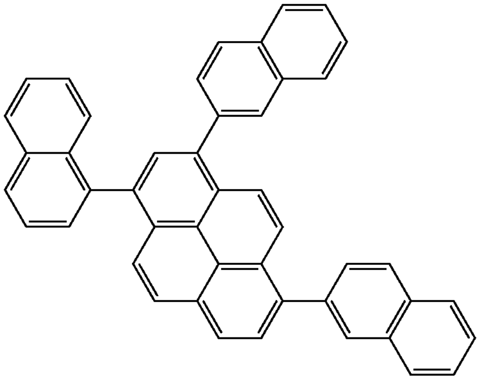
H33
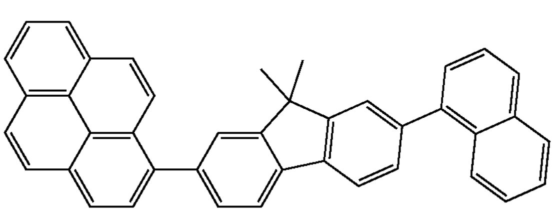
-continued
H34
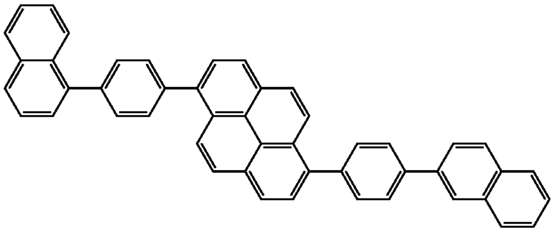
H35
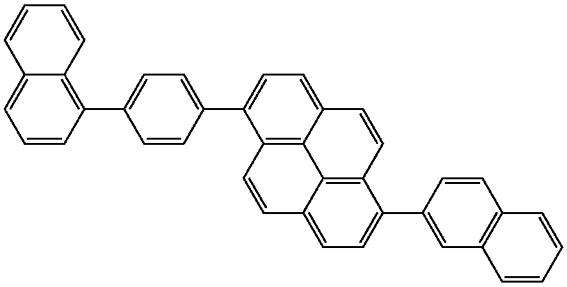
H36
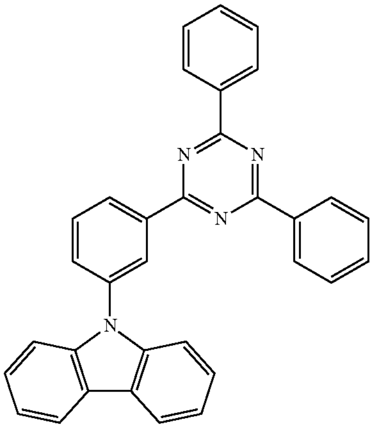
H37
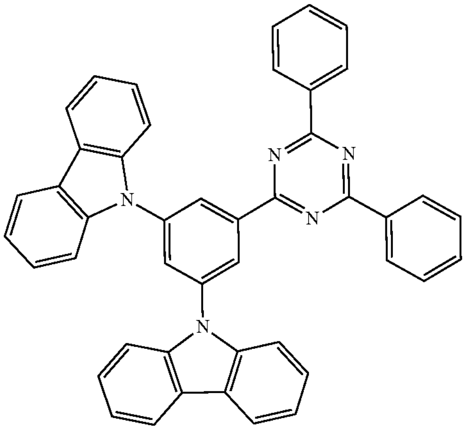

-continued
H38
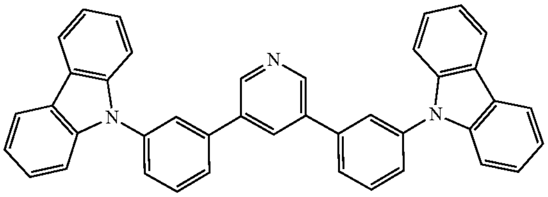
H39
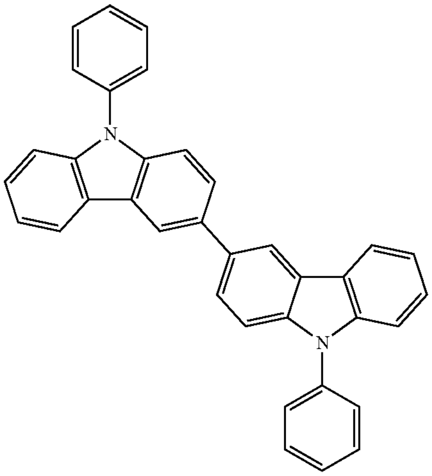
H40
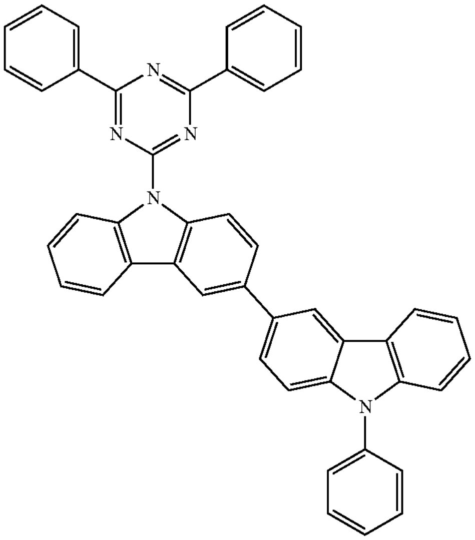
-continued
H41
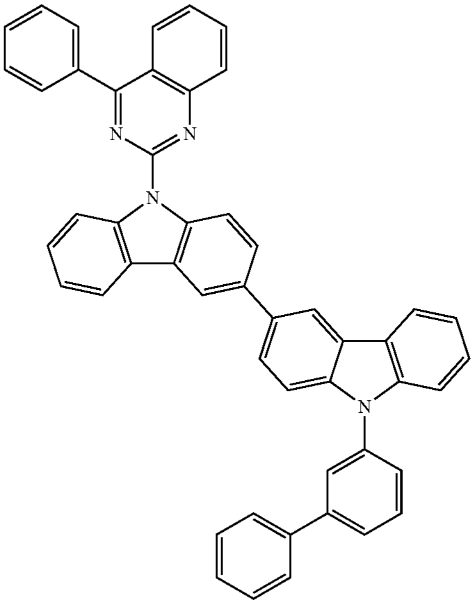
H42
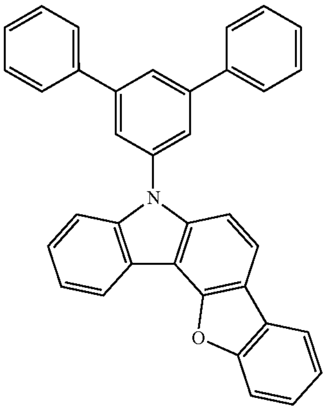
H43
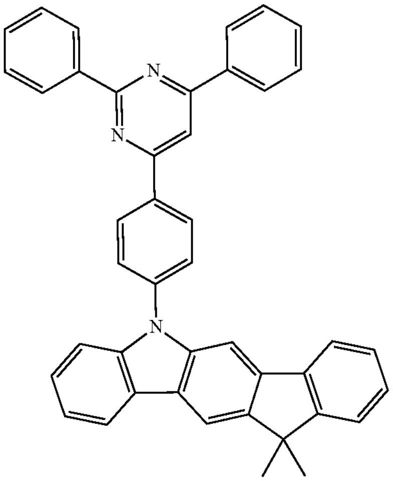

-continued
H44
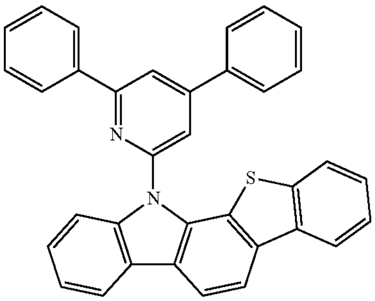
H45
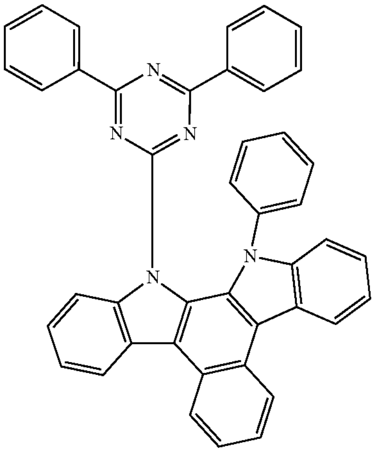
H46
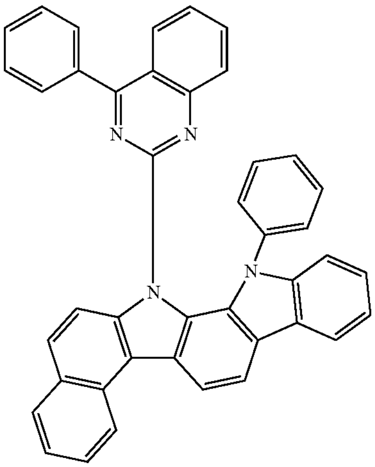
H47
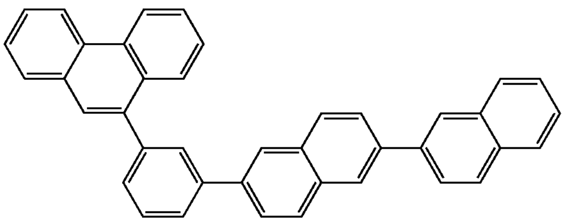
-continued
H48
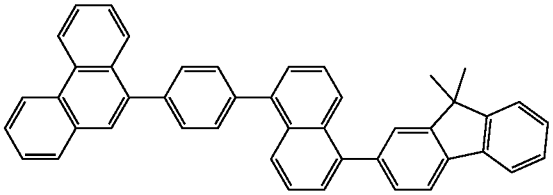
H49
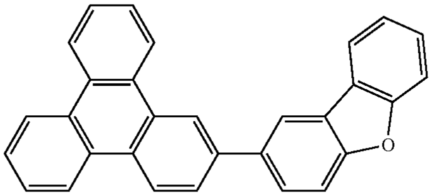
H50
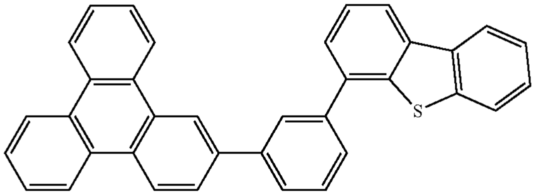
H51
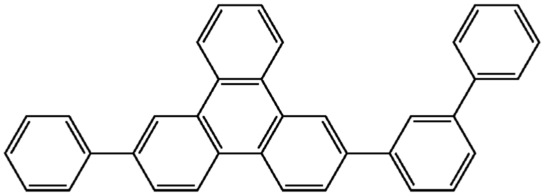
H52
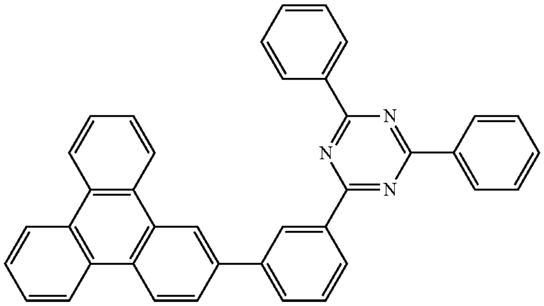
H53
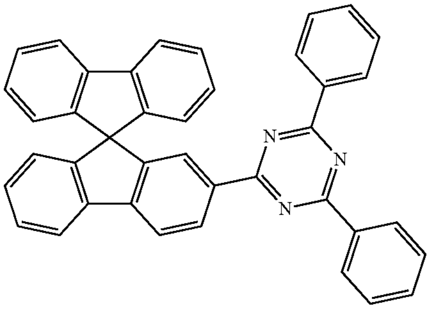

-continued
H54
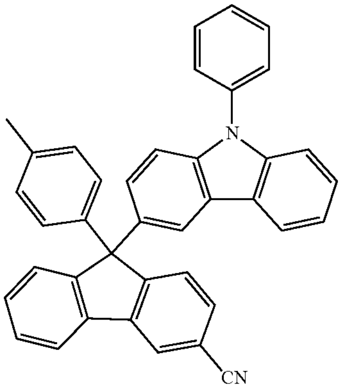
H55
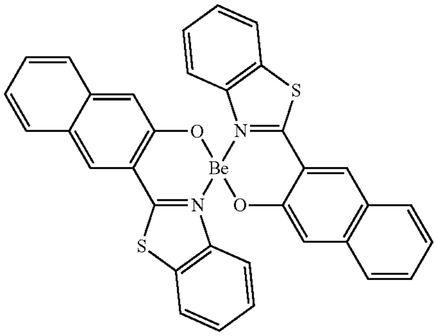
H56
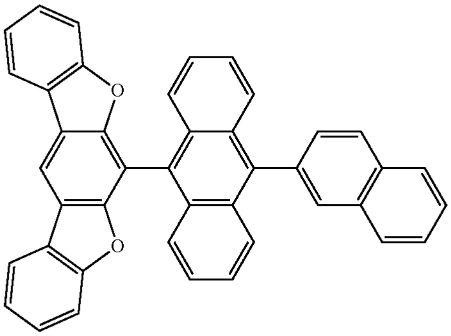
H57
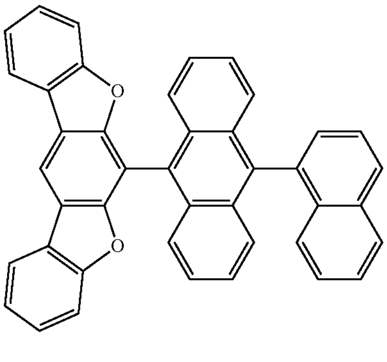
-continued
H58
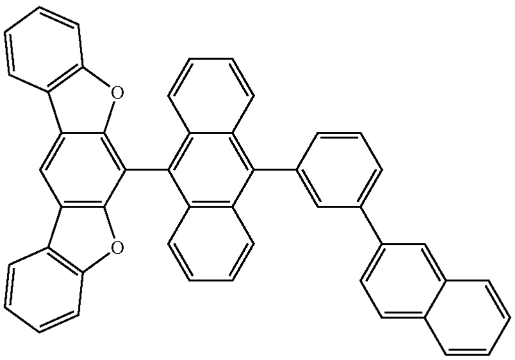
H59
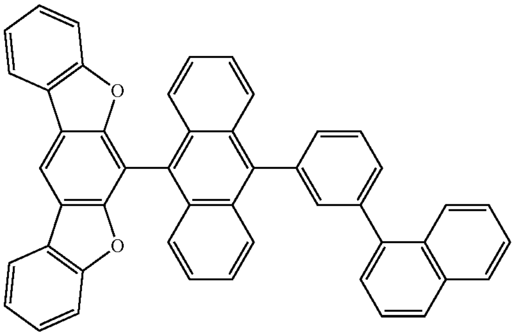
H60
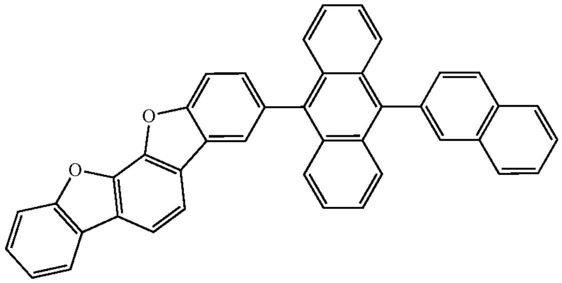
H61
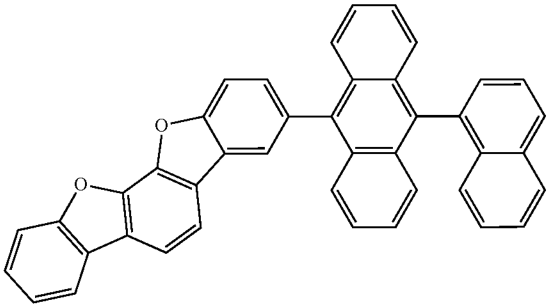

-continued
H62
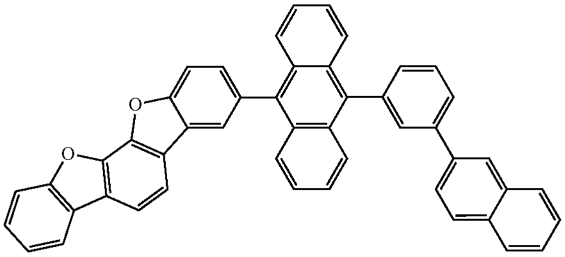
H63
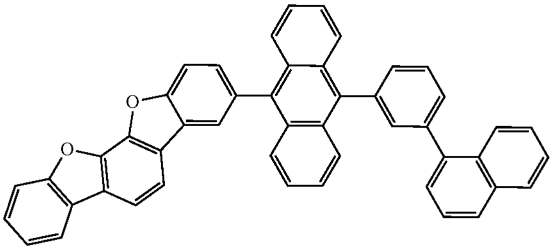
H64
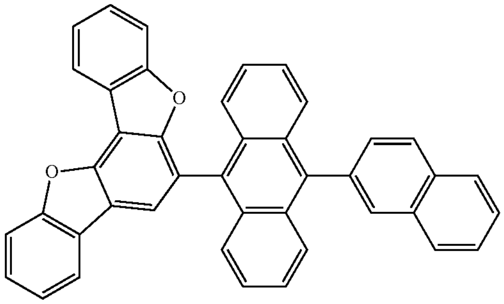
H65
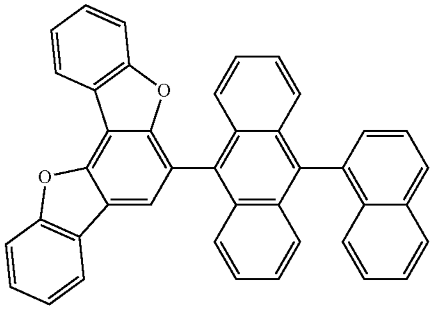
H66
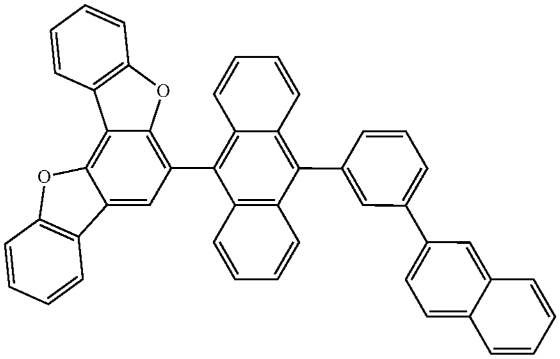
-continued
H67
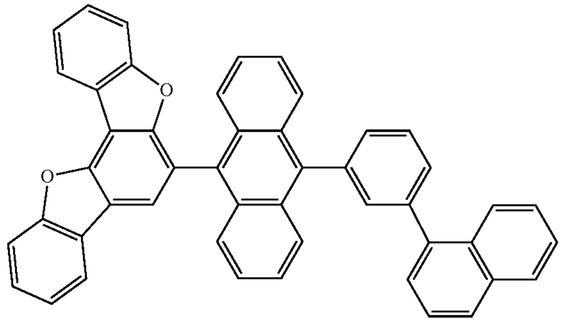
H68
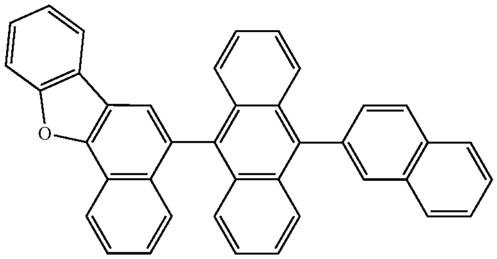
H69
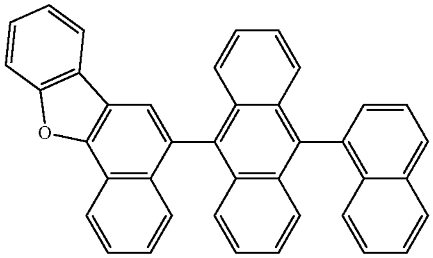
H70
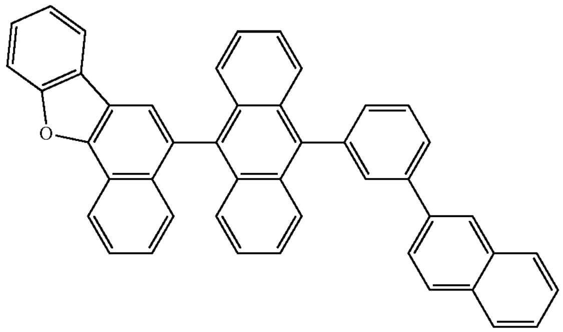
H71
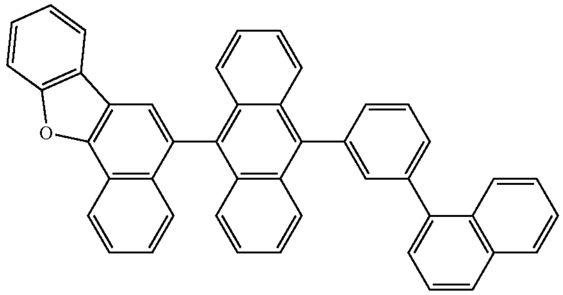

-continued
H72
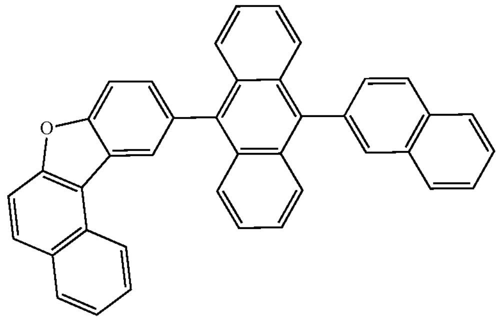
H73
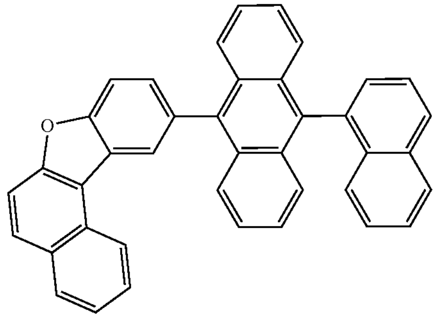
H74
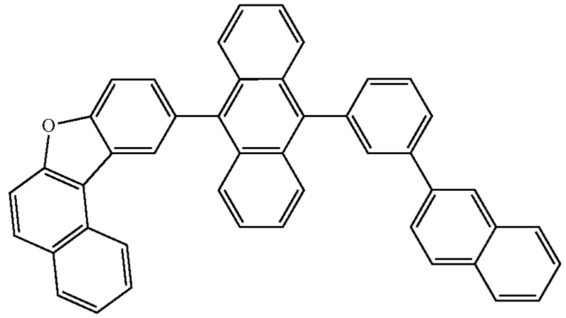
H75
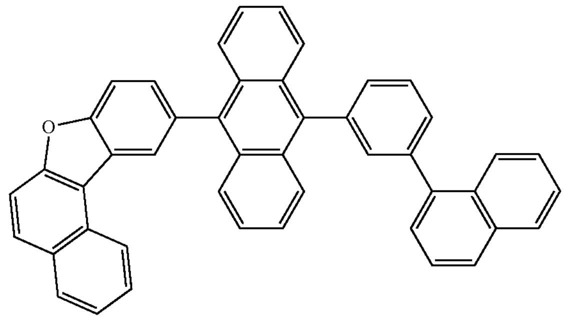
H76
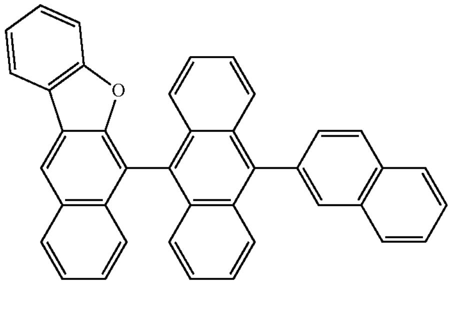
-continued
H77
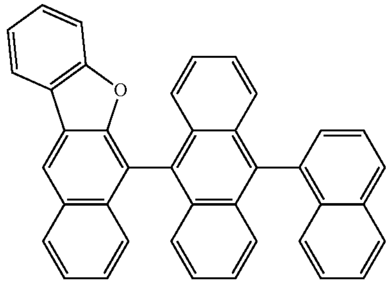
H78
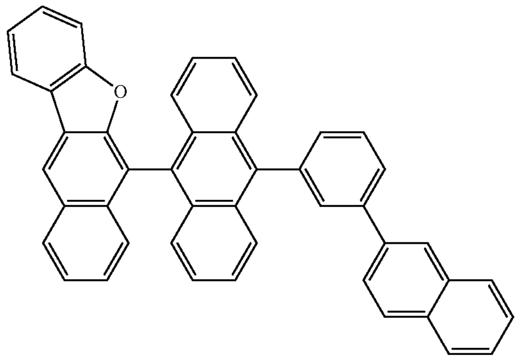
H79
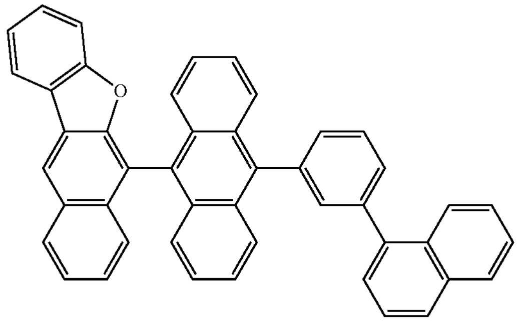
H80
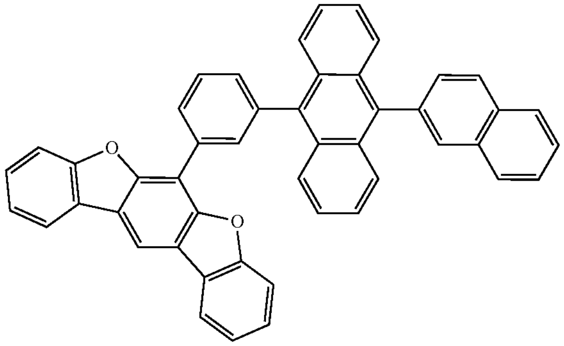

-continued
81
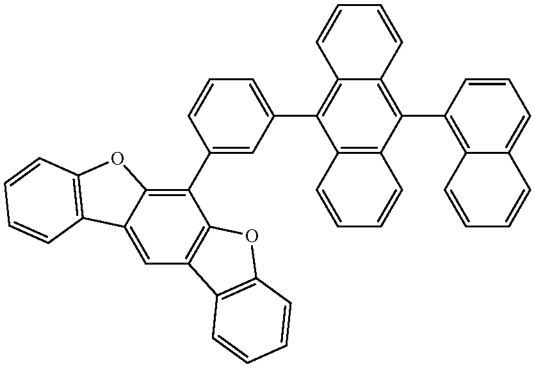
H82
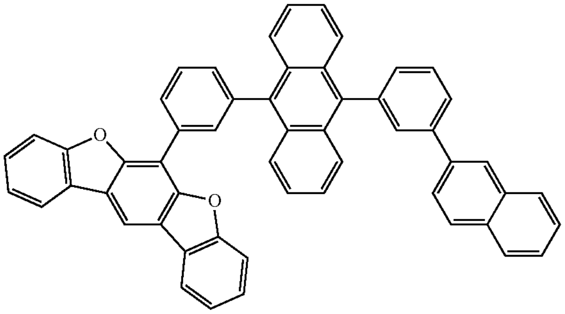
H83
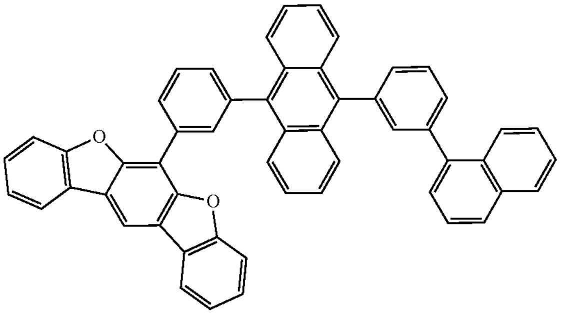
H84
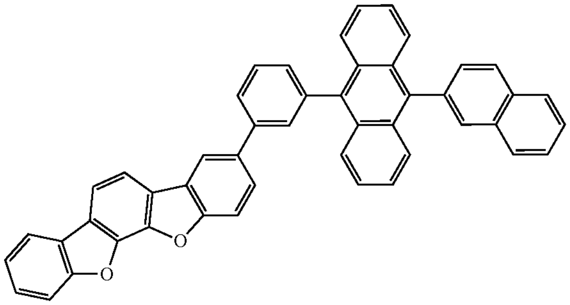
-continued
H85
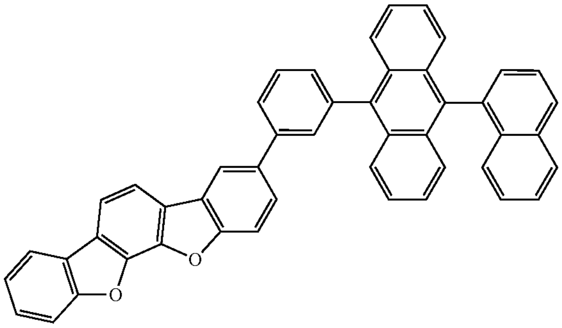
H86
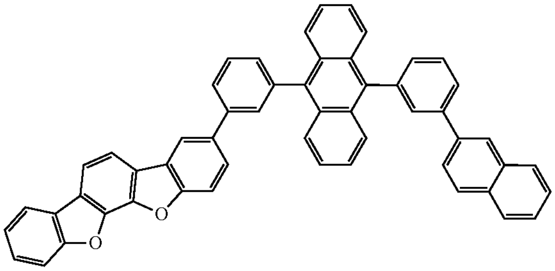
H87
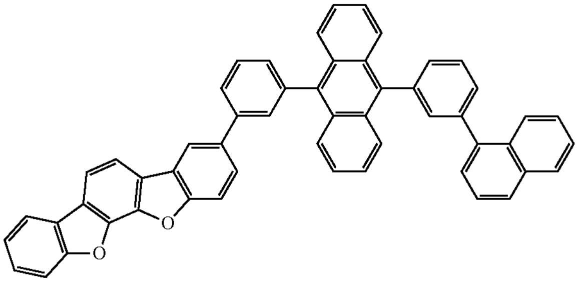
H88
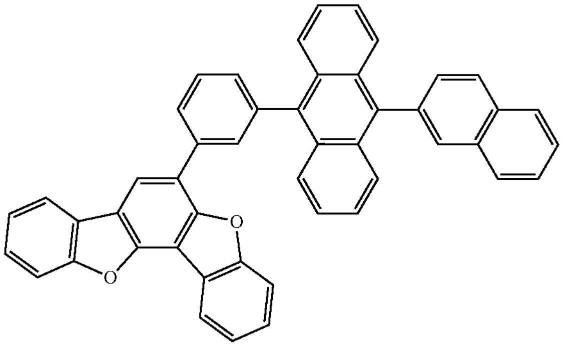

-continued
H89
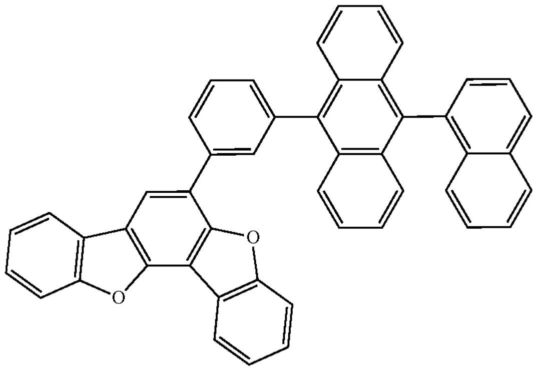
H90
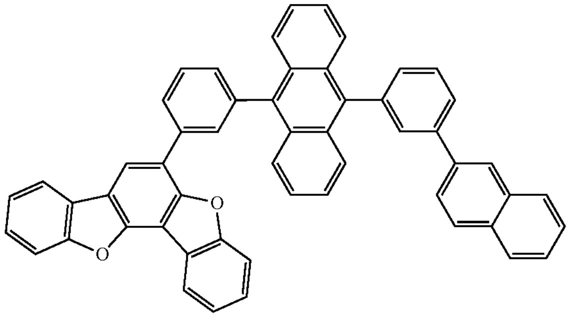
H91
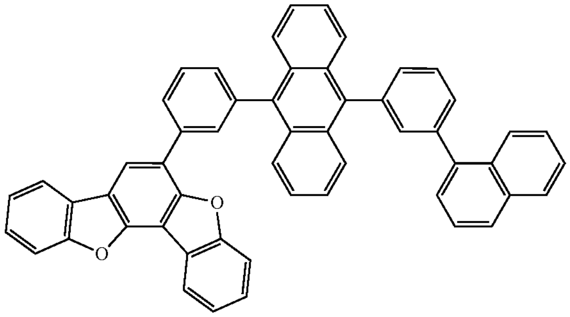
H92
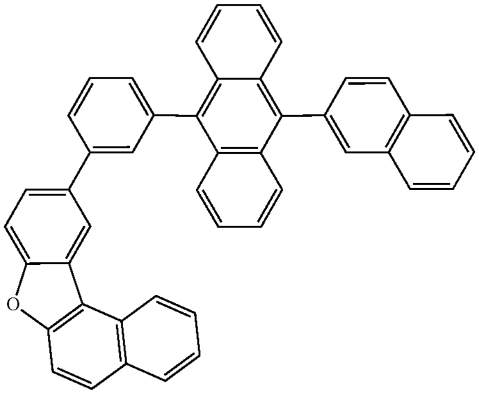
-continued
H93
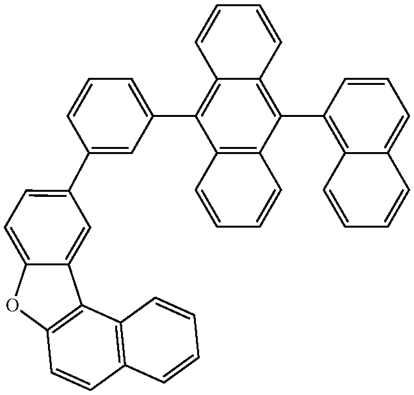
H94
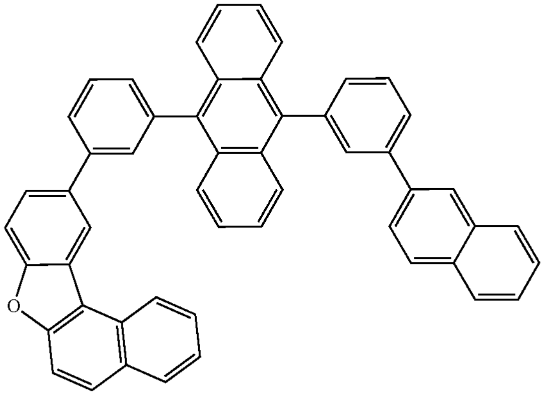
H95
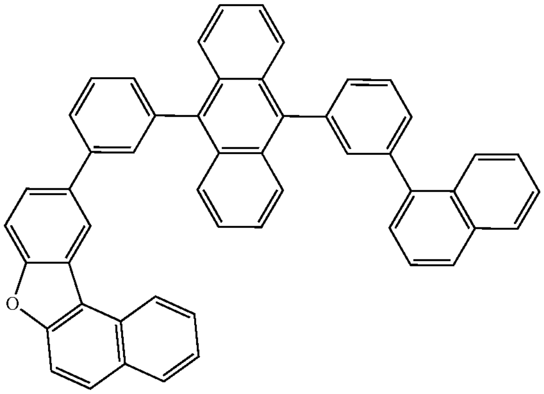
H96
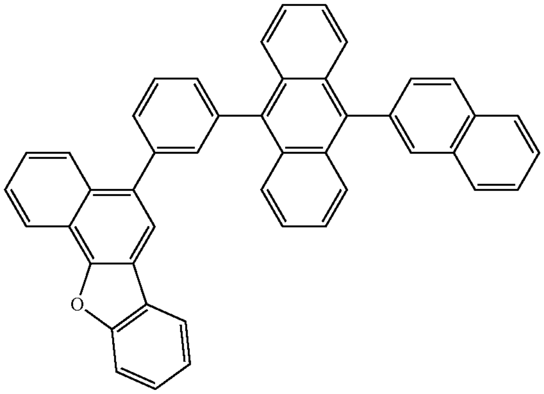

-continued
H97
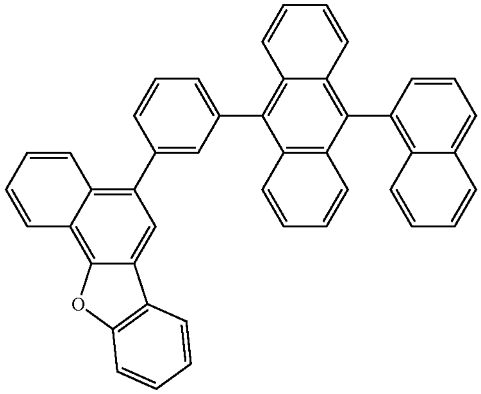
H98
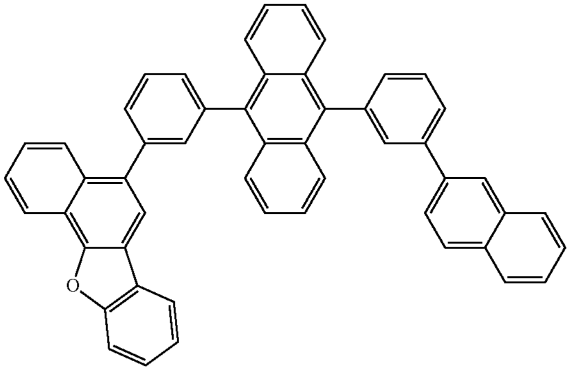
H99
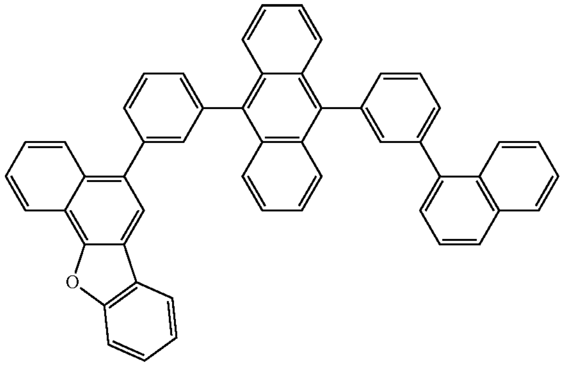
H100
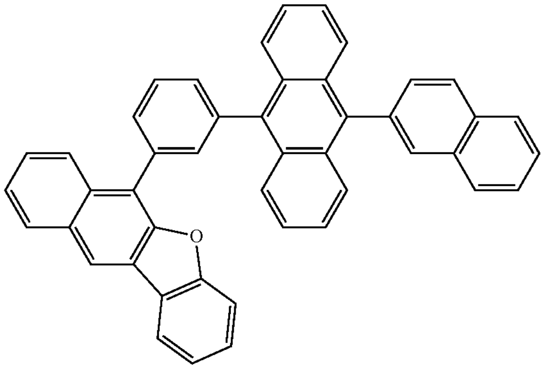
-continued
H101
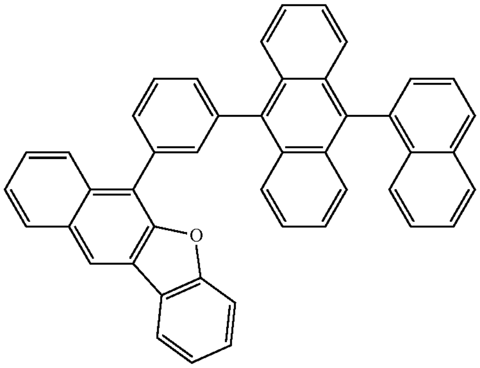
H102
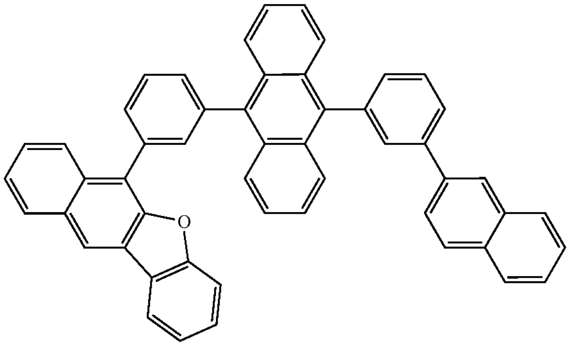
H103
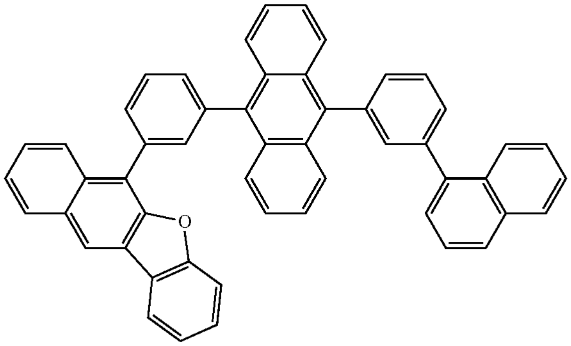
H104.
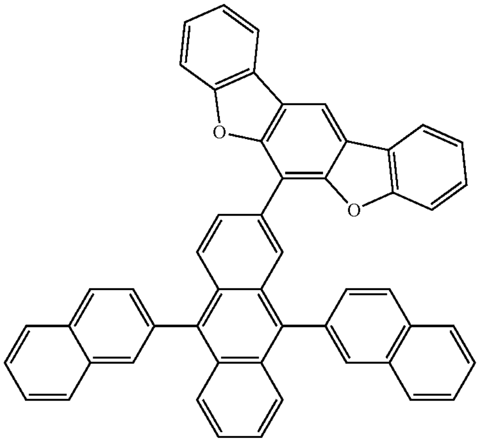

-continued
H105
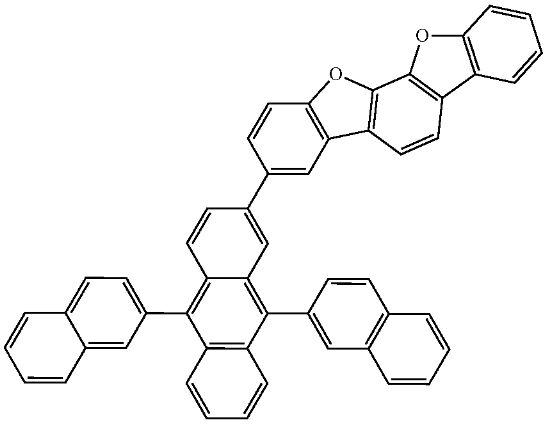
H106
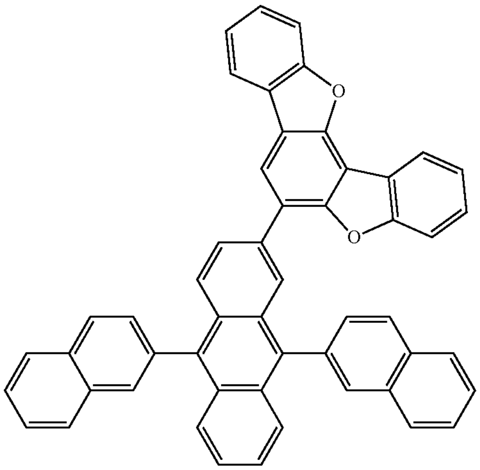
H107
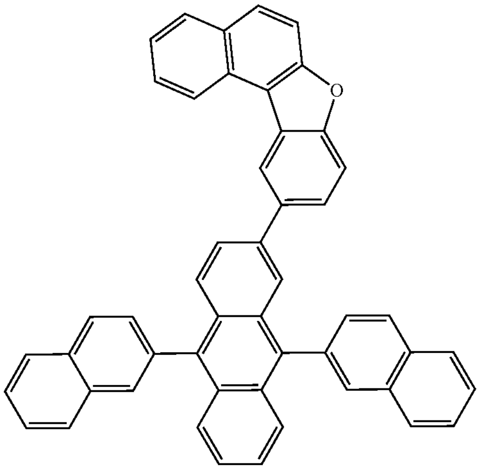
-continued
H108
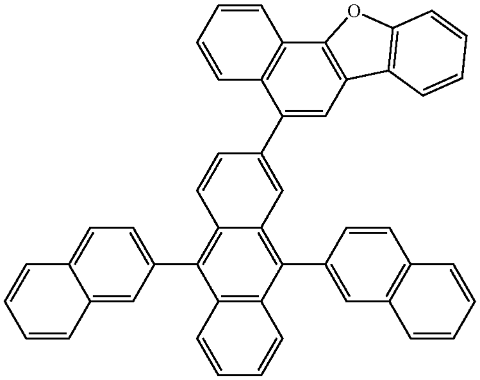
H109
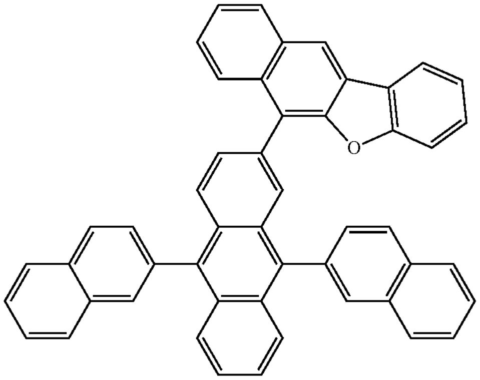
H110
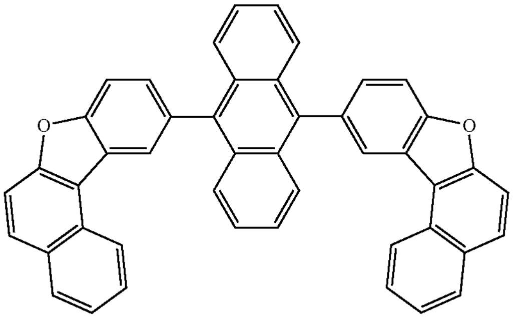
H111
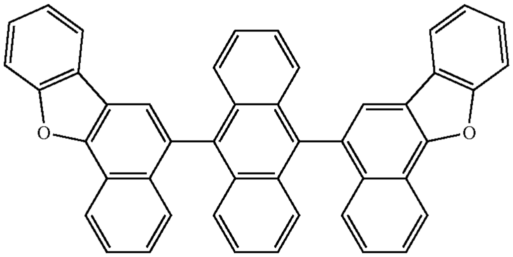

-continued
H112
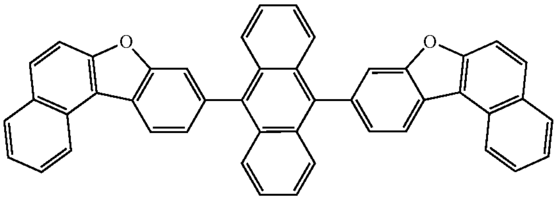
H113
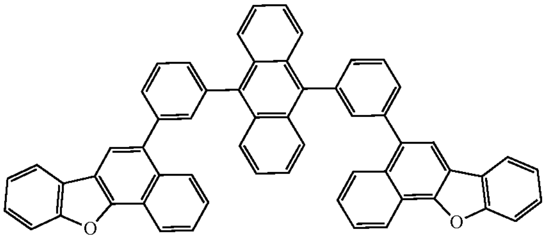
H114
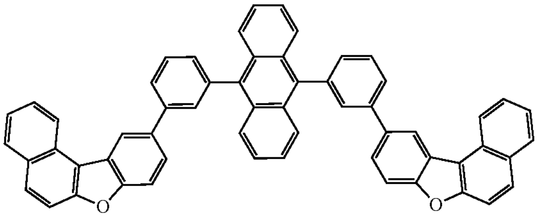
H115
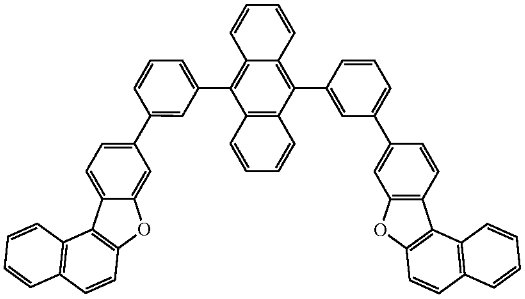
H116
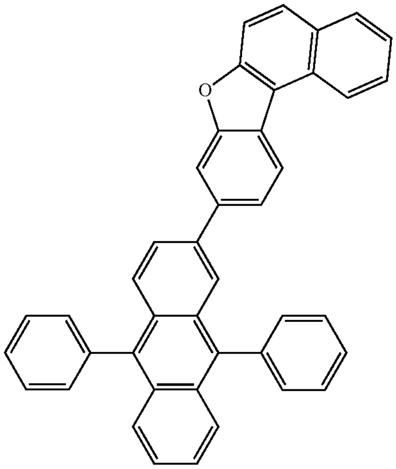
-continued
H117
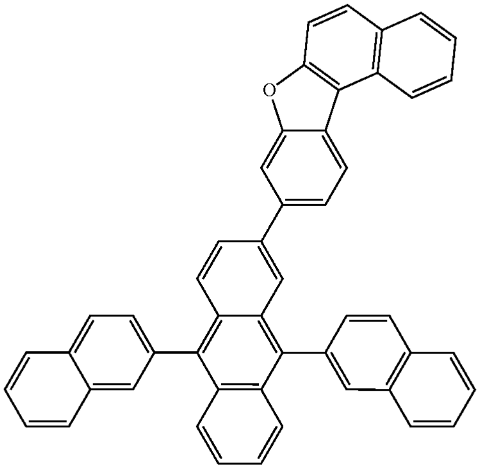
H118
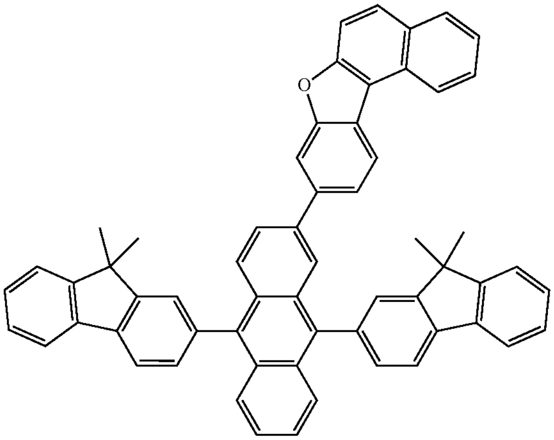
H119
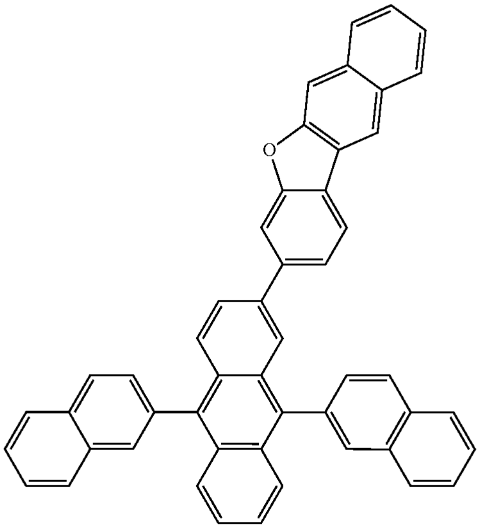

-continued
H120
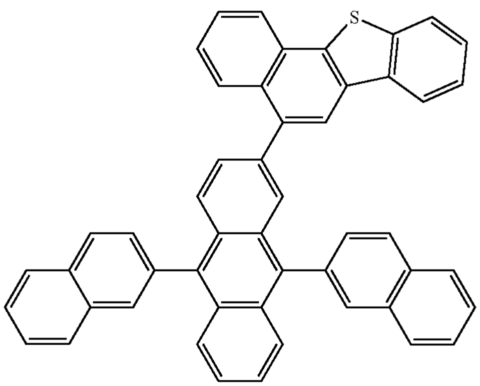
H121
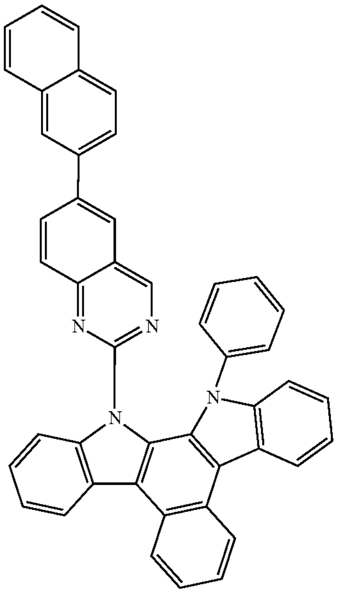
H122
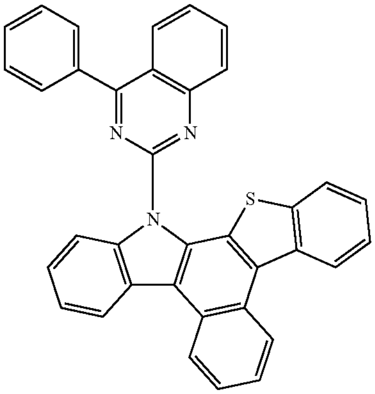
-continued
H123
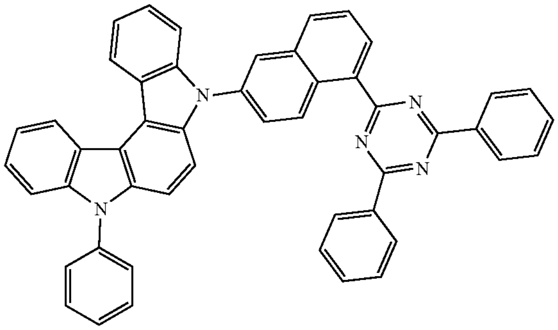
H124
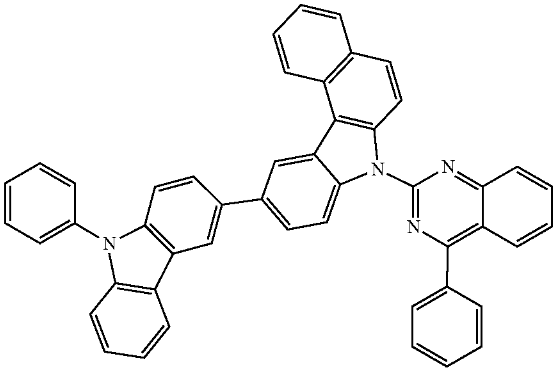
H125
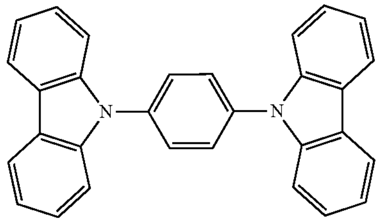
H126
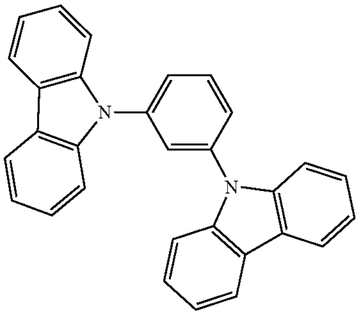
H127
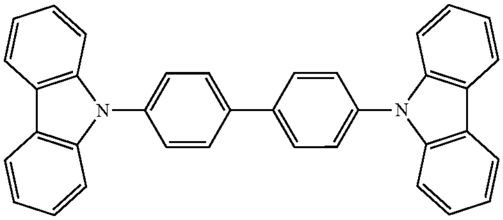

-continued
H128
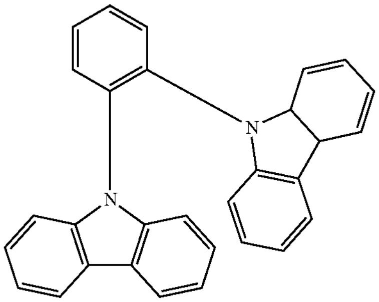
H129
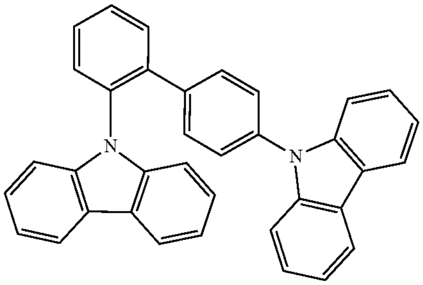
H130
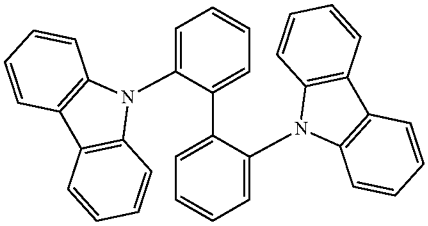
H131
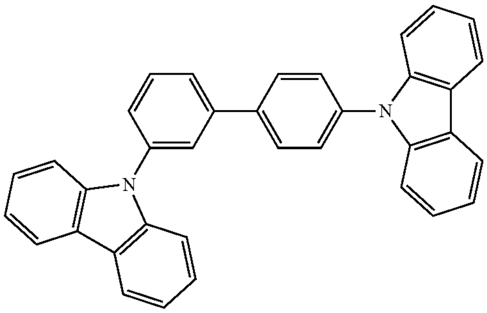
H132
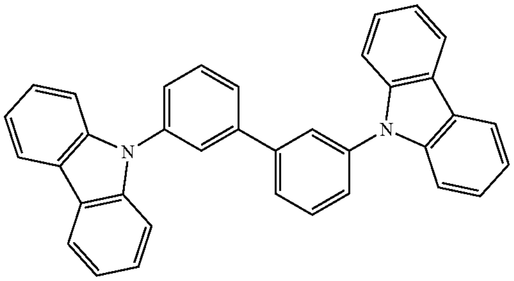
-continued
H133
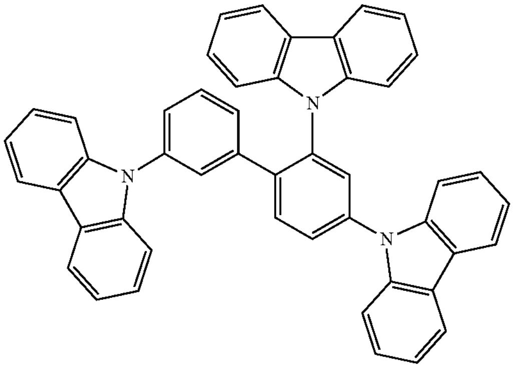
H134
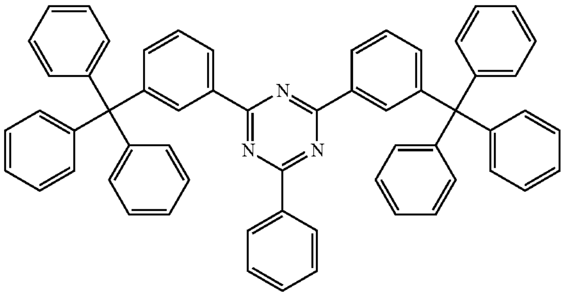
H135
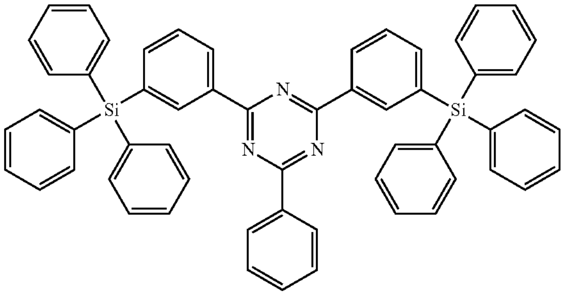
H136
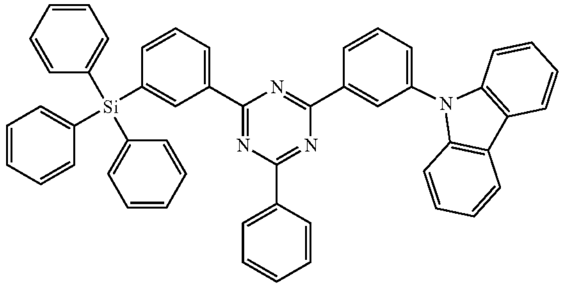

-continued

H137

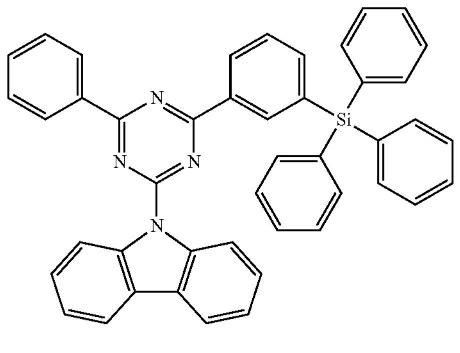

H138

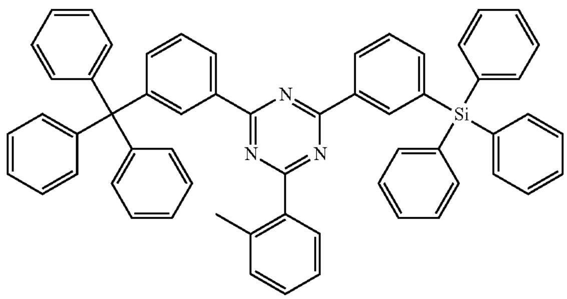

H139

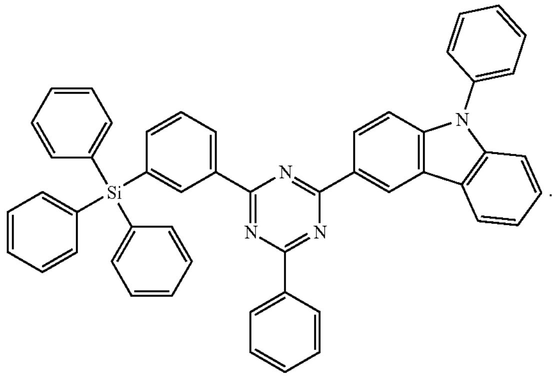

[Phosphorescent Dopant]

The phosphorescent dopant may include at least one transition metal as a center metal.

The phosphorescent dopant may include a monodentate ligand, a bidentate ligand, a tridentate ligand, a tetradentate ligand, a pentadentate ligand, a hexadentate ligand, or any combination thereof.

The phosphorescent dopant may be electrically neutral.

In embodiments, the phosphorescent dopant may include an organometallic complex represented by Formula 401:

[Formula 401]

$$M(L_{401})_{xc1}(L_{402})_{xc2}$$

[Formula 402]

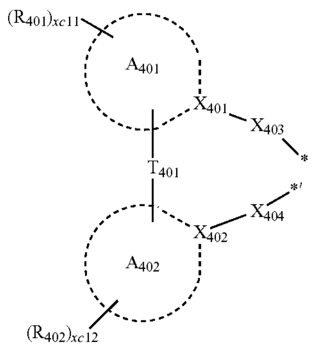

In Formulae 401 and 402,

M may be a transition metal (e.g., iridium (Ir), platinum (Pt), palladium (Pd), osmium (Os), titanium (Ti), gold (Au), hafnium (Hf), europium (Eu), terbium (Tb), rhodium (Rh), rhenium (Re), or thulium (Tm)), $L_{401}$ may be a ligand represented by Formula 402, and xc1 may be 1, 2, or 3, and when xc1 is 2 or greater, at least two $L_{401}$(s) may be identical to or different from each other, $L_{402}$ may be an organic ligand, and xc2 may be an integer from 0 to 4, and when xc2 is 2 or greater, at least two $L_{402}$(s) may be identical to or different from each other, $X_{401}$ and $X_{402}$ may each independently be nitrogen (N) or carbon (C), ring $A_{401}$ and ring $A_{402}$ may each independently be a $C_3$-$C_{60}$ carbocyclic group or a $C_1$-$C_{60}$ heterocyclic group, $T_{401}$ may be a single bond, *—O—**, *—S—*, *—C(=O)—**, *—N($Q_{411}$)-*, *—C($Q_{411}$)($Q_{412}$)-**, *—C($Q_{411}$)-C($Q_{412}$)-**, *—C($Q_{411}$)=*', or *=C=*', $X_{403}$ and $X_{404}$ may each independently be a chemical bond (e.g., a covalent bond or a coordinate bond), O, S, N($Q_{413}$), B($Q_{413}$), P($Q_{413}$), C($Q_{413}$)($Q_{414}$), or Si($Q_{413}$)($Q_{414}$), $Q_{411}$ to $Q_{414}$ may each independently be the same as described in connection with $Q_1$ provided herein, $R_{401}$ and $R_{402}$ may each independently be hydrogen, deuterium, —F, —Cl, —Br, —I, a hydroxyl group, a cyano group, a nitro group, a $C_1$-$C_{20}$ alkyl group unsubstituted or substituted with at least one $R_{10a}$, a $C_1$-$C_{20}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), or —P(=O)($Q_{401}$)($Q_{402}$), $Q_{401}$ to $Q_{403}$ may each independently be the same as described in connection with $Q_1$ provided herein, xc11 and xc12 may each independently be an integer from 0 to 10, and

* and *' in Formula 402 each indicate a binding site to M in Formula 401.

In embodiments, in Formula 402, $X_{401}$ may be nitrogen and $X_{402}$ may be carbon, or $X_{401}$ and $X_{402}$ may both be nitrogen.

In embodiments, when xc1 in Formula 402 is 2 or greater, two ring $A_{401}$(s) of at least two $L_{401}$(s) may optionally be bound via $T_{402}$ as a linking group, or two ring $A_{402}$(s) may optionally be bound via $T_{403}$ as a linking group (see Compounds PD1 to PD4 and PD7). $T_{402}$ and $T_{403}$ may each independently be the same as described in connection with $T_{401}$ provided herein.

$L_{402}$ in Formula 401 may be any suitable organic ligand. For example, $L_{402}$ may be a halogen group, a diketone group (e.g., an acetylacetonate group), a carboxylic acid group (e.g., a picolinate group), —C(═O), an isonitrile group, —CN, or a phosphorus group (e.g., a phosphine group or a phosphite group).

The phosphorescent dopant may be, for example, one of Compounds PD1 to PD41, or any combination thereof:

PD1

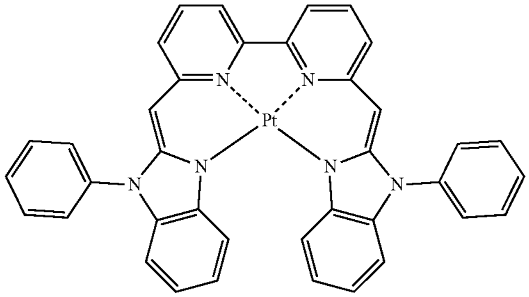

PD2

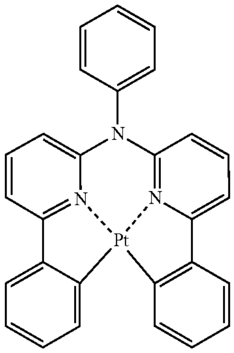

PD3

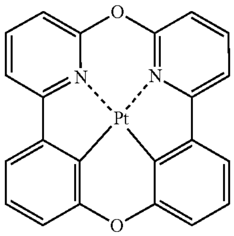

PD4

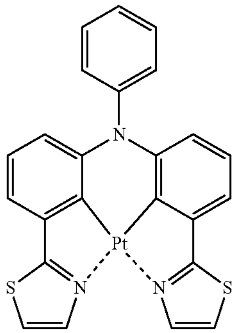

-continued

PD5

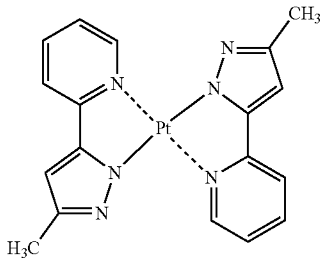

PD6

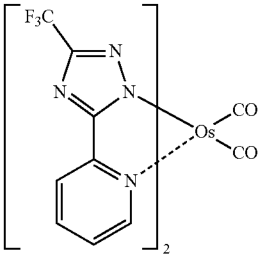

PD7

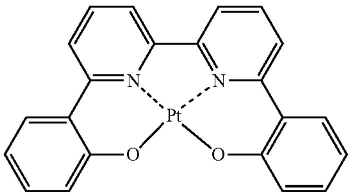

PD8

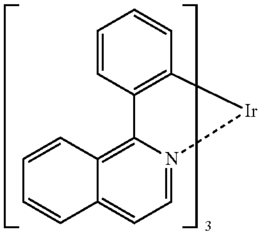

PD9

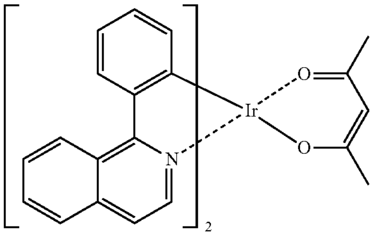

PD10

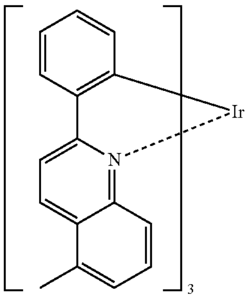

-continued
PD11
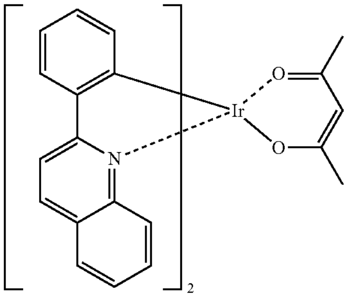
PD12
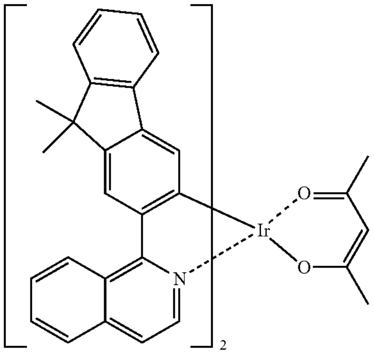
PD13
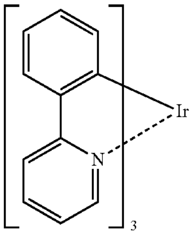
PD14
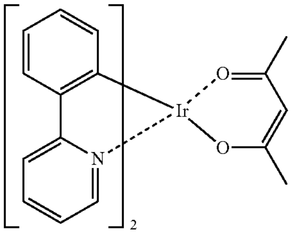
PD15
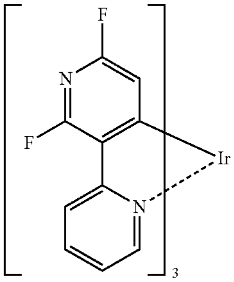
-continued
PD16
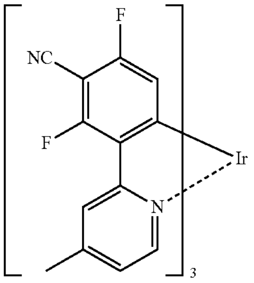
PD17
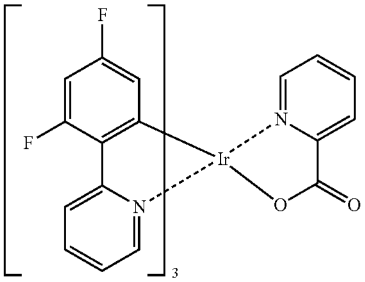
PD18
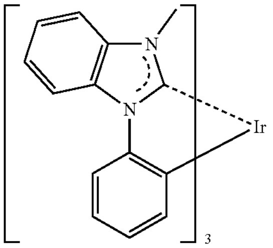
PD19
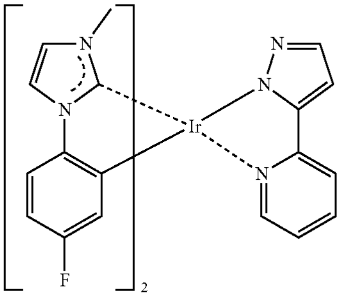
PD20
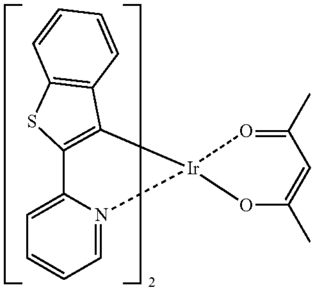

-continued
PD21
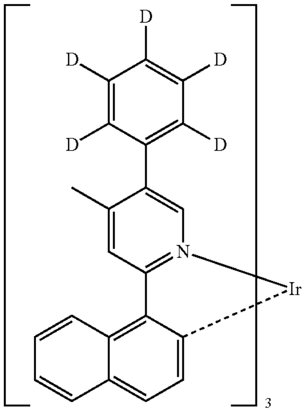
PD22
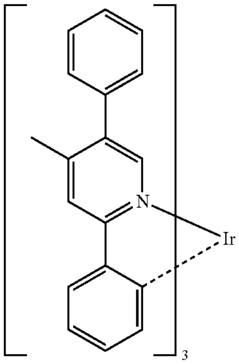
PD23
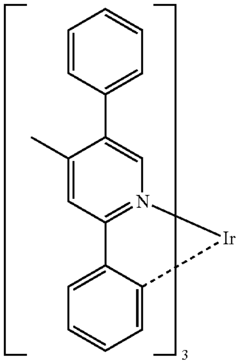
PD24
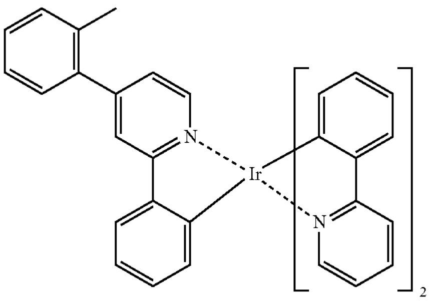
-continued
PD25
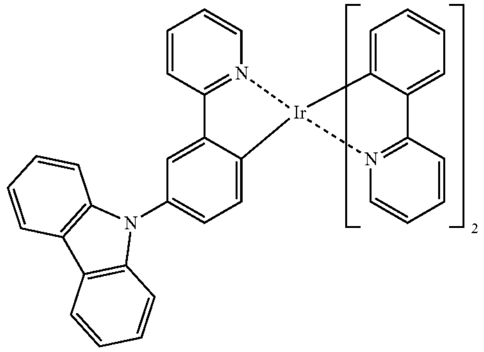
PD26
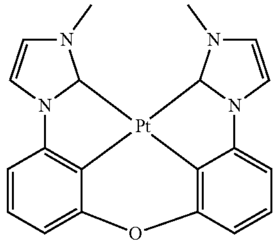
PD27
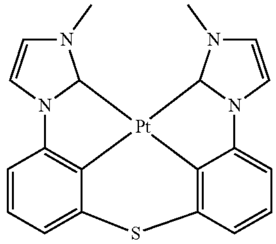
PD28
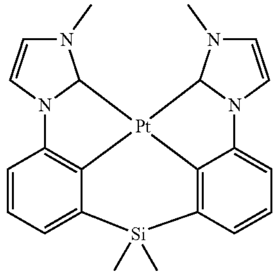
PD29
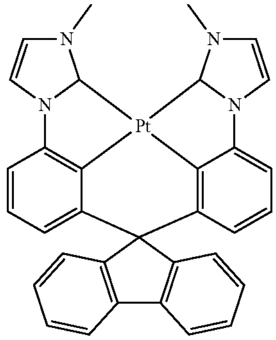

-continued
PD30
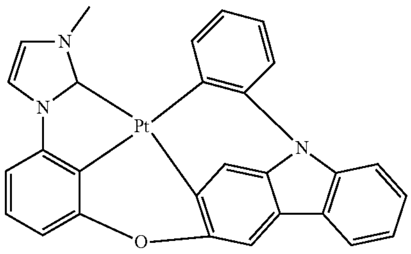
PD31
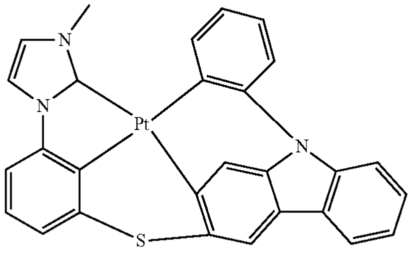
PD32
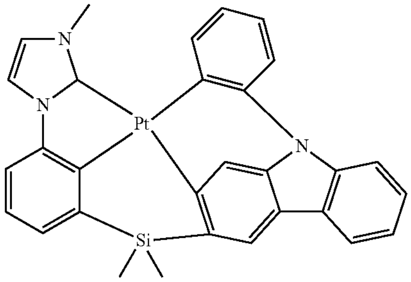
PD33
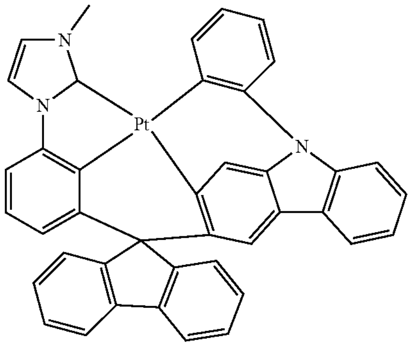
PD34
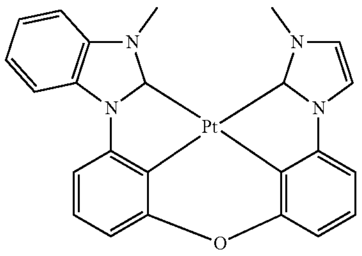
-continued
PD35
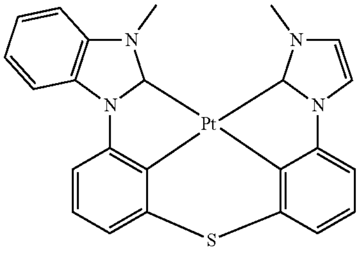
PD36
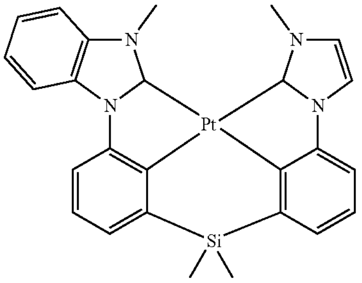
PD37
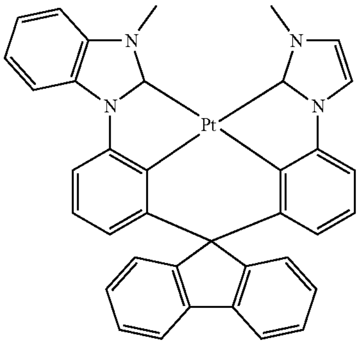
PD38
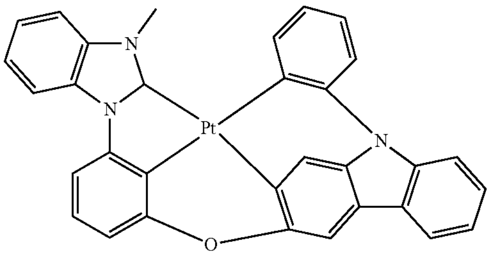
PD39
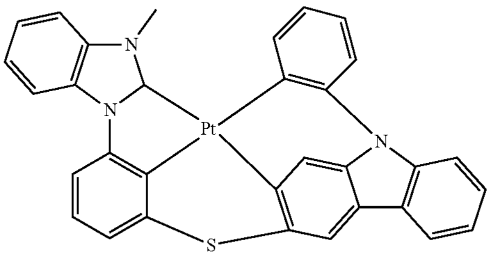

-continued

PD40

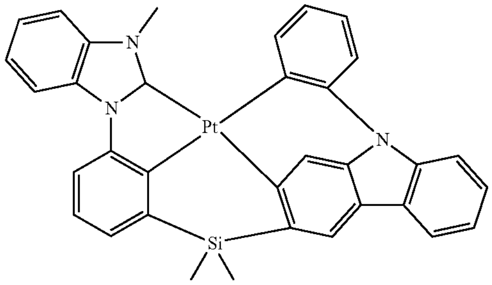

PD41

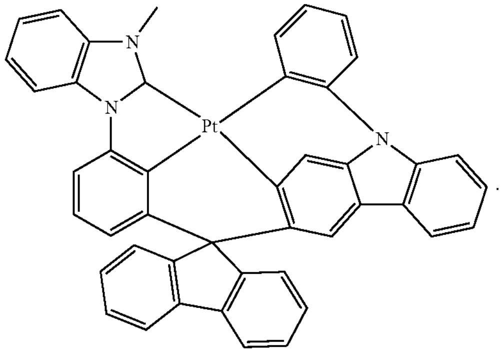

[Fluorescent Dopant]

The fluorescent dopant may include an amine group-containing compound, a styryl group-containing compound, or any combination thereof.

In embodiments, the fluorescent dopant may include a compound represented by Formula 501:

[Formula 501]

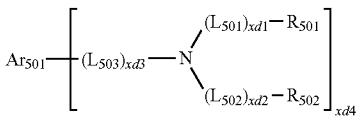

In Formula 501, $Ar_{501}$, $L_{501}$ to $L_{503}$, $R_{501}$, and $R_{502}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xd1 to xd3 may each independently be 0, 1, 2, or 3, and xd4 may be 1, 2, 3, 4, 5, or 6.

In embodiments, in Formula-501, $Ar_{501}$ may include a condensed ring group (e.g., an anthracene group, a chrysene group, or a pyrene group) in which at least three monocyclic groups are condensed.

In embodiments, xd4 in Formula 501 may be 2.

In embodiments, the fluorescent dopant may include one of Compounds FD1 to FD36, DPVBi, DPAVBi, or any combination thereof:

FD1

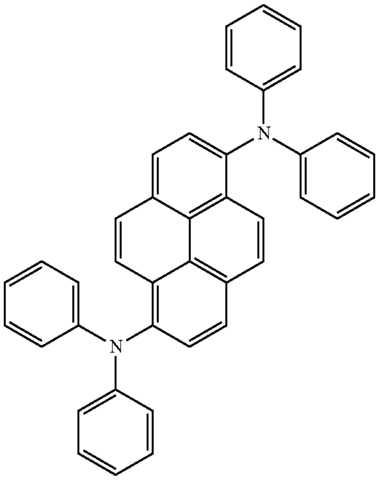

FD2

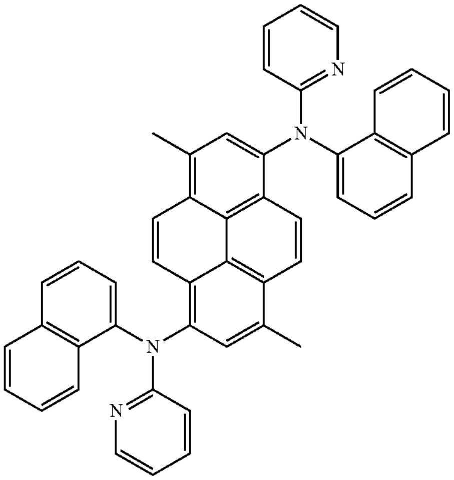

FD3

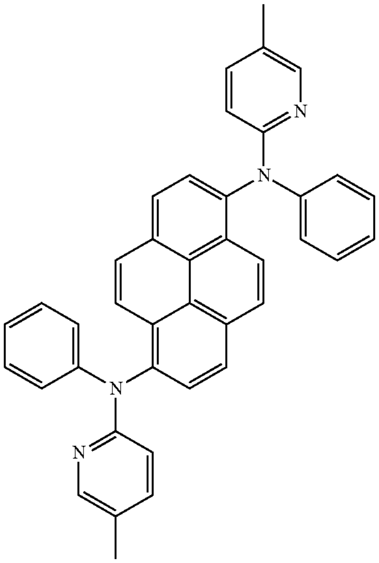

-continued
FD4
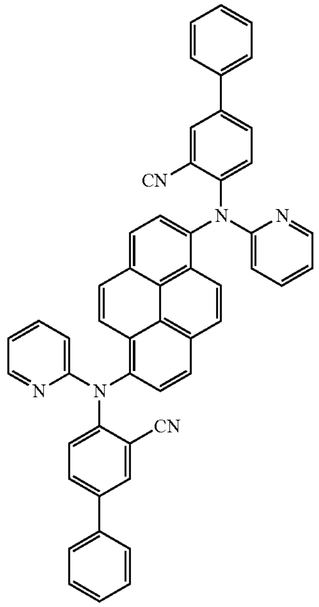
FD5
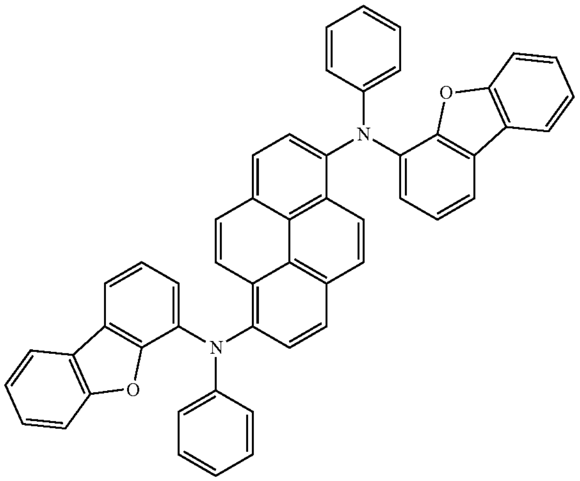
FD6
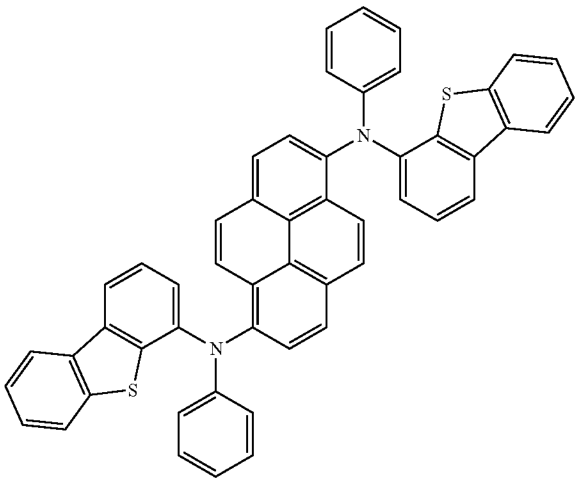
-continued
FD7
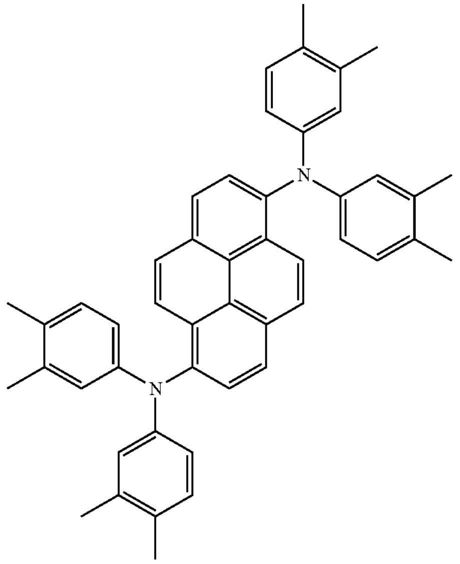
FD8
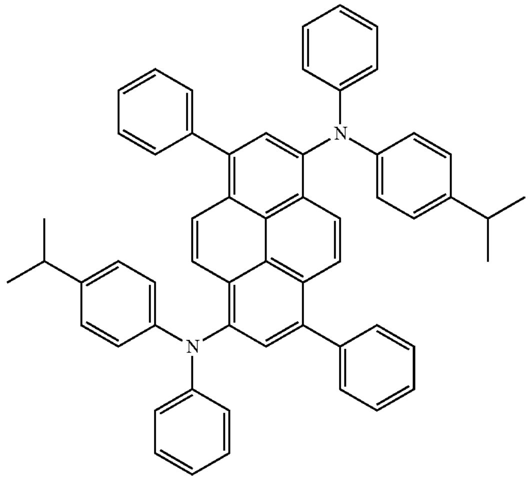
FD9
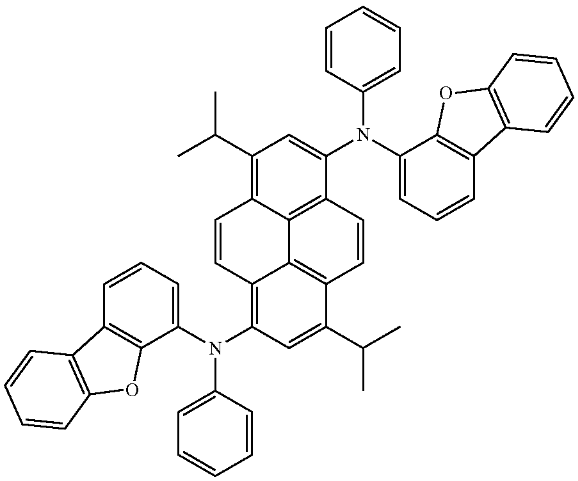

-continued
FD10
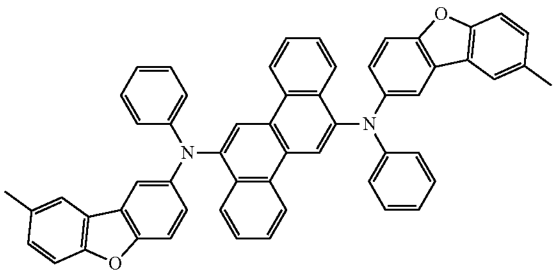
FD11
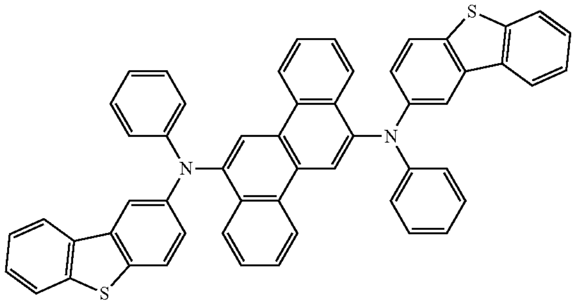
FD12
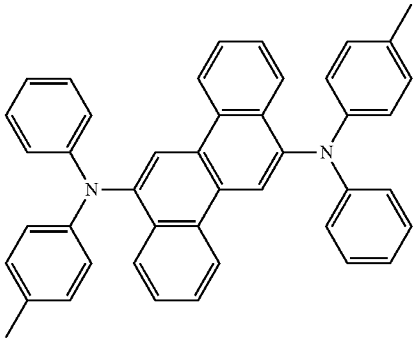
FD13
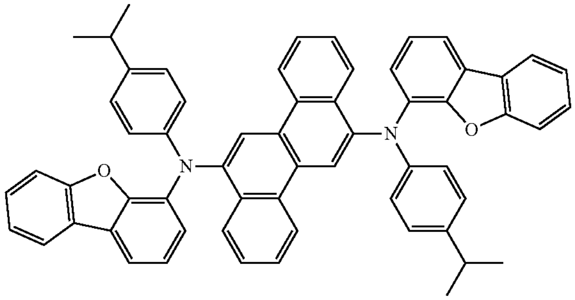
FD14
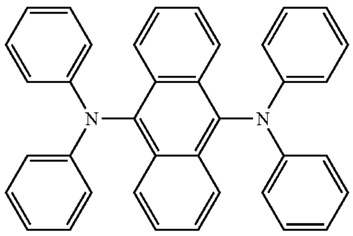
-continued
FD15
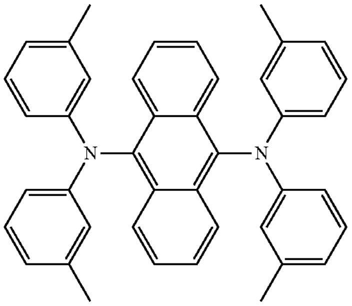
FD16
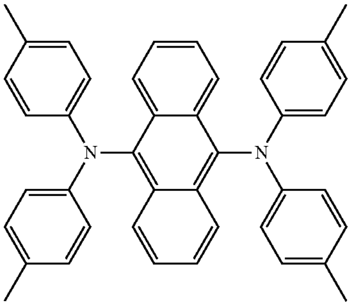
FD17
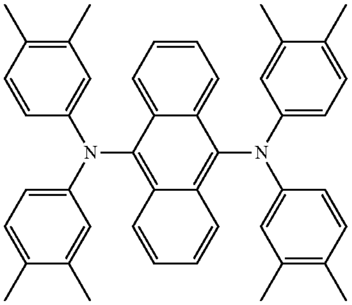
FD18
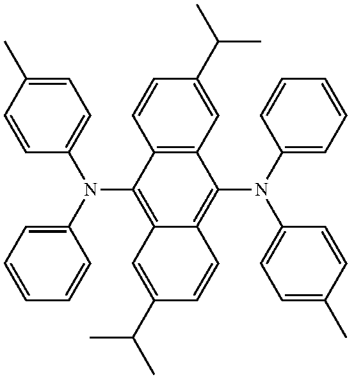

-continued
FD19
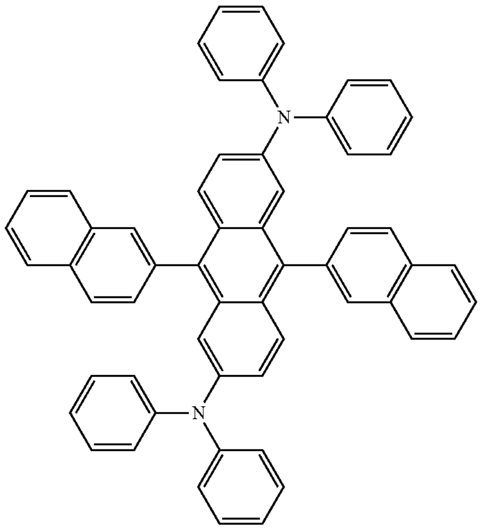
FD20
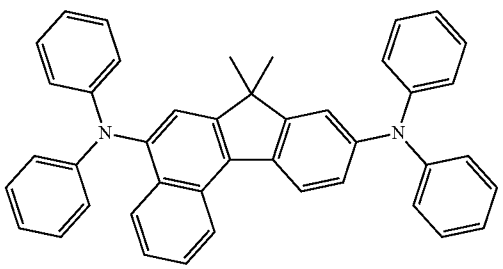
FD21
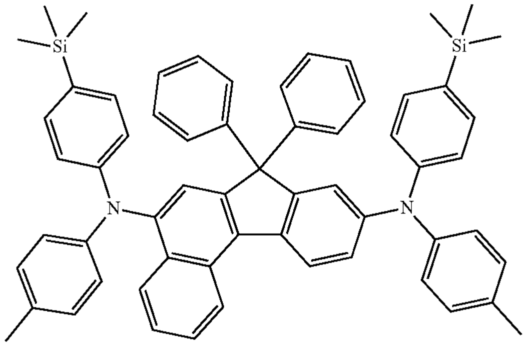
FD22
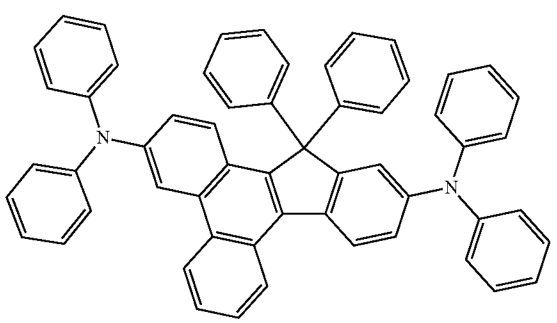
-continued
FD23
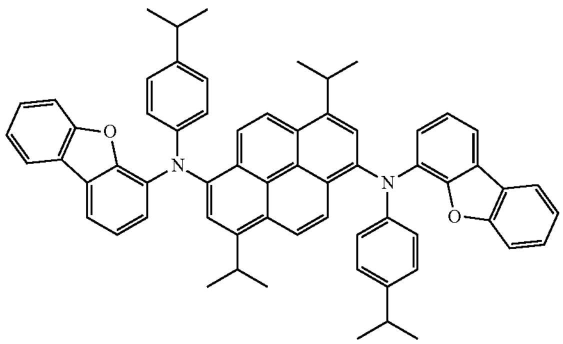
FD24
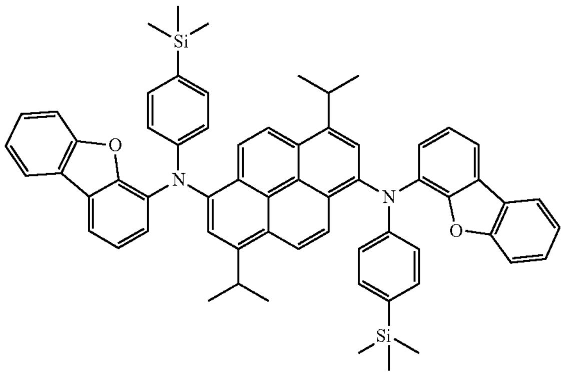
FD25
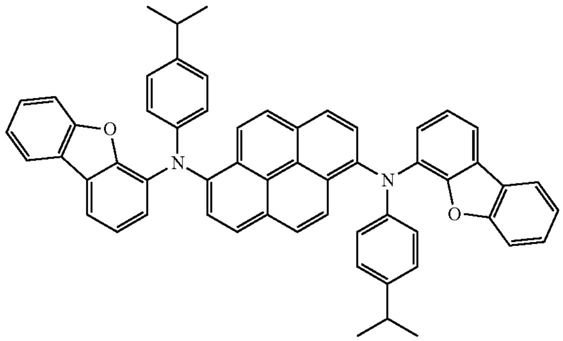
FD26
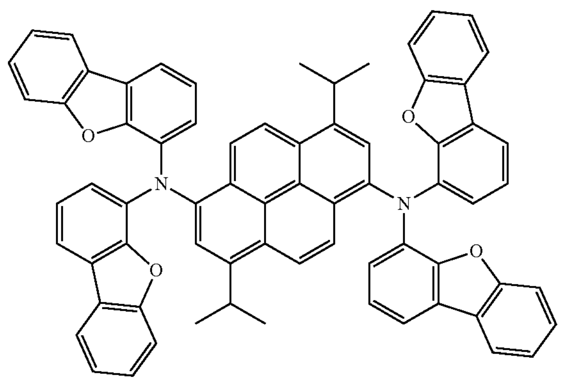

-continued
FD27
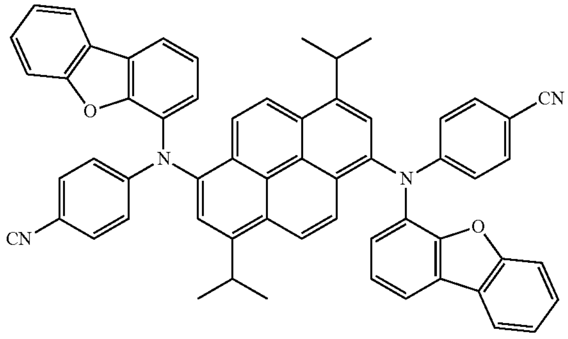
FD28
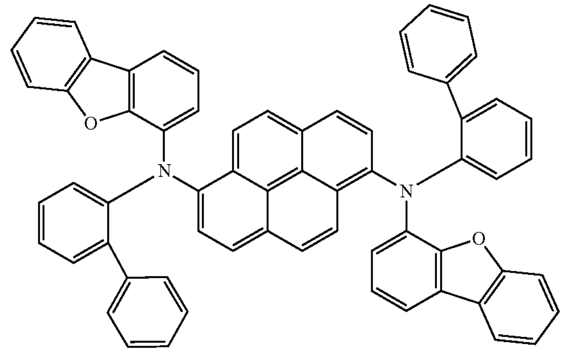
FD29
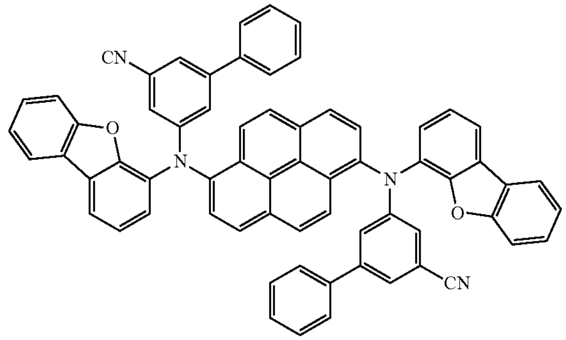
FD30
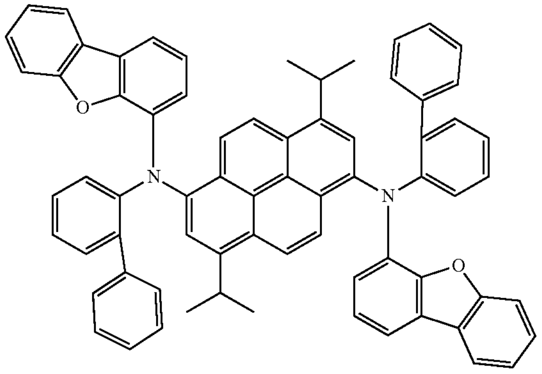
-continued
FD31
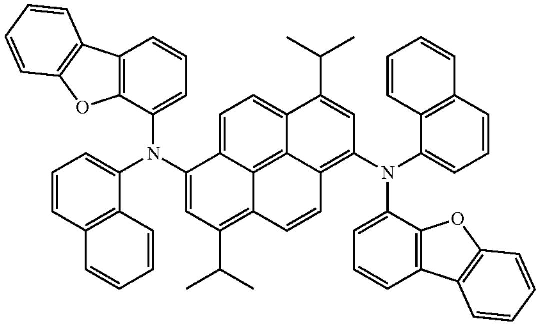
FD32
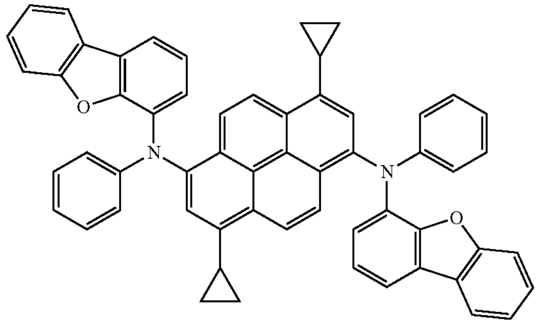
FD33
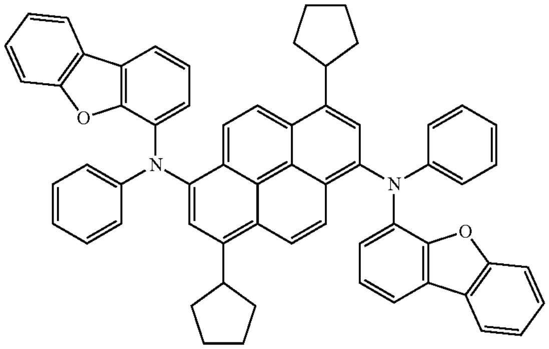
FD34
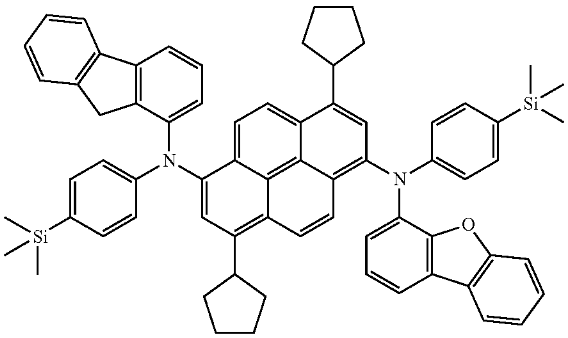

-continued

FD35

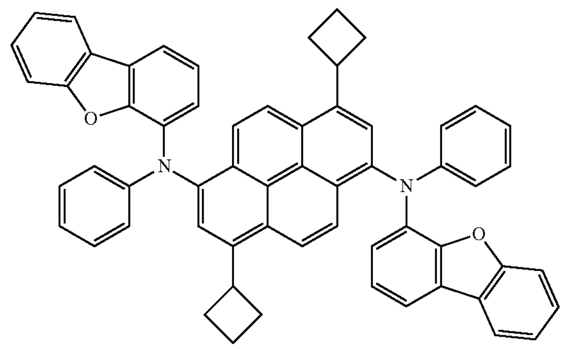

FD36

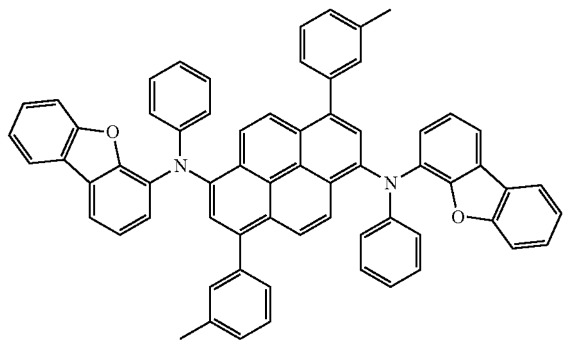

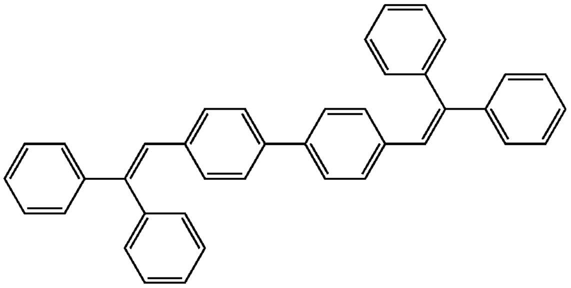

DPVBi

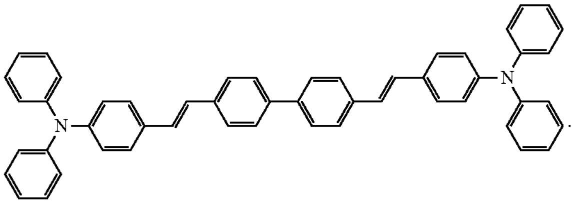

DPAVBi

[Electron Transport Region in Interlayer 130]

The electron transport region may have a structure consisting of a layer consisting of a single material, a structure consisting of a layer including different materials, or a multi-layered structure having layers including different materials.

The electron transport region may include a buffer layer, a hole blocking layer, an electron control layer, an electron transport layer, or an electron injection layer.

In embodiments, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein layers of each structure may be stacked on the emission layer in its respective stated order, but embodiments are not limited thereto.

The electron transport region (e.g., a buffer layer, a hole blocking layer, an electron control layer, or an electron transport layer in the electron transport region) may include a metal-free compound including at least one π electron-deficient nitrogen-containing $C_1$-$C_{60}$ cyclic group.

In embodiments, the electron transport region may include a compound represented by Formula 601:

$$[Ar_{601}]_{xe11}\text{-}[(L_{601})_{xe1}\text{-}R_{601}]_{xe21} \qquad \text{[Formula 601]}$$

In Formula 601, $Ar_{601}$ and $L_{601}$ may each independently be a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xe11 may be 1, 2, or 3, xe1 may be 0, 1, 2, 3, 4, or 5, $R_{601}$ may be a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —$Si(Q_{601})(Q_{602})(Q_{603})$, —$C(=O)(Q_{601})$, —$S(=O)_2(Q_{601})$, or —$P(=O)(Q_{601})(Q_{602})$, $Q_{601}$ to $Q_{603}$ may each independently be the same as described in connection with $Q_1$ provided herein, xe21 may be 1, 2, 3, 4, or 5, and at least one of $Ar_{601}$, $L_{601}$, and $R_{601}$ may each independently be a π electron-deficient nitrogen-containing $C_1$-$C_{60}$ cyclic group unsubstituted or substituted with at least one $R_{10a}$.

In embodiments, when xe11 in Formula 601 is 2 or greater, at least two $Ar_{601}$ (s) may be bound via a single bond.

In embodiments, in Formula 601, $Ar_{601}$ may be a substituted or unsubstituted anthracene group.

In embodiments, the electron transport region may include a compound represented by Formula 601-1:

[Formula 601-1]

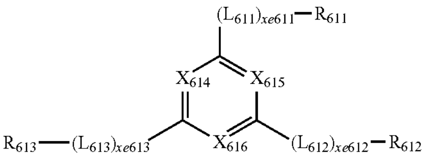

In Formula 601-1, $X_{614}$ may be N or $C(R_{614})$, $X_{615}$ may be N or $C(R_{615})$, $X_{616}$ may be N or $C(R_{616})$, and at least one of $X_{614}$ to $X_{616}$ may be N, $L_{611}$ to $L_{613}$ may each independently be the same as described in connection with $L_{601}$ provided herein, xe611 to xe613 may each independently be the same as described in connection with xe1 provided herein, $R_{611}$ to $R_{613}$ may each be understood by referring to the description of $R_{601}$ provided herein, and $R_{614}$ to $R_{616}$ may each independently be hydrogen, deuterium, —F, —Cl, —Br, —I, a hydroxyl group, a cyano group, a nitro group, a $C_1$-$C_{20}$ alkyl group, a $C_1$-$C_{20}$ alkoxy group, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$.

For example, in Formulae 601 and 601-1, xe1 and xe611 to xe613 may each independently be 0, 1, or 2.

The electron transport region may include one of Compounds ET1 to ET45, 2,9-dimethyl-4,7-diphenyl-1,10-phenanthroline (BCP), 4,7-diphenyl-1,10-phenanthroline (Bphen), $Alq_3$, BAlq, TAZ, NTAZ, TSPO1, TPBI, or any combination thereof:
ET1
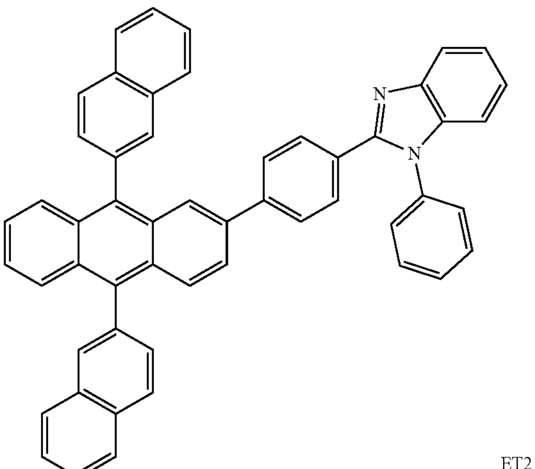
ET2
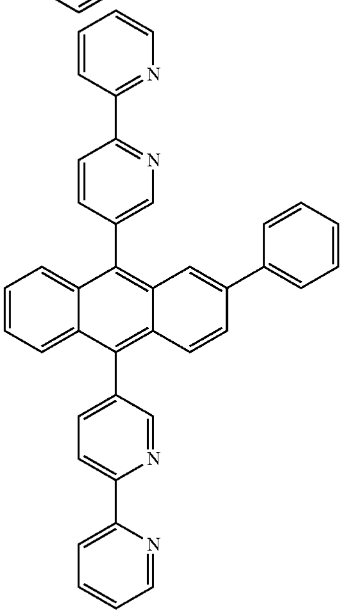
ET3
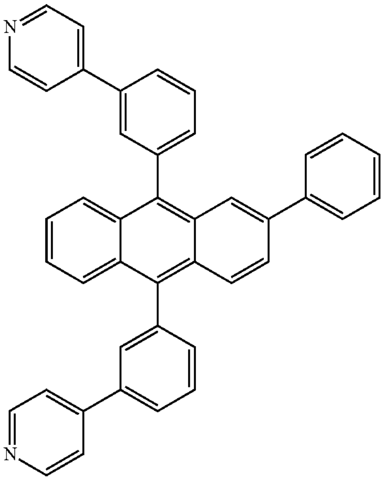
-continued
ET4
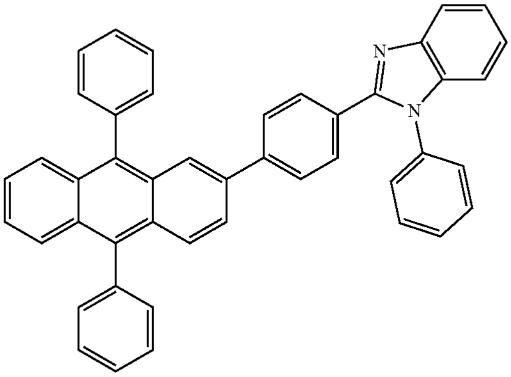
ET5
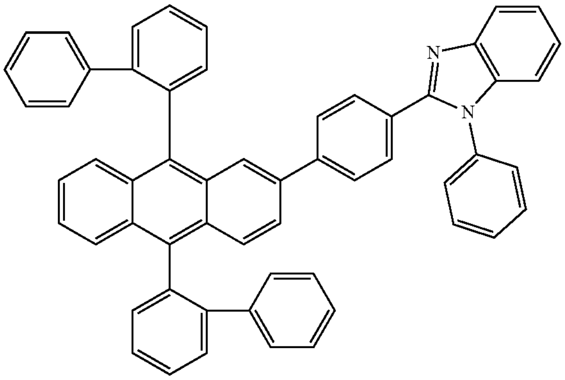
ET6
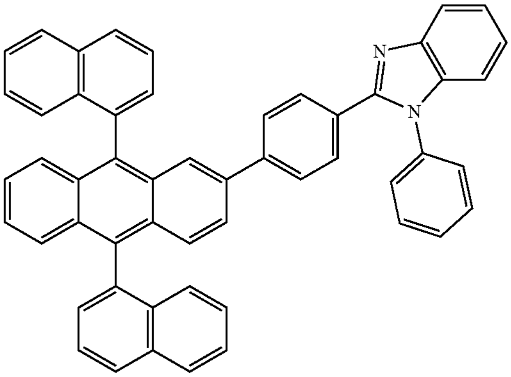

-continued
ET7
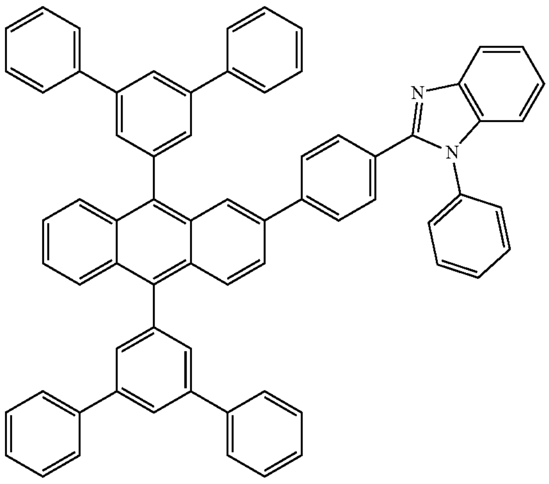
ET8
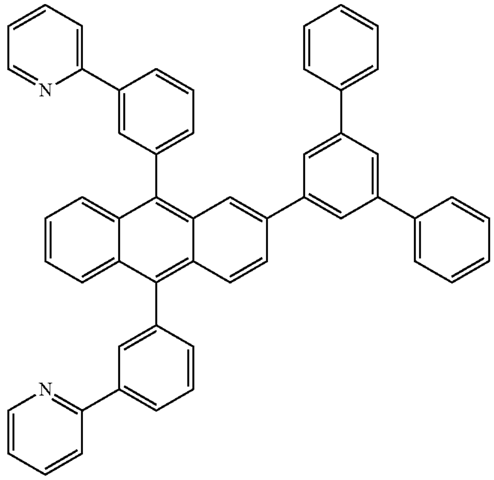
ET9
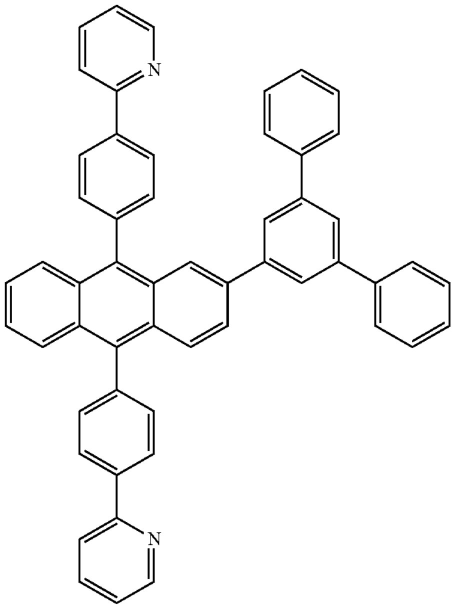
-continued
ET10
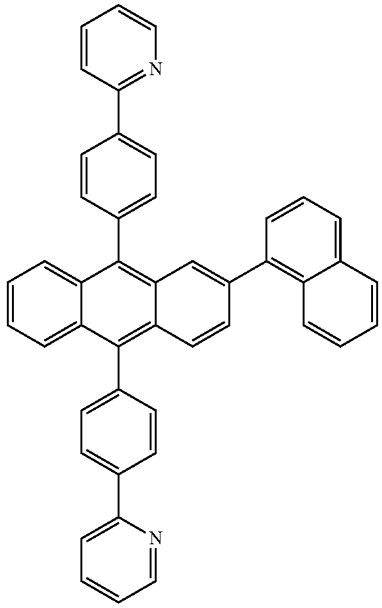
ET11
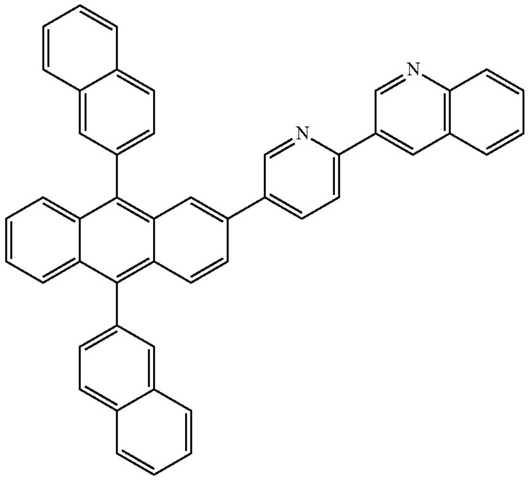
ET12
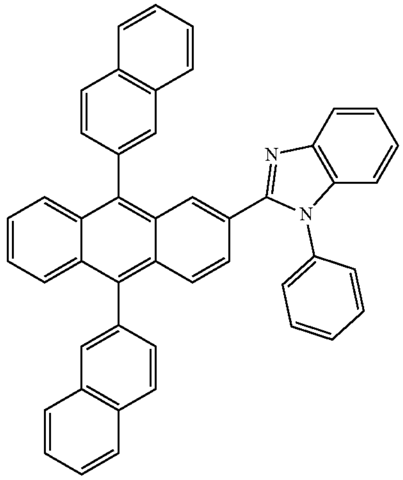

ET13
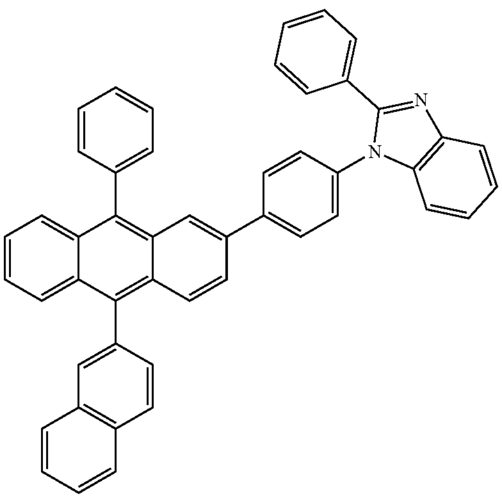
ET14
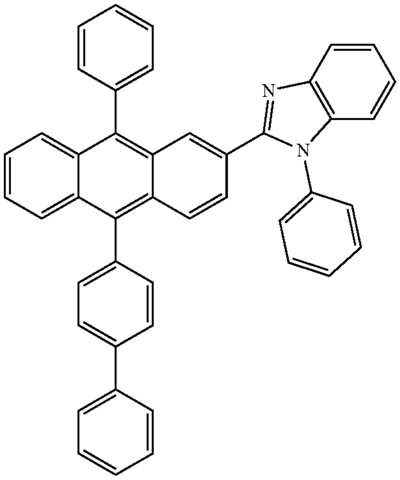
ET15
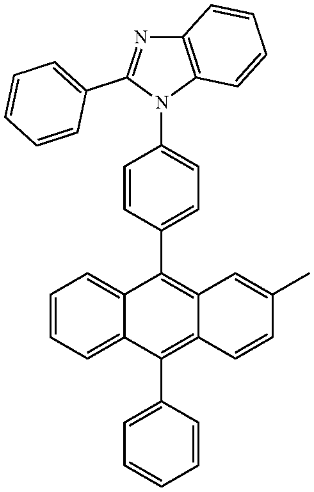
ET16
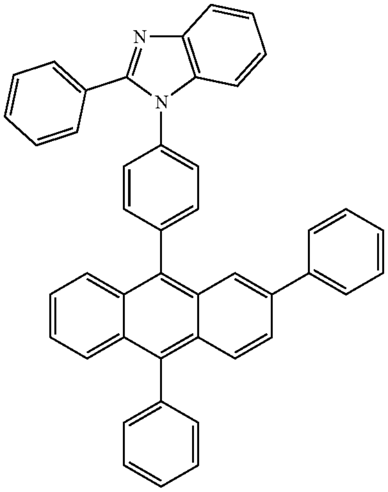
ET17
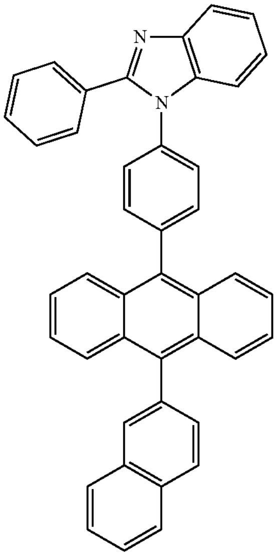
ET18
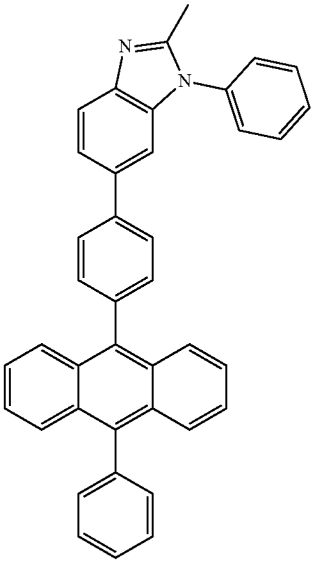

-continued
ET19
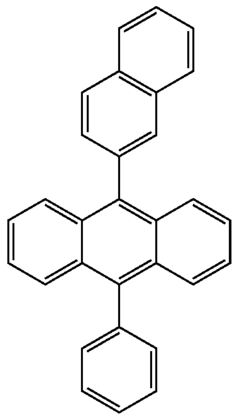
ET20
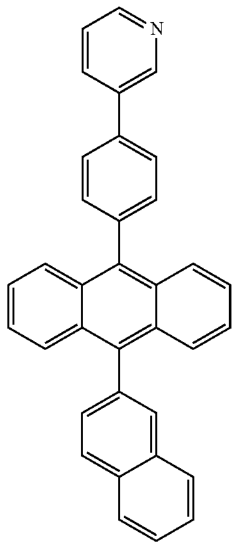
ET21
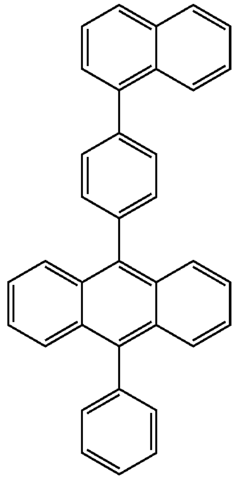
-continued
ET22
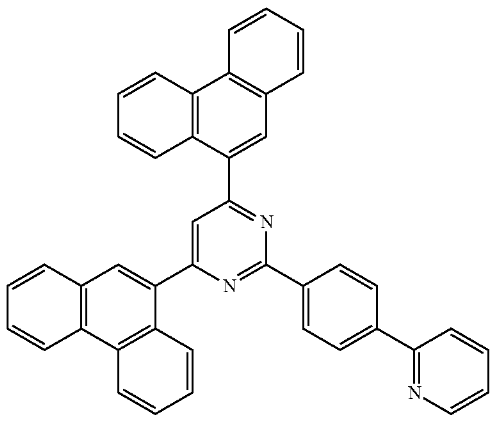
ET23
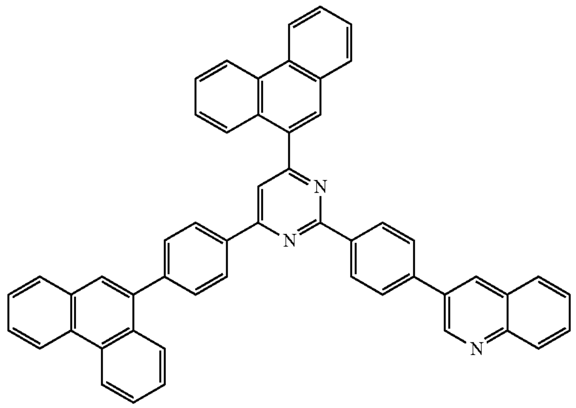
ET24
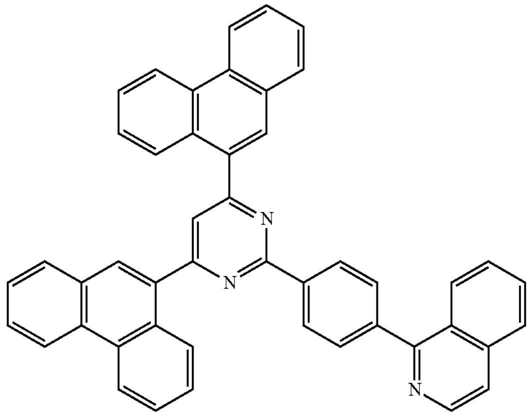

-continued
ET25
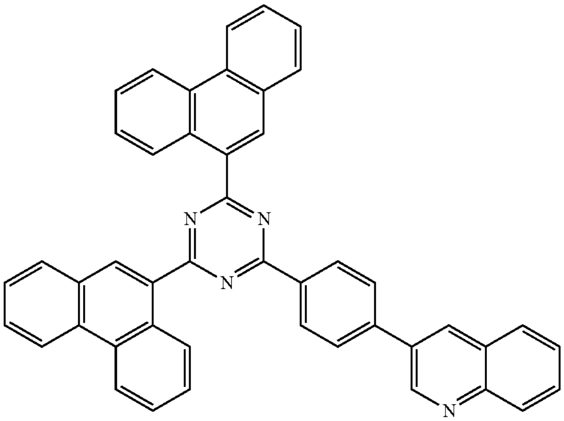
ET26
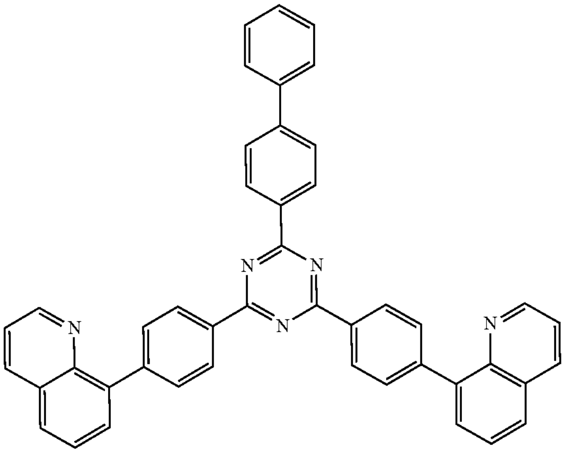
ET27
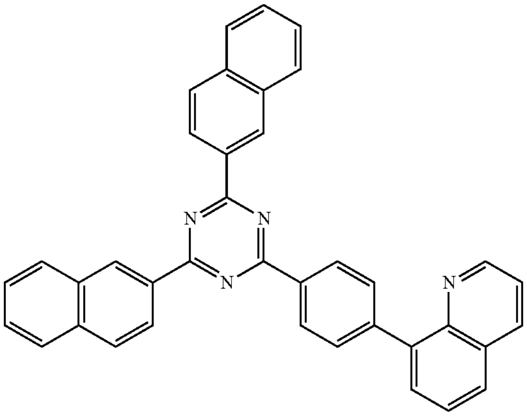
-continued
ET28
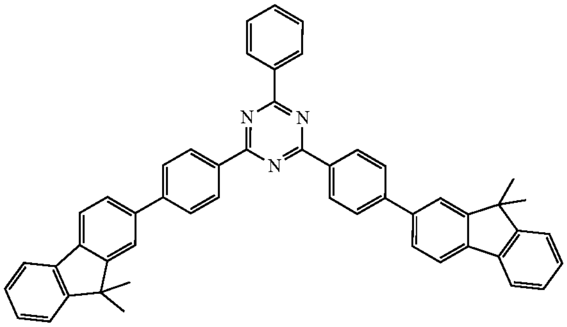
ET29
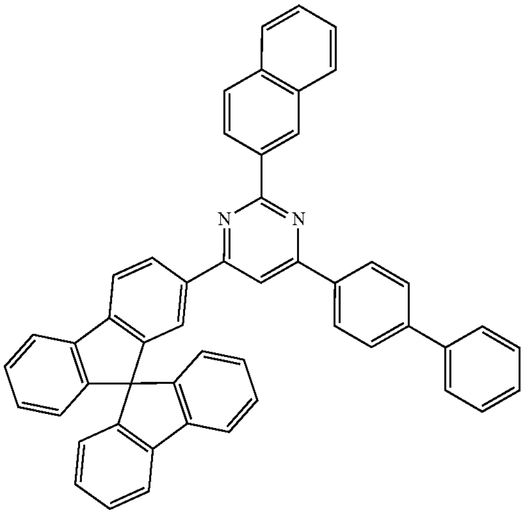
ET30
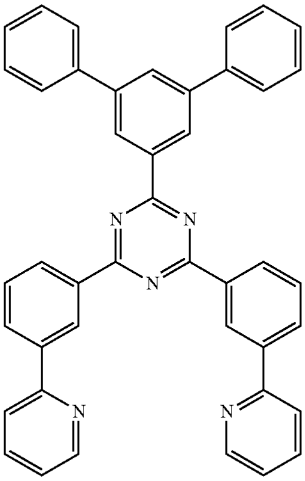

-continued
ET31
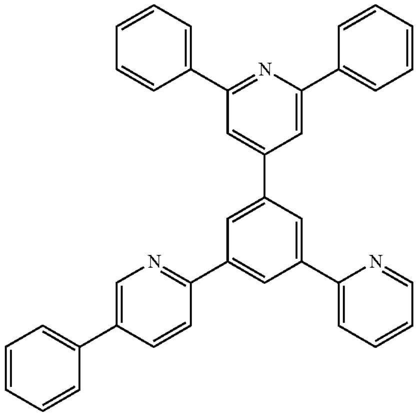
ET32
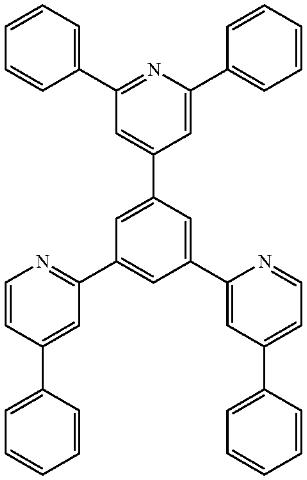
ET33
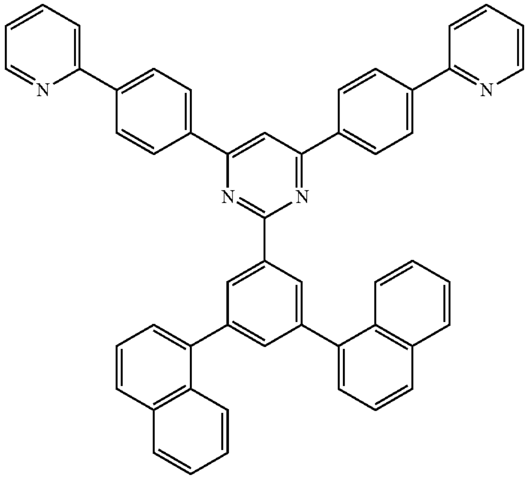
-continued
ET34
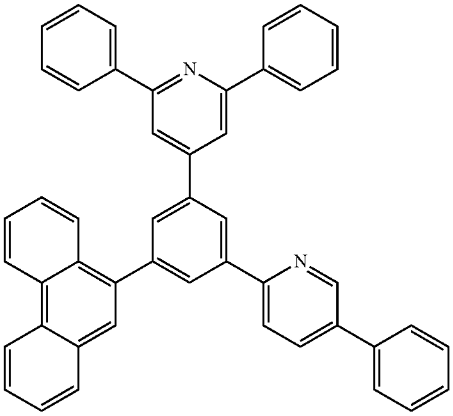
ET35
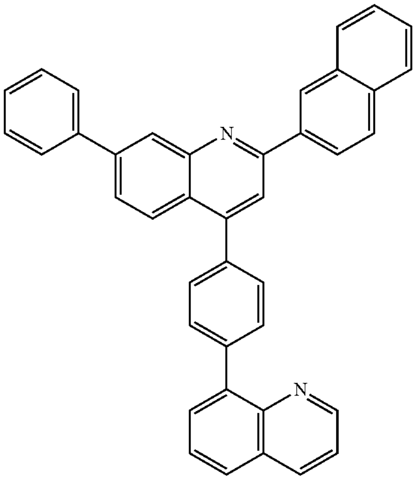
ET36
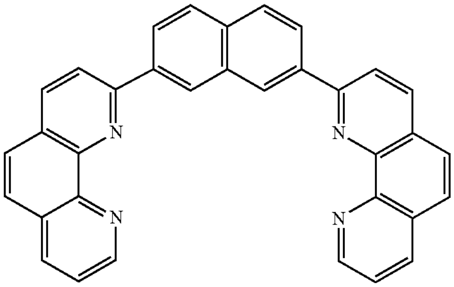
ET37
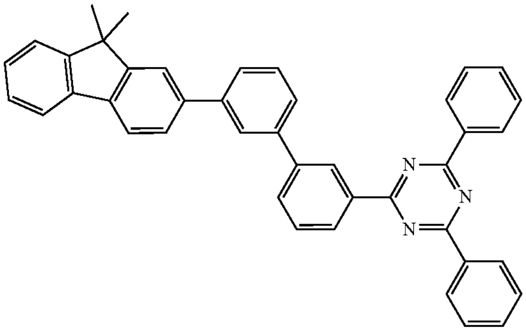

ET38
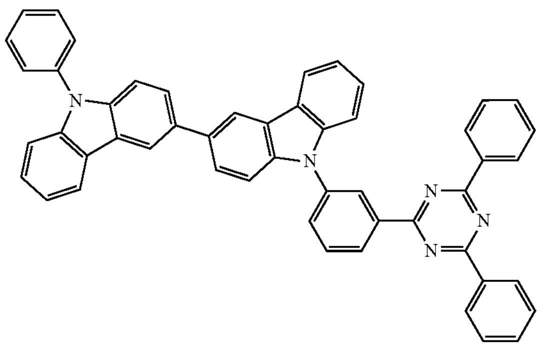
ET39
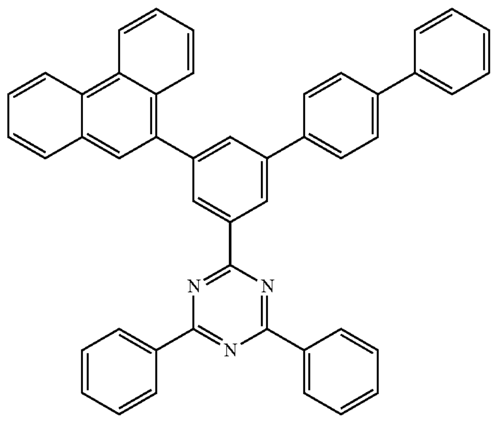
ET40
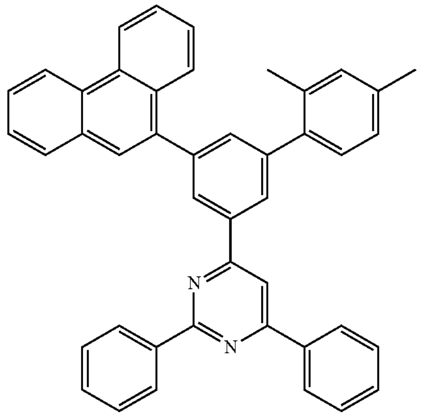
ET41
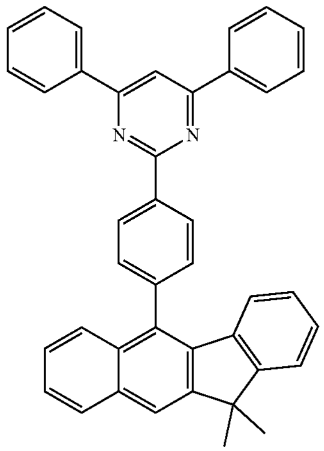
ET42
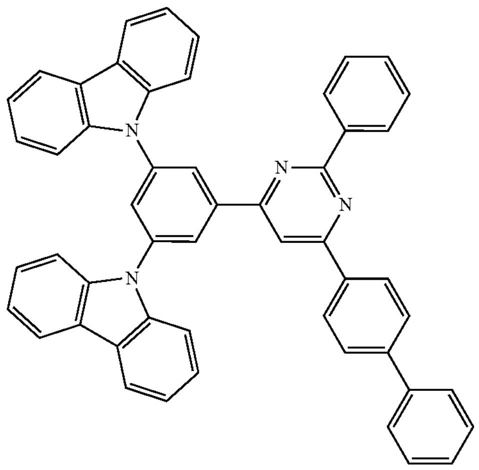
ET43
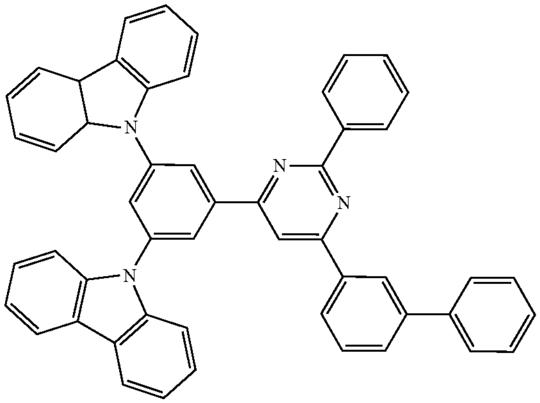

-continued

ET44

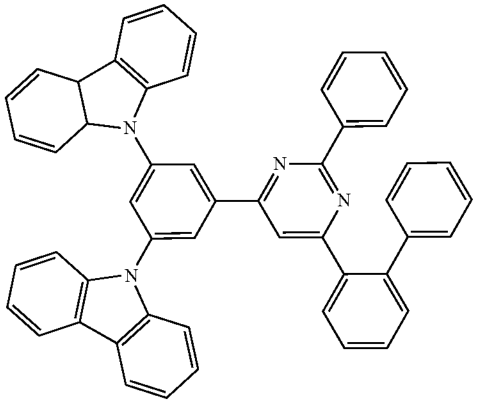

ET45

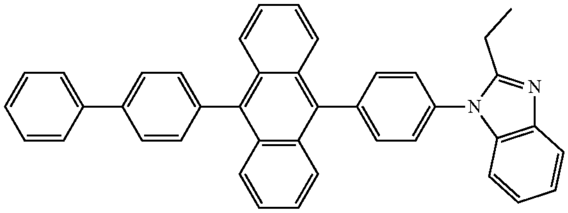

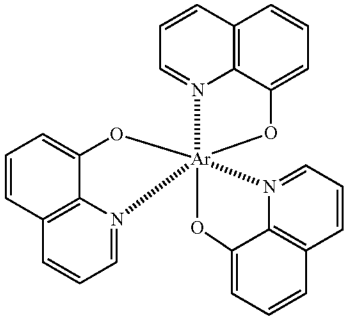

Alq3

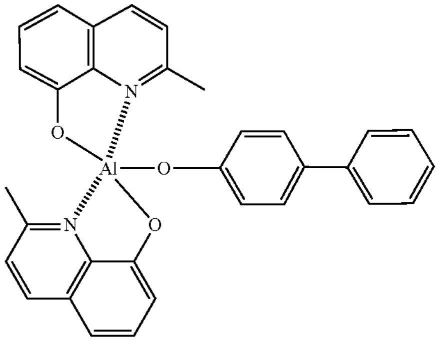

BAlq

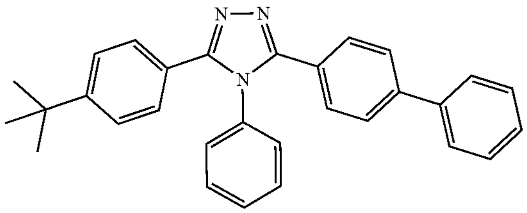

TAZ

-continued

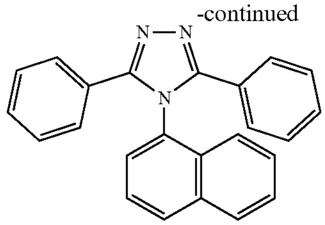

NTAZ

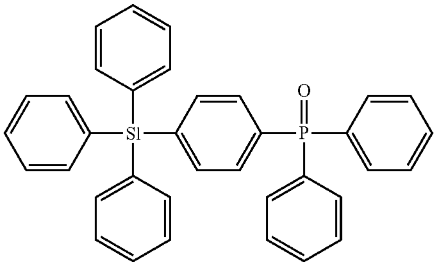

TSPO1

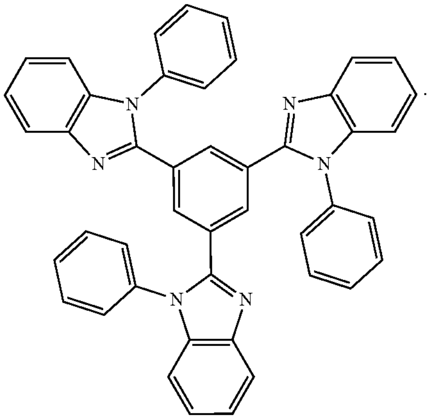

TPBI

A thickness of the electron transport region may be in a range of about 160 Angstroms (Å) to about 5,000 Å. For example, the thickness of the electron transport region may be in a range of about 100 Å to about 4,000 Å. When the electron transport region includes a buffer layer, a hole blocking layer, an electron control layer, an electron transport layer, or any combination thereof, a thickness of the buffer layer, the hole blocking layer, or the electron control layer may each independently be in a range of about 20 Å to about 1,000 Å, and a thickness of the electron transport layer may be in a range of about 100 Å to about 1,000 Å. For example, the thickness of the buffer layer, the hole blocking layer, or the electron control layer may each independently be in a range of about 30 Å to about 300 Å. For example, the thickness of the electron transport layer may be in a range of about 150 Å to about 500 Å. When the thicknesses of the buffer layer, the hole blocking layer, the electron control layer, and/or the electron transport layer are each within these ranges, excellent electron transport characteristics may be obtained without a substantial increase in driving voltage.

The electron transport region (for example, the electron transport layer in the electron transport region) may further include, in addition to the materials described above, a metal-containing material.

The metal-containing material may include an alkali metal complex, an alkaline earth metal complex, or any combination thereof. A metal ion of the alkali metal complex may be a lithium (Li) ion, a sodium (Na) ion, a potassium (K) ion, a rubidium (Rb) ion, or a cesium (Cs) ion. A metal ion of the alkaline earth metal complex may be a beryllium (Be) ion, a magnesium (Mg) ion, a calcium (Ca) ion, a strontium (Sr) ion, or a barium (Ba) ion. Each ligand coordinated with the metal ion of the alkali metal complex and the alkaline earth metal complex may independently include hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

For example, the metal-containing material may include a Li complex. The Li complex may include, e.g., Compound ET-D1 (LiQ) or Compound ET-D2:

ET-D1

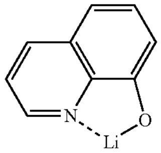

ET-D2

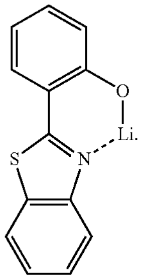

The electron transport region may include an electron injection layer that facilitates injection of electrons from the second electrode 150. The electron injection layer may directly contact the second electrode 150.

The electron injection layer may have a structure consisting of a layer consisting of a single material, a structure consisting of a layer including different materials, or a multi-layered structure having layers including different materials.

The electron injection layer may include an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof.

The alkali metal may include Li, Na, K, Rb, Cs or any combination thereof. The alkaline earth metal may include Mg, Ca, Sr, Ba, or any combination thereof. The rare earth metal may include Sc, Y, Ce, Tb, Yb, Gd, or any combination thereof.

The alkali metal-containing compound, the alkaline earth metal-containing compound, and the rare earth metal-containing compound may respectively be oxides, halides (e.g., fluorides, chlorides, bromides, or iodides), tellurides, or any combination thereof of each of the alkali metal, the alkaline earth metal, and the rare earth metal.

The alkali metal-containing compound may include alkali metal oxides such as $Li_2O$, $Cs_2O$, or $K_2O$, alkali metal halides such as LiF, NaF, CsF, KF, LiI, NaI, CsI, or KI, or any combination thereof. The alkaline earth-metal-containing compound may include alkaline earth-metal oxides, such as BaO, SrO, CaO, $BaxSr_{1-x}O$ (wherein x is a real number satisfying 0<x<1), or $Ba_xCa_{1-x}O$ (wherein x is a real number satisfying 0<x<1). The rare earth metal-containing compound may include $YbF_3$, $ScF_3$, $Sc_2O_3$, $Y_2O_3$, $Ce_2O_3$, $GdF_3$, $TbF_3$, $YbI_3$, $ScI_3$, $TbI_3$, or any combination thereof. In embodiments, the rare earth metal-containing compound may include a lanthanide metal telluride. Examples of the lanthanide metal telluride may include LaTe, CeTe, PrTe, NdTe, PmTe, SmTe, EuTe, GdTe, TbTe, DyTe, HoTe, ErTe, TmTe, YbTe, LuTe, $La_2Te_3$, $Ce_2Te_3$, $Pr_2Te_3$, $Nd_2Te_3$, $Pm_2Te_3$, $Sm_2Te_3$, $Eu_2Te_3$, $Gd_2Te_3$, $Tb_2Te_3$, $Dy_2Te_3$, $Ho_2Te_3$, $Er_2Te_3$, $Tm_2Te_3$, $Yb_2Te_3$, $Lu_2Te_3$, and the like.

The alkali metal complex, the alkaline earth metal complex, and the rare earth metal complex may include one of ions of the alkali metal, ions of the alkaline earth metal, and ions of the rare earth metal described above, and a ligand bonded to the metal ion, e.g., hydroxyquinoline, hydroxyisoquinoline, hydroxybenzoquinoline, hydroxyacridine, hydroxyphenanthridine, hydroxyphenyloxazole, hydroxyphenylthiazole, hydroxyphenyloxadiazole, hydroxyphenylthiadiazole, hydroxyphenylpyridine, hydroxyphenylbenzimidazole, hydroxyphenylbenzothiazole, bipyridine, phenanthroline, cyclopentadiene, or any combination thereof.

The electron injection layer may consist of an alkali metal, an alkaline earth metal, a rare earth metal, an alkali metal-containing compound, an alkaline earth metal-containing compound, a rare earth metal-containing compound, an alkali metal complex, an alkaline earth metal complex, a rare earth metal complex, or any combination thereof, as described above. In embodiments, the electron injection layer may further include an organic material (e.g., a compound represented by Formula 601).

In embodiments, the electron injection layer may consist of an alkali metal-containing compound (e.g., alkali metal halide); or may consist of an alkali metal-containing compound (e.g., alkali metal halide), and an alkali metal, an alkaline earth metal, a rare earth metal, or any combination thereof. In embodiments, the electron injection layer may be a KI:Yb co-deposition layer, a RbI:Yb co-deposition layer, and the like.

When the electron injection layer further includes an organic material, an alkali metal, an alkaline earth metal, a rare earth metal, an alkali metal-containing compound, an alkaline earth metal-containing compound, rare earth metal-containing compound, an alkali metal complex, an alkaline earth metal complex, a rare earth metal complex, or any combination thereof may be homogeneously or non-homogeneously dispersed in a matrix including the organic material.

A thickness of the electron injection layer may be in a range of about 1 Å to about 100 Å. For example, the thickness of the electron injection layer may be in a range of about 3 Å to about 90 Å. When the thickness of the electron injection layer is within any of these ranges, excellent electron injection characteristics may be obtained without a substantial increase in driving voltage.

[Second Electrode 150]

The second electrode 150 may be on the interlayer 130. In an embodiment, the second electrode 150 may be a cathode that is an electron injection electrode. A material for forming the second electrode 150 may be a material having a low work function, for example, a metal, an alloy, an electrically conductive compound, or any combination thereof.

The second electrode 150 may include lithium (Li), silver (Ag), magnesium (Mg), aluminum (Al), aluminum-lithium (Al—Li), calcium (Ca), magnesium-indium (Mg—In), magnesium-silver (Mg—Ag), ytterbium (Yb), silver-ytterbium (Ag—Yb), ITO, IZO, or any combination thereof. The second electrode 150 may be a transmissive electrode, a semi-transmissive electrode, or a reflective electrode.

The second electrode 150 may have a single-layered structure, or a structure including two or more layers.

[Capping Layer]

A first capping layer may be located outside the first electrode 110, and/or a second capping layer may be located outside the second electrode 150. In embodiments, the light-emitting device 10 may have a structure in which the first capping layer, the first electrode 110, the interlayer 130, and the second electrode 150 are stacked in this stated order, a structure in which the first electrode 110, the interlayer 130, the second electrode 150, and the second capping layer are stacked in this stated order, or a structure in which the first capping layer, the first electrode 110, the interlayer 130, the second electrode 150, and the second capping layer are stacked in this stated order.

In the light-emitting device 10, light emitted from the emission layer in the interlayer 130 may pass through the first electrode 110 (which may be a semi-transmissive electrode or a transmissive electrode) and through the first capping layer to the outside. In the light-emitting device 10, light emitted from the emission layer in the interlayer 130 may pass through the second electrode 150 (which may be a semi-transmissive electrode or a transmissive electrode) and through the second capping layer to the outside.

The first capping layer and the second capping layer may each improve the external luminescence efficiency based on the principle of constructive interference. Accordingly, the optical extraction efficiency of the light-emitting device 10 may be increased, thus improving the luminescence efficiency of the light-emitting device 10.

The first capping layer and the second capping layer may each include a material having a refractive index equal to or greater than about 1.6 (at a wavelength of about 589 nm).

The first capping layer and the second capping layer may each independently be a capping layer including an organic material, a capping layer including an inorganic material, or an organic-inorganic composite capping layer including an organic material and an inorganic material.

At least one of the first capping layer and the second capping layer may each independently include carbocyclic compounds, heterocyclic compounds, amine group-containing compounds, porphine derivatives, phthalocyanine derivatives, naphthalocyanine derivatives, alkali metal complexes, alkaline earth metal complexes, or any combination thereof. The carbocyclic compound, the heterocyclic compound, and the amine group-containing compound may each independently be optionally substituted with a substituent of O, N, S, Se, Si, F, Cl, Br, I, or any combination thereof.

In embodiments, at least one of the first capping layer and the second capping layer may each independently include an amine group-containing compound.

In embodiments, at least one of the first capping layer and the second capping layer may each independently include the compound represented by Formula 201, the compound represented by Formula 202, or any combination thereof.

In embodiments, at least one of the first capping layer and the second capping layer may each independently include one of Compounds HT28 to HT33, one of Compounds CPI to CP6, β-NPB, or any combination thereof:

CP1

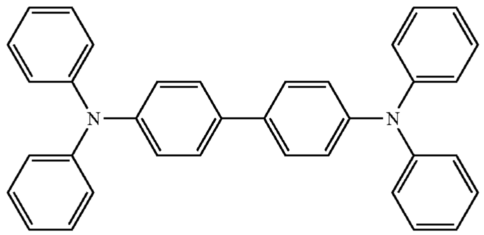

CP2

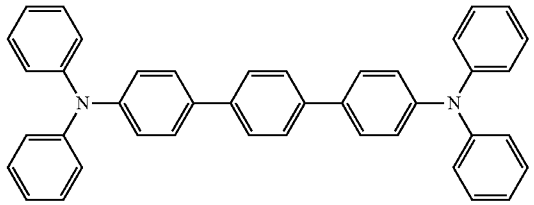

CP3

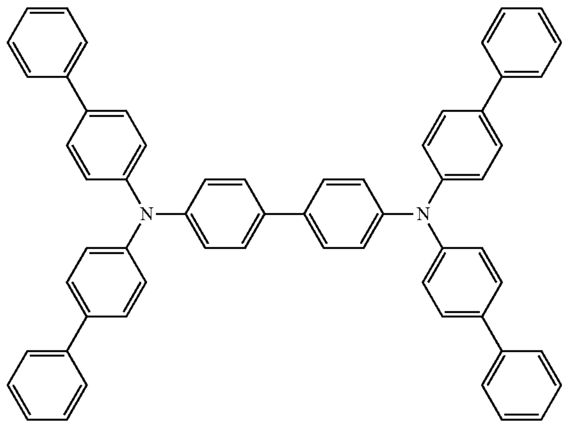

CP4

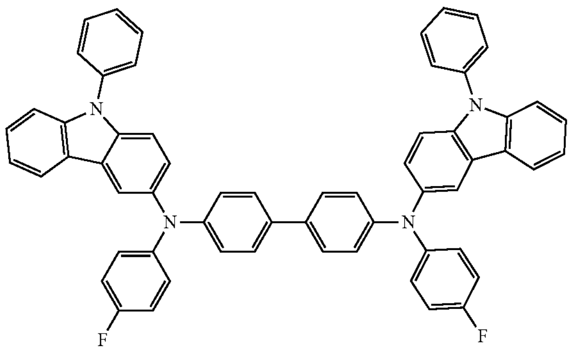

-continued

CP5

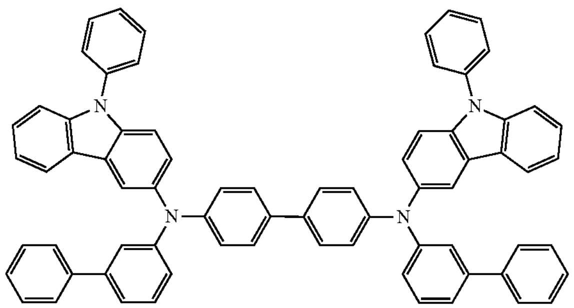

CP6

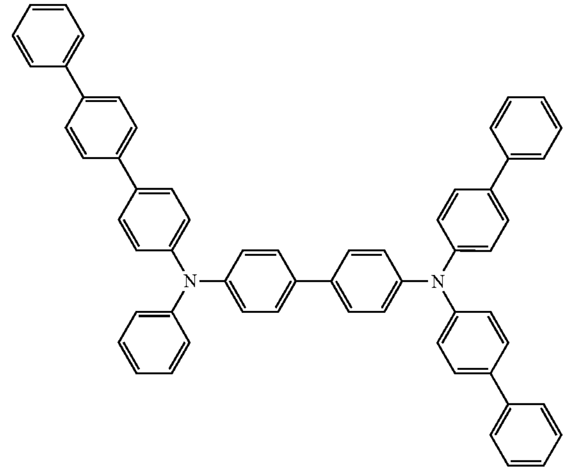

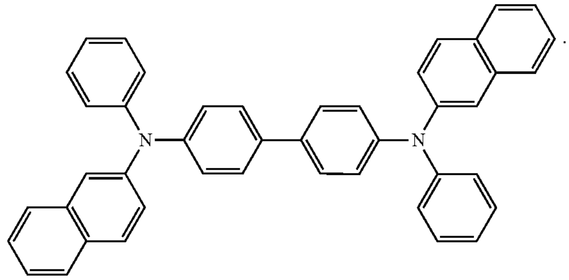

β-NPB

[Electronic Apparatus]

The light-emitting device may be included in various electronic apparatuses. In embodiments, an electronic apparatus including the light-emitting device may be an emission apparatus or an authentication apparatus.

The electronic apparatus (e.g., an emission apparatus) may further include, in addition to the light-emitting device, a color filter, a color-conversion layer, or a color filter and a color-conversion layer. The color filter and/or the color-conversion layer may be disposed on at least one traveling direction of light emitted from the light-emitting device. For example, light emitted from the light-emitting device may be blue light or white light. The light-emitting device may be understood by referring to the descriptions provided herein. In embodiments, the color-conversion layer may include quantum dots. The quantum dot may be, for example, the quantum dot described herein.

The electronic apparatus may include a first substrate. The first substrate may include subpixels, the color filter may include color filter areas respectively corresponding to the subpixels, and the color-conversion layer may include color-conversion areas respectively corresponding to the subpixels.

A pixel-defining film may be located between the subpixels to define each subpixel.

The color filter may further include color filter areas and light-blocking patterns between the color filter areas, and the color-conversion layer may further include color-conversion areas and light-blocking patterns between the color-conversion areas.

The color filter areas (or the color-conversion areas) may include a first area emitting first color light; a second area emitting second color light; and/or a third area emitting third color light, and the first color light, the second color light, and/or the third color light may have different maximum emission wavelengths. In embodiments, the first color light may be red light, the second color light may be green light, and the third color light may be blue light. In embodiments, the color filter areas (or the color-conversion areas) may each include quantum dots. In embodiments, the first area may include red quantum dots, the second area may include green quantum dots, and the third area may not include a quantum dot. The quantum dot may be understood by referring to the description of the quantum dot provided herein. The first area, the second area, and/or the third area may each further include a scatterer.

In embodiments, the light-emitting device may emit first light, the first area may absorb the first light to emit 1-1 color light, the second area may absorb the first light to emit 2-1 color light, and the third area may absorb the first light to emit 3-1 color light. In this embodiment, the 1-1 color light, the 2-1 color light, and the 3-1 color light may each have a different maximum emission wavelength from one another. In embodiments, the first light may be blue light, the 1-1 color light may be red light, the 2-1 color light may be green light, and the 3-1 light may be blue light.

The electronic apparatus may further include a thin-film transistor, in addition to the light-emitting device. The thin-film transistor may include a source electrode, a drain electrode, and an active layer, wherein one of the source electrode and the drain electrode may be electrically connected to at least one of the first electrode and the second electrode of the light-emitting device.

The thin-film transistor may further include a gate electrode, a gate insulating film, or the like.

The active layer may include a crystalline silicon, an amorphous silicon, an organic semiconductor, an oxide semiconductor, or the like.

The electronic apparatus may further include an encapsulation unit for sealing the light-emitting device. The encapsulation unit may be located between the color filter and/or the color-conversion layer and the light-emitting device. The encapsulation unit may allow light to pass to the outside from the light-emitting device and may prevent air and/or moisture from permeating into the light-emitting device at the same time. The encapsulation unit may be a sealing substrate including a transparent glass or a plastic substrate. The encapsulation unit may be a thin-film encapsulating layer including at least one of an organic layer and/or an inorganic layer. When the encapsulation unit is a thin-film encapsulating layer, the electronic apparatus may be flexible.

Various functional layers may be disposed on the encapsulation unit depending on the use of an electronic apparatus. Examples of the functional layer may include a touch screen layer, a polarization layer, an authentication apparatus, or the like. The touch screen layer may be a resistive touch screen layer, a capacitive touch screen layer, or an infrared beam touch screen layer. The authentication apparatus may be, for example, a biometric authentication apparatus that identifies an individual according to biometric information (e.g., a fingertip, a pupil, or the like).

The authentication apparatus may further include a biometric information collecting unit, in addition to the light-emitting device described above.

The electronic apparatus may be applicable to various displays, such as an optical source, lighting, a personal computer (e.g., a mobile personal computer), a cellphone, a digital camera, an electronic note, an electronic dictionary, an electronic game console, a medical device (e.g., an electronic thermometer, a blood pressure meter, a glucometer, a pulse measuring device, a pulse wave measuring device, an electrocardiogram ultrasonic diagnosis device, or an endoscope display device), a fish finder, various measurement devices, gauges (e.g., gauges of an automobile, an airplane, or a ship), and a projector.

Figure 2:
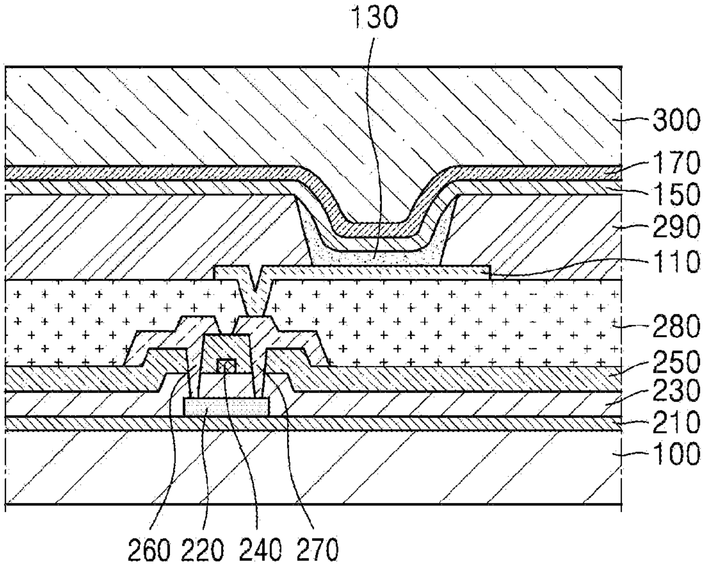
FIG. 2 is a schematic cross-sectional view of an electronic apparatus according to an embodiment.
Figure 3:
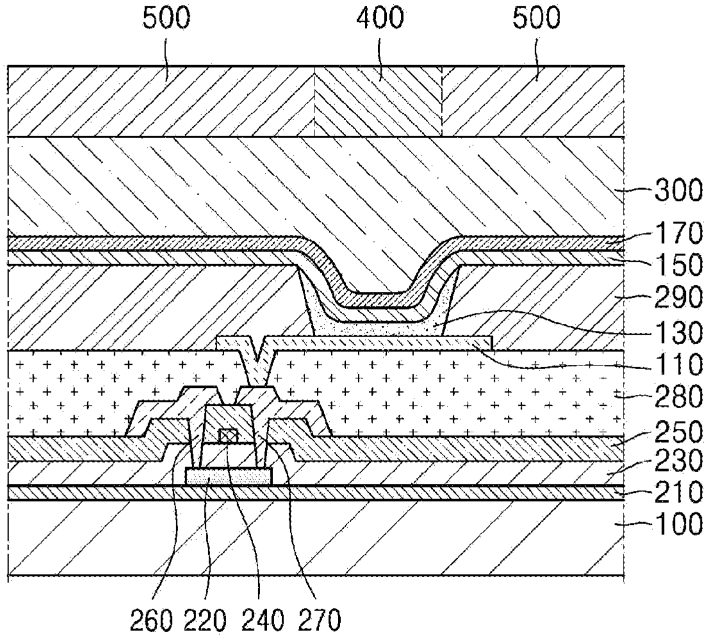
FIG. 3 is a schematic cross-sectional view of an electronic apparatus according to another embodiment.

Descriptions of FIGS. 2 and 3

FIG. 2 is a schematic cross-sectional view of an electronic apparatus according to an embodiment.

The electronic apparatus in FIG. 2 may include a substrate 100, a thin-film transistor, a light-emitting device, and an encapsulation unit 300 sealing the light-emitting device.

The substrate 100 may be a flexible substrate, a glass substrate, or a metal substrate. A buffer layer 210 may be on the substrate 100. The buffer layer 210 may prevent penetration of impurities through the substrate 100 and may provide a flat surface on the substrate 100.

A thin-film transistor may be on the buffer layer 210. The thin-film transistor may include an active layer 220, a gate electrode 240, a source electrode 260, and a drain electrode 270.

The active layer 220 may include an inorganic semiconductor such as silicon or polysilicon, an organic semiconductor, or an oxide semiconductor and may include a source area, a drain area, and a channel area.

A gate insulating film 230 for insulating the active layer 220 and the gate electrode 240 may be on the active layer 220, and the gate electrode 240 may be on the gate insulating film 230.

An interlayer insulating film 250 may be on the gate electrode 240. The interlayer insulating film 250 may be between the gate electrode 240 and the source electrode 260 and between the gate electrode 240 and the drain electrode 270 to provide insulation therebetween.

The source electrode 260 and the drain electrode 270 may be on the interlayer insulating film 250. The interlayer insulating film 250 and the gate insulating film 230 may be formed to expose the source area and the drain area of the active layer 220, and the source electrode 260 and the drain electrode 270 may be adjacent to the exposed source area and the exposed drain area of the active layer 220.

The thin-film transistor may be electrically connected to a light-emitting device to drive the light-emitting device and may be protected by a passivation layer 280. The passivation layer 280 may include an inorganic insulating film, an organic insulating film, or a combination thereof. A light-emitting device may be on the passivation layer 280. The light-emitting device may include a first electrode 110, an interlayer 130, and a second electrode 150.

The first electrode 110 may be on the passivation layer 280. The passivation layer 280 may not fully cover the drain electrode 270 and may expose a specific area of the drain electrode 270, and the first electrode 110 may be electrically connected to the exposed area of the drain electrode 270.

A pixel-defining film 290 may be on the first electrode 110. The pixel-defining film 290 may expose a specific area of the first electrode 110, and the interlayer 130 may be formed in the exposed area. The pixel-defining film 290 may be a polyimide or polyacryl organic film. Although it is not shown in FIG. 2, at least some layers of the interlayer 130 may extend to the upper portion of the pixel-defining film 290 and may be provided in the form of a common layer.

The second electrode 150 may be on the interlayer 130, and a capping layer 170 may be additionally formed on the second electrode 150. The capping layer 170 may be formed to cover the second electrode 150.

The encapsulation unit 300 may be on the capping layer 170. The encapsulation unit 300 may be on the light-emitting device to protect a light-emitting device from moisture and/or oxygen. The encapsulation unit 300 may include an inorganic film including silicon nitride ($SiN_x$), silicon oxide ($SiO_x$), indium tin oxide, indium zinc oxide, or any combination thereof; an organic film including PET, polyethylene naphthalate, polycarbonate, polyimide, polyethylene sulfonate, polyoxy methylene, poly arylate, hexamethyl disiloxane, an acrylic resin (e.g., polymethyl methacrylate, polyacrylic acid, and the like), an epoxy resin (e.g., aliphatic glycidyl ether (AGE) and the like), or any combination thereof; or a combination of the inorganic film and the organic film.

FIG. 3 is a schematic cross-sectional view of another electronic apparatus according to an embodiment.

The electronic apparatus shown in FIG. 3 may be substantially identical to the electronic apparatus shown in FIG. 2, except that a light-shielding pattern 500 and a functional area 400 are additionally located on the encapsulation unit 300. The functional area 400 may be a color filter area, a color-conversion area, or a combination of a color filter area and a color-conversion area. In embodiments, the light-emitting device shown in FIG. 3 included in the electronic apparatus may be a tandem light-emitting device.

[Manufacturing Method]

The layers constituting the hole transport region, the emission layer, and the layers constituting the electron transport region may be formed in a specific region by using suitable methods such as vacuum deposition, spin coating, casting, Langmuir-Blodgett (LB) deposition, ink-jet printing, laser printing, and laser-induced thermal imaging.

When layers constituting the hole transport region, an emission layer, and layers constituting the electron transport region are each independently formed by vacuum-deposition, the vacuum-deposition may be performed at a deposition temperature in a range of about 100° C. to about 500° C., at a vacuum degree in a range of about 10-8 torr to about 10-3 torr, and at a deposition rate in a range of about 0.01 Angstroms per second (Å/sec) to about 100 Å/sec, depending on the material to be included in each layer and the structure of each layer to be formed.

Definitions of Terms

The term "$C_3$-$C_{60}$ carbocyclic group" as used herein may be a cyclic group consisting only of carbon atoms as ring-forming atoms and having 3 to 60 carbon atoms. The term "$C_1$-$C_{60}$ heterocyclic group" as used herein may be a cyclic group having 1 to 60 carbon atoms in addition to at least one heteroatom as ring-forming atoms other than carbon atoms. The $C_3$-$C_{60}$ carbocyclic group and the $C_1$-$C_{60}$ heterocyclic group may each be a monocyclic group consisting of one ring or a polycyclic group in which at least two rings are condensed. For example, the number of ring-forming atoms in the $C_1$-$C_{60}$ heterocyclic group may be in a range of 3 to 61.

The term "cyclic group" as used herein may include the $C_3$-$C_{60}$ carbocyclic group and the $C_1$-$C_{60}$ heterocyclic group.

The term "π electron-rich $C_3$-$C_{60}$ cyclic group" as used herein may be a cyclic group having 3 to 60 carbon atoms and may not include *—N=*' as a ring-forming moiety. The term "π electron-deficient nitrogen-containing $C_1$-$C_{60}$ cyclic group" as used herein may be a heterocyclic group having 1 to 60 carbon atoms and may include *—N=*' as a ring-forming moiety.

In embodiments, the $C_3$-$C_{60}$ carbocyclic group may be a T1 group or a group in which at least two T1 groups are condensed (for example, a cyclopentadiene group, an adamantane group, a norbornane group, a benzene group, a pentalene group, a naphthalene group, an azulene group, an indacene group, an acenaphthylene group, a phenalene group, a phenanthrene group, an anthracene group, a fluoranthene group, a triphenylene group, a pyrene group, a chrysene group, a perylene group, a pentaphene group, a heptalene group, a naphthacene group, a picene group, a hexacene group, a pentacene group, a rubicene group, a coronene group, an ovalene group, an indene group, a fluorene group, a spiro-bifluorene group, a benzofluorene group, an indenophenanthrene group, or an indenoanthracene group), the $C_1$-$C_{60}$ heterocyclic group may be a T2 group, a group in which at least two T2 groups are condensed, or a group in which at least one T2 group is condensed with at least one T1 group (for example, a pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonapthothiophene group, a benzonaphthosilole group, a benzofurodibenzofuran group, a benzofurodibenzothiophene group, a benzothienodibenzothiophene group, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and the like), the π electron-rich $C_3$-$C_{60}$ cyclic group may be a T1 group, a condensed group in which at least two T1 groups are condensed, a T3 group, a condensed group in which at least two T3 groups are condensed, or a condensed group in which at least one T3 group is condensed with at least one T1 group (for example, a $C_3$-$C_{60}$ carbocyclic group, a 1H-pyrrole group, a silole group, a borole group, a 2H-pyrrole group, a 3H-pyrrole group, a thiophene group, a furan group, an indole group, a benzoindole group, a naphthoindole group, an isoindole group, a benzoisoindole group, a naphthoisoindole group, a benzosilole group, a benzothiophene group, a benzofuran group, a carbazole group, a dibenzosilole group, a dibenzothiophene group, a dibenzofuran group, an indenocarbazole group, an indolocarbazole group, a benzofurocarbazole group, a benzothienocarbazole group, a benzosilolocarbazole group, a benzoindolocarbazole group, a benzocarbazole group, a benzonaphthofuran group, a benzonapthothiophene group, a benzonaphthosilole group, a benzofurodibenzofuran group, a benzofurodibenzothiophene group, a benzothienodibenzothiophene group, and the like), and the π electron-deficient nitrogen-containing $C_1$-$C_{60}$ cyclic group may be a T4 group, a group in which at least two T4 groups are condensed, a group in which at least one T4 group is condensed with at least one T1 group, a group in which at least one T4 group is condensed with at least one T3 group, or a group in which at least one T4 group, at least one T1 group, and at least one T3 group are condensed (for example, a pyrazole group, an imidazole group, a triazole group, an oxazole group, an isoxazole group, an oxadiazole group, a thiazole group, an isothiazole group, a thiadiazole group, a benzopyrazole group, a benzimidazole group, a benzoxazole group, a benzoisoxazole group, a benzothiazole group, a benzoisothiazole group, a pyridine group, a pyrimidine group, a pyrazine group, a pyridazine group, a triazine group, a quinoline group, an isoquinoline group, a benzoquinoline group, a benzoisoquinoline group, a quinoxaline group, a benzoquinoxaline group, a quinazoline group, a benzoquinazoline group, a phenanthroline group, a cinnoline group, a phthalazine group, a naphthyridine group, an imidazopyridine group, an imidazopyrimidine group, an imidazotriazine group, an imidazopyrazine group, an imidazopyridazine group, an azacarbazole group, an azafluorene group, an azadibenzosilole group, an azadibenzothiophene group, an azadibenzofuran group, and the like), wherein the T1 group may be a cyclopropane group, a cyclobutane group, a cyclopentane group, a cyclohexane group, a cycloheptane group, a cyclooctane group, a cyclobutene group, a cyclopentene group, a cyclopentadiene group, a cyclohexene group, a cyclohexadiene group, a cycloheptene group, an adamantane group, a norbornane (or bicyclo[2.2.1]heptane) group, a norbornene group, a bicyclo[1.1.1]pentane group, a bicyclo[2.1.1]hexane group, a bicyclo[2.2.2]octane group, or a benzene group, the T2 group may be a furan group, a thiophene group, a 1H-pyrrole group, a silole group, a borole group, a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, a tetrazine group, a pyrrolidine group, an imidazolidine group, a dihydropyrrole group, a piperidine group, a tetrahydropyridine group, a dihydropyridine group, a hexahydropyrimidine group, a tetrahydropyrimidine group, a dihydropyrimidine group, a piperazine group, a tetrahydropyrazine group, a dihydropyrazine group, a tetrahydropyridazine group, or a dihydropyridazine group, the T3 group may be a furan group, a thiophene group, a 1H-pyrrole group, a silole group, or a borole group, and the T4 group may be a 2H-pyrrole group, a 3H-pyrrole group, an imidazole group, a pyrazole group, a triazole group, a tetrazole group, an oxazole group, an isoxazole group, an oxadiazole group, a thiazole group, an isothiazole group, a thiadiazole group, an azasilole group, an azaborole group, a pyridine group, a pyrimidine group, a pyrazine group, a pyridazine group, a triazine group, or a tetrazine group.

The terms "cyclic group", "$C_3$-$C_{60}$ carbocyclic group", "$C_1$-$C_{60}$ heterocyclic group", "π electron-rich $C_3$-$C_{60}$ cyclic group", or "π electron-deficient nitrogen-containing $C_1$-$C_{60}$ cyclic group" as used herein may be a group condensed with any suitable cyclic group, a monovalent group, or a polyvalent group (e.g., a divalent group, a trivalent group, a tetravalent group, or the like), depending on the structure of the formula to which the term is applied. For example, a "benzene group" may be a benzene ring, a phenyl group, a phenylene group, or the like, and this may be understood by one of ordinary skill in the art, depending on the structure of the formula including the "benzene group".

Examples of the monovalent $C_3$-$C_{60}$ carbocyclic group and the monovalent $C_1$-$C_{60}$ heterocyclic group may include a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group. Examples of the divalent $C_3$-$C_{60}$ carbocyclic group and the monovalent $C_1$-$C_{60}$ heterocyclic group may include a $C_3$-$C_{10}$ cycloalkylene group, a $C_1$-$C_{10}$ heterocycloalkylene group, a $C_3$-$C_{10}$ cycloalkenylene group, a $C_1$-$C_{10}$ heterocycloalkenylene group, a $C_6$-$C_{60}$ arylene group, a $C_1$-$C_{60}$ heteroarylene group, a divalent non-aromatic condensed polycyclic group, and a substituted or unsubstituted divalent non-aromatic condensed heteropolycyclic group.

The term "$C_1$-$C_{60}$ alkyl group" as used herein may be a linear or branched aliphatic hydrocarbon monovalent group having 1 to 60 carbon atoms, and examples thereof may include a methyl group, an ethyl group, an n-propyl group, an iso-propyl group, an n-butyl group, a sec-butyl group, an isobutyl group, a tert-butyl group, an n-pentyl group, a tert-pentyl group, a neopentyl group, an isopentyl group, a sec-pentyl group, a 3-pentyl group, a sec-isopentyl group, an n-hexyl group, an iso-hexyl group, a sec-hexyl group, a tert-hexyl group, an n-heptyl group, an iso-heptyl group, a sec-heptyl group, a tert-heptyl group, an n-octyl group, an iso-octyl group, a sec-octyl group, a tert-octyl group, an n-nonyl group, an iso-nonyl group, a sec-nonyl group, a tert-nonyl group, an n-decyl group, an iso-decyl group, a sec-decyl group, and a tert-decyl group. The term "$C_1$-$C_{60}$ alkylene group" as used herein may be a divalent group having a same structure as the $C_1$-$C_{60}$ alkyl group.

The term "$C_2$-$C_{60}$ alkenyl group" as used herein may be a hydrocarbon group having at least one carbon-carbon double bond in the middle or at the terminus of the $C_2$-$C_{60}$ alkyl group. Examples thereof may include an ethenyl group, a propenyl group, and a butenyl group. The term "$C_2$-$C_{60}$ alkenylene group" as used herein may be a divalent group having a same structure as the $C_2$-$C_{60}$ alkenyl group.

The term "$C_2$-$C_{60}$ alkynyl group" as used herein may be a monovalent hydrocarbon group having at least one carbon-carbon triple bond in the middle or at the terminus of the $C_2$-$C_{60}$ alkyl group. Examples thereof may include an ethynyl group and a propynyl group. The term "$C_2$-$C_{60}$ alkynylene group" as used herein may be a divalent group having a same structure as the $C_2$-$C_{60}$ alkynyl group.

The term "$C_1$-$C_{60}$ alkoxy group" as used herein may be a monovalent group represented by —O($A_{101}$) (wherein $A_{101}$ is a $C_1$-$C_1$ alkyl group). Examples thereof may include a methoxy group, an ethoxy group, and an isopropyloxy group.

The term "$C_3$-$C_{10}$ cycloalkyl group" as used herein may be a monovalent saturated hydrocarbon monocyclic group including 3 to 10 carbon atoms. Examples of the $C_3$-$C_{10}$ cycloalkyl group may include a cyclopropyl group, a cyclobutyl group, a cyclopentyl group, a cyclohexyl group, a cycloheptyl group, a cyclooctyl group, an adamantanyl group, a norbornanyl (bicyclo[2.2.1]heptyl) group, a bicyclo[1.1.1]pentyl group, a bicyclo[2.1.1]hexyl group, or a bicyclo[2.2.2]octyl group. The term "$C_3$-$C_{10}$ cycloalkylene group" as used herein may be a divalent group having a same structure as the $C_3$-$C_{10}$ cycloalkyl group.

The term "$C_1$-$C_{10}$ heterocycloalkyl group" as used herein may be a monovalent cyclic group including at least one heteroatom other than carbon atoms as a ring-forming atom and having 1 to 10 carbon atoms. Examples thereof may include a 1,2,3,4-oxatriazolidinyl group, a tetrahydrofuranyl group, and a tetrahydrothiophenyl group. The term "$C_1$-$C_{10}$ heterocycloalkylene group" as used herein may be a divalent group having a same structure as the $C_1$-$C_{10}$ heterocycloalkyl group.

The term "$C_3$-$C_{10}$ cycloalkenyl group" as used herein may be a monovalent cyclic group that has 3 to 10 carbon atoms and at least one carbon-carbon double bond in its ring, and is not aromatic. Examples thereof may include a cyclopentenyl group, a cyclohexenyl group, and a cycloheptenyl group. The term "$C_3$-$C_{10}$ cycloalkenylene group" as used herein may be a divalent group having a same structure as the $C_3$-$C_{10}$ cycloalkenyl group.

The term "$C_1$-$C_{10}$ heterocycloalkenyl group" as used herein may be a monovalent cyclic group including at least one heteroatom other than carbon atoms as a ring-forming atom, 1 to 10 carbon atoms, and at least one double bond in its ring. Examples of the $C_1$-$C_{10}$ heterocycloalkenyl group may include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkylene group" as used herein may be a divalent group having a same structure as the $C_1$-$C_{10}$ heterocycloalkyl group.

The term "$C_6$-$C_{60}$ aryl group" as used herein may be a monovalent group having a carbocyclic aromatic system having 6 to 60 carbon atoms. The term "$C_6$-$C_{60}$ arylene group" as used herein may be a divalent group having a carbocyclic aromatic system having 6 to 60 carbon atoms. Examples of the $C_6$-$C_{60}$ aryl group may include a phenyl group, a pentalenyl group, a naphthyl group, an azulenyl group, an indacenyl group, an acenaphthyl group, a phenalenyl group, a phenanthrenyl group, an anthracenyl group, a fluoranthenyl group, a triphenylenyl group, a pyrenyl group, a chrysenyl group, a perylenyl group, a pentaphenyl group, a heptalenyl group, a naphthacenyl group, a picenyl group, a hexacenyl group, a pentacenyl group, a rubicenyl group, a coronenyl group, and an ovalenyl group. When the $C_6$-$C_{60}$ aryl group and the $C_6$-$C_{60}$ arylene group each independently include two or more rings, the respective rings may be fused.

The term "$C_1$-$C_{60}$ heteroaryl group" as used herein may be a monovalent group having a heterocyclic aromatic system further including at least one heteroatom other than carbon atoms as a ring-forming atom and 1 to 60 carbon atoms. The term "$C_1$-$C_{60}$ heteroarylene group" as used herein may be a divalent group having a heterocyclic aromatic system further including at least one heteroatom other than carbon atoms as a ring-forming atom and 1 to 60 carbon atoms. Examples of the $C_1$-$C_{60}$ heteroaryl group may include a pyridinyl group, a pyrimidinyl group, a pyrazinyl group, a pyridazinyl group, a triazinyl group, a quinolinyl group, a benzoquinolinyl group, an isoquinolinyl group, a benzoisoquinolinyl group, a quinoxalinyl group, a benzoquinoxalinyl group, a quinazolinyl group, a benzoquinazolinyl group, a cinnolinyl group, a phenanthrolinyl group, a phthalazinyl group, and a naphthyridinyl group. When the $C_1$-$C_{60}$ heteroaryl group and the $C_1$-$C_{60}$ heteroarylene group each independently include two or more rings, the respective rings may be fused.

The term "monovalent non-aromatic condensed polycyclic group" as used herein may be a monovalent group that has two or more condensed rings and only carbon atoms (e.g., 8 to 60 carbon atoms) as ring forming atoms, wherein the molecular structure when considered as a whole is non-aromatic. Examples of the monovalent non-aromatic condensed polycyclic group may include an indenyl group, a fluorenyl group, a spiro-bifluorenyl group, a benzofluorenyl group, an indenophenanthrenyl group, and an indenoanthracenyl group. The term "divalent non-aromatic condensed polycyclic group" as used herein may be a divalent group having a same structure as the monovalent non-aromatic condensed polycyclic group.

The term "monovalent non-aromatic condensed heteropolycyclic group" as used herein may be a monovalent group that has two or more condensed rings and at least one heteroatom other than carbon atoms (e.g., 1 to 60 carbon atoms), as a ring-forming atom, wherein the molecular structure when considered as a whole is non-aromatic. Examples of the monovalent non-aromatic condensed heteropolycyclic group may include a pyrrolyl group, a thiophenyl group, a furanyl group, an indolyl group, a benzoindolyl group, a naphthoindolyl group, an isoindolyl group, a benzoisoindolyl group, a naphthoisoindolyl group, a benzosilolyl group, a benzothiophenyl group, a benzofuranyl group, a carbazolyl group, a dibenzosilolyl group, a dibenzothiophenyl group, a dibenzofuranyl group, an azacarbazolyl group, an azafluorenyl group, an azadibenzosilolyl group, an azadibenzothiophenyl group, an azadibenzofuranyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a benzopyrazolyl group, a benzimidazolyl group, a benzoxazolyl group, a benzothiazolyl group, a benzooxadiazolyl group, a benzothiadiazolyl group, an imidazopyridinyl group, an imidazopyrimidinyl group, an imidazotriazinyl group, an imidazopyrazinyl group, an imidazopyridazinyl group, an indenocarbazolyl group, an indolocarbazolyl group, a benzofurocarbazolyl group, a benzothienocarbazolyl group, a benzosilolocarbazolyl group, a benzoindolocarbazolyl group, a benzocarbazolyl group, a benzonaphthofuranyl group, a benzonaphthothiophenyl group, a benzonaphthosilolyl group, a benzofurodibenzofuranyl group, a benzofurodibenzothiophenyl a group, and benzothienodibenzothiophenyl group. The term "divalent non-aromatic condensed heteropolycyclic group" as used herein may be a divalent group having a same structure as the monovalent non-aromatic condensed heteropolycyclic group.

The term "$C_6$-$C_{60}$ aryloxy group" as used herein indicates —$OA_{102}$ (wherein $A_{102}$ is a $C_6$-$C_{60}$ aryl group), and a $C_6$-$C_{60}$ arylthio group as used herein indicates —$SA_{103}$ (wherein $A_{103}$ is a $C_6$-$C_{60}$ aryl group).

The term "$C_7$-$C_{60}$ aryl alkyl group" used herein may be represented by -$(A_{104})(A_{105})$ (where $A_{104}$ may be a $C_1$-$C_{54}$ alkylene group, and $A_{105}$ may be a $C_6$-$C_{59}$ aryl group), and the term "$C_2$-$C_{60}$ heteroaryl alkyl group" used herein may be represented by -$(A_{106})(A_{107})$ (where $A_{106}$ may be a $C_1$-$C_{59}$ alkylene group, and $A_{107}$ may be a $C_1$-$C_{59}$ heteroaryl group).

The term "$R_{10a}$" as used herein may be:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or any combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or any combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$.

$Q_1$ to $Q_3$, $Q_{11}$ to $Q_{13}$, $Q_{21}$ to $Q_{23}$, and $Q_{31}$ to $Q_{33}$ may each independently be: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or any combination thereof; a $C_7$-$C_{60}$ aryl alkyl group; or a $C_2$-$C_{60}$ heteroaryl alkyl group.

The term "heteroatom" as used herein may be any atom other than a carbon atom or a hydrogen atom. Examples of the heteroatom may include O, S, N, P, Si, B, Ge, Se, or any combination thereof.

A third-row transition metal as used herein may include hafnium (Hf), tantalum (Ta), tungsten (W), rhenium (Re), osmium (Os), iridium (Ir), platinum (Pt), and gold (Au).

The term "Ph" as used herein represents a phenyl group, the term "Me" as used herein represents a methyl group, the term "Et" as used herein represents an ethyl group, the terms "ter-Bu" or "But" as used herein represents a tert-butyl group, and the term "OMe" as used herein represents a methoxy group.

The term "biphenyl group" as used herein may be a phenyl group substituted with a phenyl group. For example, the "biphenyl group" may be a substituted phenyl group having a $C_6$-$C_{60}$ aryl group as a substituent.

The term "terphenyl group" as used herein may be a phenyl group substituted with a biphenyl group. For example, the "terphenyl group" may be "a substituted phenyl group" having a "$C_6$-$C_{60}$ aryl group substituted with a $C_6$-$C_{60}$ aryl group" as a substituent.

The symbols * and *' as used herein, unless defined otherwise, each refer to a binding site to an adjacent atom in a corresponding formula or moiety.

Hereinafter, compounds and a light-emitting device according to embodiments will be described in more detail with reference to Synthesis Examples and Examples. The wording "B was used instead of A" used in describing Synthesis Examples means that an amount of B used was identical to an amount of A used in terms of molar equivalents.

EXAMPLES

Evaluation Example 1

TABLE 1

| | | HOMO (eV) | LUMO (eV) | T1 |
|---|---|---|---|---|
| First electron blocking layer | Compound 1 | −4.72 | −1.12 | 2.60 |
| | Compound 2 | −4.73 | −0.8 | 2.72 |
| | Compound 3 | −4.76 | −1.07 | 2.81 |
| Second electron blocking layer | Compound 4 | −4.78 | −0.88 | 2.67 |
| | Compound 5 | −4.96 | −0.93 | 2.82 |
| | Compound 6 | −4.88 | −1.05 | 2.83 |

Example 1

As an anode, a 15 Ohms per square centimeter ($\Omega/cm^2$) (1,200 Å) ITO glass substrate (available from Corning Co., Ltd) was cut to a size of 50 millimeters (mm)×50 mm×0.7 mm, sonicated in isopropyl alcohol and pure water for 5 minutes in each solvent, cleaned with ultraviolet rays for 30 minutes, cleaned with ozone, and mounted on a vacuum deposition apparatus.

NPD was deposited on the anode to a thickness of 300 Å to form a hole injection layer. HT3 was deposited on the hole injection layer to a thickness of 200 Å to form a hole transport layer. Compound 1 was deposited on the hole transport layer to a thickness of 100 Å to form a first electron blocking layer. Compound 4 was deposited to a thickness of 50 Å to form a second electron blocking layer.

HT130 (as a host) and PD38 (as a phosphorescent dopant) were deposited on the emission auxiliary layer at a weight ratio of 70:30 to a thickness of 250 Å to form an emission layer.

TSPO1 was deposited on the emission layer to a thickness of 200 Å to form a hole blocking layer. TPBI was deposited on the hole blocking layer to a thickness of 300 Å to form an electron transport layer. LiF was deposited on the electron transport layer to a thickness of 10 Å to form an electron injection layer. Al was deposited on the electron injection layer to a thickness of 3,000 Å to form a cathode. Thus, an organic light-emitting device was manufactured having a structure of ITO (1,200 Å)/NPD (300 Å)/HT3 (200 Å)/Compound 1 (100 Å)/Compound 4 (50 Å)/HT130+PD38 (250 Å)/TSPO1 (200 Å)/TPBI (300 Å)/LiF (10 Å)/Al (3,000 Å).

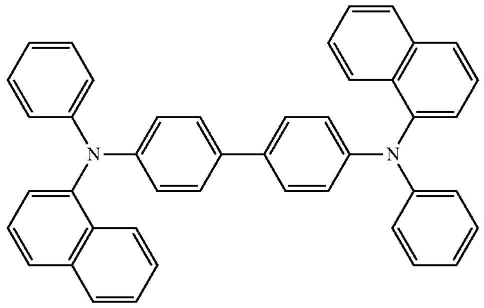

NPD

HT3

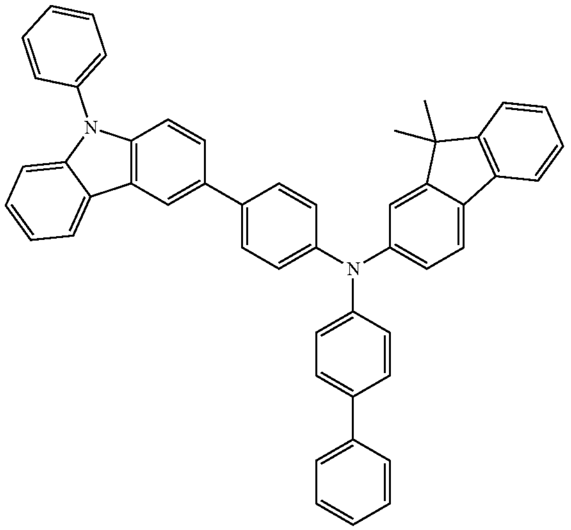

HT130

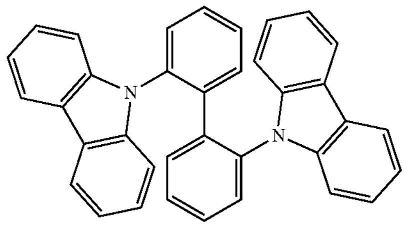

PD38

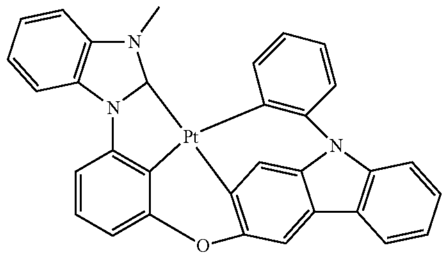

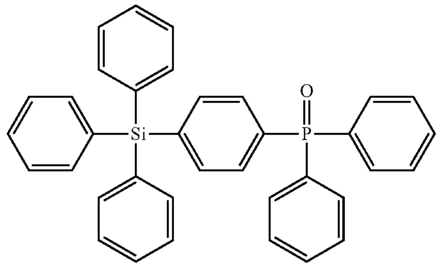

TSPO1

-continued

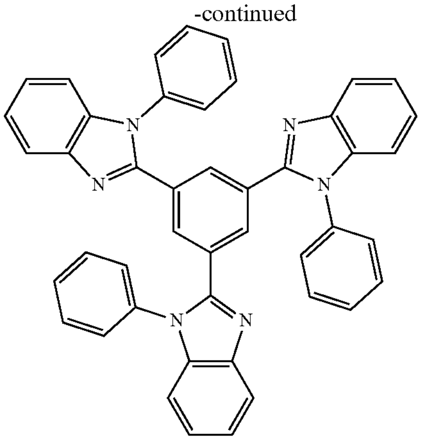

TPBI

Examples 2 to 9 and Comparative Examples 1 to 15

Organic light-emitting devices were manufactured in the same manner as in Example 1, except that the compounds shown in Table 1 were used instead of Compound 1 and Compound 4 as compounds in the formation of the first electron blocking layer and the second electron blocking layer, respectively.

Evaluation Example 2

The driving voltage (V), luminescence efficiency (Cd/A), emission color, and lifespan (T97*2) of the organic light-emitting devices of Examples 1 to 9 and Comparative Examples 1 to 15 at 1,000 cd/$m^2$ were measured by using Keithley SMU236 and luminance meter PR650. The results thereof are shown in Table 2.

TABLE 2

| No. | First electron blocking layer | Second electron blocking layer | Driving voltage (V) | Luminescence efficiency (cd/A) | Lifespan (T97 * 2) |
|---|---|---|---|---|---|
| Example 1 | Compound 1 | Compound 4 | 3.55 | 171.8 | 130 hours |
| Example 2 | Compound 1 | Compound 5 | 3.59 | 176.5 | 150 hours |
| Example 3 | Compound 1 | Compound 6 | 3.51 | 174.6 | 140 hours |
| Example 4 | Compound 2 | Compound 4 | 3.40 | 183.7 | 160 hours |
| Example 5 | Compound 2 | Compound 5 | 3.43 | 186.9 | 200 hours |
| Example 6 | Compound 2 | Compound 6 | 3.41 | 184.6 | 180 hours |
| Example 7 | Compound 3 | Compound 4 | 3.63 | 180.7 | 150 hours |
| Example 8 | Compound 3 | Compound 5 | 3.66 | 182.5 | 190 hours |
| Example 9 | Compound 3 | Compound 6 | 3.60 | 181.6 | 160 hours |
| Comparative Example 1 | Compound 1 | | 3.48 | 168.2 | 90 hours |
| Comparative Example 2 | Compound 2 | | 3.39 | 175.1 | 130 hours |
| Comparative Example 3 | Compound 3 | | 3.59 | 172.3 | 100 hours |
| Comparative Example 4 | Compound 4 | | 3.66 | 174.0 | 140 hours |
| Comparative Example 5 | Compound 5 | | 3.89 | 186.5 | 170 hours |
| Comparative Example 6 | Compound 6 | | 3.75 | 185.7 | 160 hours |
| Comparative Example 7 | Compound 4 | Compound 1 | 3.63 | 171.8 | 130 hours |
| Comparative Example 8 | Compound 4 | Compound 2 | 3.62 | 173.8 | 120 hours |
| Comparative Example 9 | Compound 4 | Compound 3 | 3.65 | 173.7 | 140 hours |
| Comparative Example 10 | Compound 5 | Compound 1 | 3.87 | 180.1 | 160 hours |
| Comparative Example 11 | Compound 5 | Compound 2 | 3.85 | 182.3 | 150 hours |
| Comparative Example 12 | Compound 5 | Compound 3 | 3.89 | 181.7 | 140 hours |
| Comparative Example 13 | Compound 6 | Compound 1 | 3.73 | 176.2 | 140 hours |
| Comparative Example 14 | Compound 6 | Compound 2 | 3.71 | 179.4 | 130 hours |
| Comparative Example 15 | Compound 6 | Compound 3 | 3.75 | 178.1 | 120 hours |

TABLE 2-continued
| No. | First electron blocking layer | Second electron blocking layer | Driving voltage (V) | Luminescence efficiency (cd/A) | Lifespan (T97 * 2) |
| --- | --- | --- | --- | --- | --- |
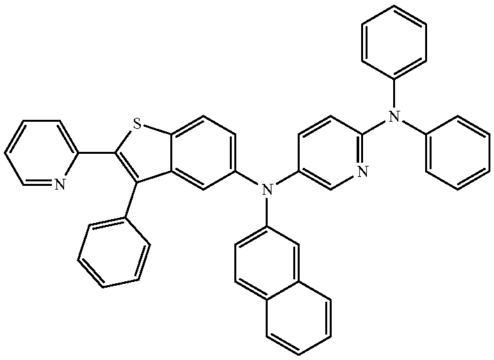
1
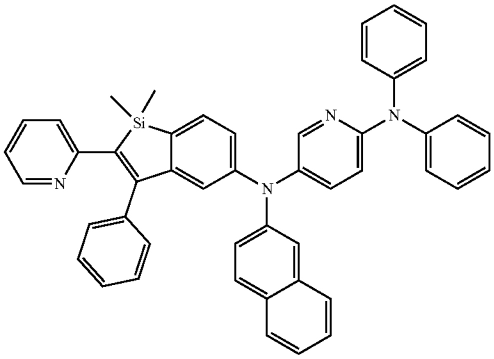
2
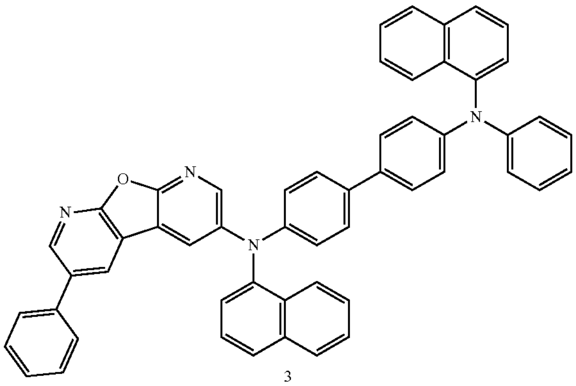 [SMILES: c1ccc(-c2cnc3oc4ncc(N(c5ccc(-c6ccc(N(c7ccccc7)c7cccc8ccccc78)cc6)cc5)c5cccc6ccccc56)cc4c3c2)cc1]
3
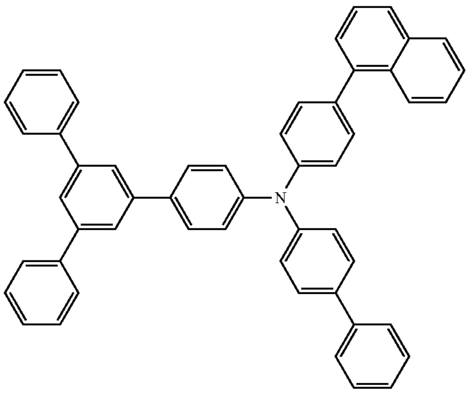
4

TABLE 2-continued

| No. | First electron blocking layer | Second electron blocking layer | Driving voltage (V) | Luminescence efficiency (cd/A) | Lifespan (T97 * 2) |
|---|---|---|---|---|---|

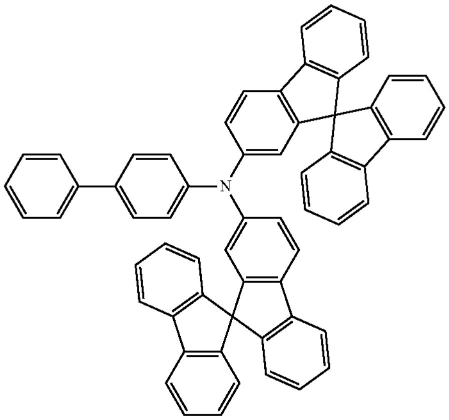

5

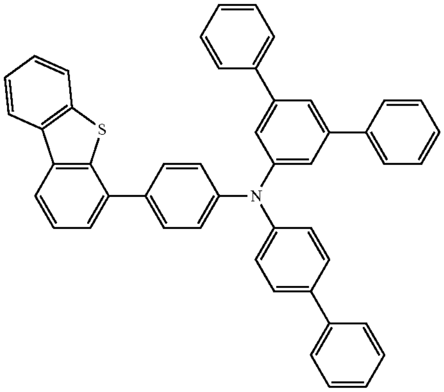

6

Referring to the results of Table 2, the organic light-emitting devices of Examples 1 to 9 were found to have improved driving voltage, luminescence efficiency, and lifespan, as compared with the organic light-emitting devices of Comparative Examples 1 to 15.

As apparent from the foregoing description, the light-emitting devices according to embodiments include specific compounds in the double electron blocking layer. Thus, a high-quality electronic apparatus having excellent driving voltage, luminescence efficiency, and lifespan may be manufactured.

Embodiments have been disclosed herein, and although terms are employed, they are used and are to be interpreted in a generic and descriptive sense only and not for purpose of limitation. In some instances, as would be apparent by one of ordinary skill in the art, features, characteristics, and/or elements described in connection with an embodiment may be used singly or in combination with features, characteristics, and/or elements described in connection with other embodiments unless otherwise specifically indicated. Accordingly, it will be understood by those of ordinary skill in the art that various changes in form and details may be made without departing from the spirit and scope of the disclosure as set forth in the claims.

What is claimed is:

1. A light-emitting device comprising:

a first electrode;

a second electrode facing the first electrode; and an interlayer disposed between the first electrode and the second electrode, wherein the interlayer comprises an emission layer and an electron blocking layer, the electron blocking layer is between the first electrode and the emission layer, the emission layer is between the second electrode and the electron blocking layer, the electron blocking layer comprises a first electron blocking layer and a second electron blocking layer, the first electron blocking layer is between the second electron blocking layer and the first electrode, the second electron blocking layer is between the first electron blocking layer and the emission layer, the first electron blocking layer comprises a first compound represented by Formula 1, the second electron blocking layer comprises a second compound represented by Formula 2, and the first compound is different from the second compound:

[Formula 1]

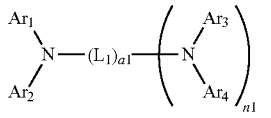

[Formula 2]

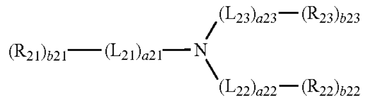

[Formula 3]

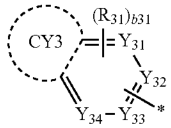

wherein in Formulae 1 to 3, $L_1$ is a benzene group, a naphthalene group, a pyridine group, a pyridazine group, a pyrimidine group, a pyrazine group, a triazine group, a tetrazine group, a quinoline group, or an isoquinoline group, a1 is an integer from 0 to 3, $Ar_1$ to $Ar_4$ are each independently a group represented by Formula 3, a benzene group, a naphthalene group, an anthracene group, a phenanthrene group, a pyridine group, a pyridazine group, a pyrimidine group, a pyrazine group, a triazine group, a tetrazine group, a pentazine group, a dibenzofuran group, a dibenzothiophene group, a dibenzoselenophene group, a carbazole group, a fluorene group, a dibenzosilole group, or a spirobifluorene group, and at least one of $Ar_1$ to $Ar_4$ is a group represented by Formula 3, n1 is an integer of 1 or greater, $Y_{31}$ is N or C, $Y_{32}$ is N or C, $Y_{33}$ is N or C, $Y_{34}$ is N or C, at least one of $Y_{31}$ to $Y_{34}$ is C,

* indicates a binding site to a nitrogen (N) atom in Formula 1,

CY3 is a $C_3$-$C_{60}$ carbocyclic group or a $C_1$-$C_{60}$ heterocyclic group, $L_{21}$ to $L_{23}$ are each independently a single bond, a $C_5$-$C_{30}$ carbocyclic group unsubstituted or substituted with at least one $R_{10a}$, or a $C_1$-$C_{30}$ heterocyclic group unsubstituted or substituted with at least one $R_{10a}$, a21 to a23 are each independently an integer from 0 to 3, $R_{21}$ to $R_{23}$ and $R_{31}$ are each independently hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, a $C_6$-$C_{60}$ aryloxy group unsubstituted or substituted with at least one $R_{10a}$, a $C_6$-$C_{60}$ arylthio group unsubstituted or substituted with at least one $R_{10a}$, a $C_7$-$C_{60}$ aryl alkyl group unsubstituted or substituted with at least one $R_{10a}$, a $C_2$-$C_{60}$ heteroaryl alkyl group unsubstituted or substituted with at least one $R_{10a}$, —$Si(Q_1)(Q_2)(Q_3)$, —$N(Q_1)(Q_2)$, —$B(Q_1)(Q_2)$, —$C(=O)(Q_1)$, —$S(=O)_2(Q_1)$, or —$P(=O)(Q_1)(Q_2)$, b21 to b23 are each independently an integer from 0 to 10, b31 is an integer from 0 to 3, and $R_{10a}$ is:

deuterium (-D), —F, —Cl, —Br, —I, a hydroxyl group, a cyano group, or a nitro group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each unsubstituted or substituted with deuterium, —F, —Cl, —Br, —I, a hydroxyl group, a cyano group, a nitro group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, —$P(=O)(Q_{11})(Q_{12})$, or a combination thereof;

a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, or a $C_2$-$C_{60}$ heteroaryl alkyl group, each unsubstituted or substituted with deuterium, —F, —Cl, —Br, —I, a hydroxyl group, a cyano group, a nitro group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ carbocyclic group, a $C_1$-$C_{60}$ heterocyclic group, a $C_6$-$C_{60}$ aryloxy group, a $C_6$-$C_{60}$ arylthio group, a $C_7$-$C_{60}$ aryl alkyl group, a $C_2$-$C_{60}$ heteroaryl alkyl group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, —$P(=O)(Q_{21})(Q_{22})$, or a combination thereof; or —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, or —$P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ are each independently: hydrogen; deuterium; —F; —Cl; —Br; —I; a hydroxyl group; a cyano group; a nitro group; a $C_1$-$C_{60}$ alkyl group; a $C_2$-$C_{60}$ alkenyl group; a $C_2$-$C_{60}$ alkynyl group; a $C_1$-$C_{60}$ alkoxy group; a $C_3$-$C_{60}$ carbocyclic group or a $C_1$-$C_{60}$ heterocyclic group, each unsubstituted or substituted with deuterium, —F, a cyano group, a $C_1$-$C_{60}$ alkyl group, a $C_1$-$C_{60}$ alkoxy group, a phenyl group, a biphenyl group, or a combination thereof; a $C_7$-$C_{60}$ aryl alkyl group; or a $C_2$-$C_{60}$ heteroaryl alkyl group.

2. The light-emitting device of claim 1, wherein the first compound and the second compound each satisfy Equation 1-1:

$$E_{HOMO,EBL1} < E_{HOMO,EBL2} \quad \text{[Equation 1-1]}$$

wherein in Equation 1-1, $E_{HOMO,\ EBL1}$ is an absolute value (electron volts, eV) of a highest occupied molecular orbital (HOMO) energy level of the first compound, and $E_{HOMO,\ EBL2}$ is an absolute value (eV) of a HOMO energy level of the second compound.

3. The light-emitting device of claim 1, wherein the first compound and the second compound each satisfy Equation 2-1:

$$0.01\ \text{eV} \leq |E_{HOMO,EBL1} - E_{HOMO,EBL2}| \leq 0.5\ \text{eV} \quad \text{[Equation 2-1]}$$

wherein in Equation 2-1, $E_{HOMO,\ EBL1}$ is an absolute value (eV) of a highest occupied molecular orbital (HOMO) energy level of the first compound, and $E_{HOMO,\ EBL2}$ indicates an absolute value (eV) of a HOMO energy level of the second compound.

4. The light-emitting device of claim 1, wherein the interlayer further comprises a hole transport region between the first electrode and the emission layer and an electron transport region between the emission layer and the second electrode, the hole transport region comprises a hole transport layer and the electron blocking layer, the first electron blocking layer is between the second electron blocking layer and the hole transport layer, the second electron blocking layer is between the first electron blocking layer and the emission layer, and the hole transport layer comprises a third compound represented by Formula 201 or Formula 202:

[Formula 201]

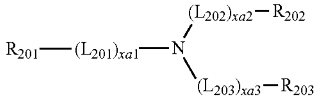

[Formula 202]

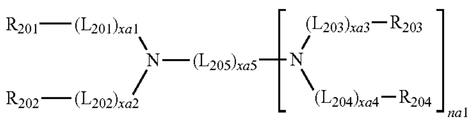

wherein in Formulae 201 and 202, $L_{201}$ to $L_{204}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $L_{205}$ is *—O—**, *—S—**, *—N($Q_{201}$)-*', a $C_1$-$C_{20}$ alkylene group unsubstituted or substituted with at least one $R_{10a}$, a $C_2$-$C_{20}$ alkenylene group unsubstituted or substituted with at least one $R_{10a}$, a $C_3$-$C_{60}$ carbocyclic group unsubstituted or substituted with at least one $R_{10a}$, or a $C_1$-$C_{60}$ heterocyclic group unsubstituted or substituted with at least one $R_{10a}$, wherein * and *' each represent a binding site to a neighboring atom, xa1 to xa4 are each independently an integer from 0 to 5, xa5 is an integer from 1 to 10, $R_{201}$ to $R_{204}$ and $Q_{201}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, $R_{201}$ and $R_{202}$ are optionally bound to each other via a single bond, a $C_1$-$C_8$alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group unsubstituted or substituted with at least one $R_{10a}$, $R_{203}$ and $R_{204}$ are optionally bound to each other via a single bond, a $C_1$-$C_8$alkylene group unsubstituted or substituted with at least one $R_{10a}$, or a $C_2$-$C_5$ alkenylene group unsubstituted or substituted with at least one $R_{10a}$ to form a $C_8$-$C_{60}$ polycyclic group unsubstituted or substituted with at least one $R_{10a}$, na1 is an integer from 1 to 4, and $R_{10a}$ is the same as defined in connection with Formula 2.

5. The light-emitting device of claim 4, wherein the first to third compounds each satisfy Equations 1-1 and 1-2:

$$E_{HOMO,EBL1} < E_{HOMO,EBL2} \quad \text{[Equation 1-1]}$$

$$E_{HOMO,HTL} < E_{HOMO,EBL1} \quad \text{[Equation 1-2]}$$

wherein in Equations 1-1 and 1-2, $E_{HOMO,\ EBL1}$ is an absolute value (eV) of a highest occupied molecular orbital (HOMO) energy level of the first compound, $E_{HOMO,\ EBL2}$ is an absolute value (eV) of a HOMO energy level of the second compound, and $E_{HOMO,\ HTL}$ is an absolute value (eV) of a HOMO energy level of the third compound.

6. The light-emitting device of claim 1, wherein the emission layer comprises a host and a dopant, the dopant comprises a phosphorescent dopant, and the host comprises a fourth compound represented by Formula 301:

$$[Ar_{301}]_{xb11}\text{-}[(L_{301})_{xb1}\text{-}R_{301}]_{xb21} \quad \text{[Formula 301]}$$

wherein in Formula 301, $Ar_{301}$ and $L_{301}$ are each independently a $C_3$-$C_{60}$ carbocyclic group unsubstituted or substituted with at least one $R_{10a}$ or a $C_1$-$C_{60}$ heterocyclic group unsubstituted or substituted with at least one $R_{10a}$, xb11 is 1, 2, or 3, xb1 is an integer from 0 to 5, $R_{301}$ is hydrogen, deuterium, —F, —Cl, —Br, —I, a hydroxyl group, a cyano group, a nitro group, a $C_1$-$C_{60}$ alkyl group unsubstituted or substituted with at least one $R_{10a}$, a $C_2$-$C_{60}$ alkenyl group unsubstituted or substituted with at least one $R_{10a}$, a $C_2$-$C_{60}$ alkynyl group unsubstituted or substituted with at least one $R_{10a}$, a $C_1$-$C_{60}$ alkoxy group unsubstituted or substituted with at least one $R_{10a}$, a $C_3$-$C_{60}$ carbocyclic group unsubstituted or substituted with at least one $R_{10a}$, a $C_1$-$C_{60}$ heterocyclic group unsubstituted or substituted with at least one $R_{10a}$, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), or —P(=O)($Q_{301}$)($Q_{302}$), xb21 is an integer from 1 to 5, $R_{10a}$ is the same as defined in connection with Formula 2, and $Q_{301}$ to $Q_{303}$ are each independently the same as defined in connection with $Q_1$ in Formula 2.

7. The light-emitting device of claim 6, wherein the first compound, the second compound, and the fourth compound each satisfy Equations 1-1 and 1-3:

$$E_{HOMO,EBL1} < E_{HOMO,EBL2} \quad \text{[Equation 1-1]}$$

$$E_{HOMO,EBL2} < E_{HOMO,HOST} \quad \text{[Equation 1-3]}$$

wherein in Equations 1-1 and 1-3, $E_{HOMO,\ EBL1}$ is an absolute value (eV) of a highest occupied molecular orbital (HOMO) energy level of the first compound, $E_{HOMO,\ EBL2}$ is an absolute value (eV) of a HOMO energy level of the second compound, and $E_{HOMO,\ HOST}$ is an absolute value (eV) of a HOMO energy level of the fourth compound.

8. The light-emitting device of claim 1, wherein a thickness of the first electron blocking layer is in a range of about 5 Angstroms (Å) to about 1,000 Å, and a thickness of the second electron blocking layer is in a range of about 1 Å to about 100 Å.

9. The light-emitting device of claim 1, wherein a ratio of a thickness of the second electron blocking layer to a thickness of the first electron blocking layer is in a range of about 1 to about 10.

10. The light-emitting device of claim 1, wherein in Formula 1, n1 is 1 or 2.

11. The light-emitting device of claim 1, wherein in Formula 1, $L_1$ is a group represented by one of Formulae 1-1 to 1-3:

1-1

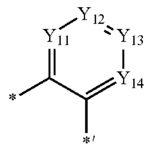

1-2

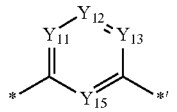

1-3

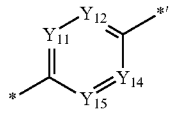

wherein in Formulae 1-1 to 1-3, $Y_{11}$ is N or $C(R_{11})$, $Y_{12}$ is N or $C(R_{12})$, $Y_{13}$ is N or $C(R_{13})$, $Y_{14}$ is N or $C(R_{14})$, $Y_{15}$ is N or $C(R_{15})$, $R_{11}$ to $R_{15}$ are each independently the same as described in connection with $R_{21}$ in Formula 2,

* indicates a binding site to a nitrogen (N) atom bound to $Ar_1$ and $Ar_2$ in Formula 1, and

* indicates a binding site to a nitrogen (N) atom bound to $Ar_3$ and $Ar_4$ in Formula 1.

12. The light-emitting device of claim 1, wherein in Formula 1, $Ar_1$ to $Ar_4$ are each independently a group represented by Formula 3, a benzene group, a naphthalene group, an anthracene group, a phenanthrene group, a pyridine group, a pyrimidine group, a pyrazine group, a triazine group, a dibenzofuran group, a dibenzothiophene group, a dibenzoselenophene group, a carbazole group, a fluorene group, a dibenzosilole group, or a spirobifluorene group, and at least one of $Ar_1$ to $Ar_4$ is a group represented by Formula 3.

13. The light-emitting device of claim 1, wherein in Formula 1, $Ar_1$ is a group represented by Formula 3, and any two of $Ar_2$ to $Ar_4$ are identical to each other.

14. The light-emitting device of claim 1, wherein the group represented by Formula 3 is a group represented by one of Formulae 3-1 to 3-4:

3-1

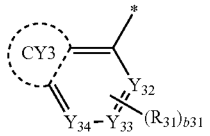

3-2

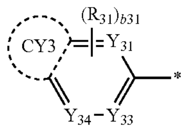

-continued 3-3

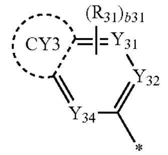

3-4

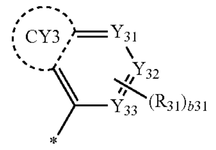

wherein in Formulae 3-1 to 3-4,

CY3 is a $C_3$-$C_{60}$ carbocyclic group or a $C_1$-$C_{60}$ heterocyclic group, $Y_{31}$ is N or C, $Y_{32}$ is N or C, $Y_{33}$ is N or C, $Y_{34}$ is N or C, $R_{31}$ is the same as defined in connection with Formula 3, b31 is an integer from 0 to 3, and

* indicates a binding site to an adjacent atom.

15. The light-emitting device of claim 1, wherein in Formula 3, CY3 is a group represented by one of Formulae CY3-1 to CY3-4:

CY3-1

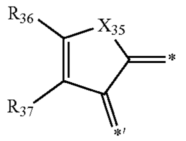

CY3-2

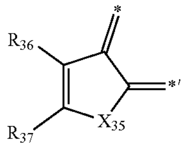

CY3-3

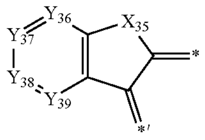

CY3-4

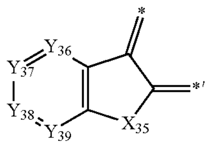

wherein in Formulae CY3-1 to CY3-4, $X_{35}$ is $C(R_{35a})(R_{35b})$, $Si(R_{35a})(R_{35b})$, $N(R_{35a})$, O, S, or Se, $Y_{36}$ is N or $C(R_{36})$, $Y_{37}$ is N or $C(R_{37})$, $Y_{38}$ is N or $C(R_{38})$, $Y_{39}$ is N or $C(R_{39})$, $R_{35a}$, $R_{35b}$, and $R_{36}$ to $R_{39}$ are each independently the same as described in connection with $R_{31}$ in Formula 3,

* indicates a binding site to $Y_{31}$ in Formula 3, and

** indicates a binding site to $Y_{34}$ in Formula 3.

16. The light-emitting device of claim 1, wherein in Formula 2, $L_{21}$ to $L_{23}$ are each independently:

a single bond;

a phenylene group or a naphthylene group; or a phenylene group or a naphthylene group, each unsubstituted or substituted with deuterium, —F, —Cl, —Br, —I, a hydroxyl group, a cyano group, a nitro group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a naphthyl group, or a combination thereof.

17. The light-emitting device of claim 1, wherein $R_{21}$ to $R_{23}$ and $R_{31}$ are each independently:

hydrogen, deuterium, —F, or a cyano group; or a phenyl group, a biphenyl group, a naphthyl group, a pyridinyl group, a pyrimidinyl group, a pyridazinyl group, a pyrazinyl group, a triazinyl group, a quinolinyl group, an isoquinolinyl group, a naphthyl group, an anthracenyl group, a phenanthrenyl group, a dibenzothiophenyl group, or a spirobifluorenyl group, each unsubstituted or substituted with deuterium, —F, a cyano group, a $C_1$-$C_{20}$ alkyl group, a phenyl group, a biphenyl group, a naphthyl group, a pyridinyl group, a pyrimidinyl group, a pyridazinyl group, a pyrazinyl group, a triazinyl group, a quinolinyl group, an isoquinolinyl group, an anthracenyl group, a phenanthrenyl group, a $C_1$-$C_{20}$ alkylphenyl group, a dibenzothiophenyl group, a spirobifluorenyl group, or a combination thereof.

18. An electronic apparatus comprising the light-emitting device of claim 1.

19. The electronic apparatus of claim 18, further comprising a thin-film transistor, wherein the thin-film transistor comprises a source electrode and a drain electrode, and the first electrode of the light-emitting device is electrically connected to at least one of the source electrode and the drain electrode of the thin-film transistor.

20. The electronic apparatus of claim 18, further comprising a color filter, a color-conversion layer, a touchscreen layer, a polarization layer, or a combination thereof.

* * * * *